(12) United States Patent
Thompson et al.

(10) Patent No.: US 10,792,254 B2
(45) Date of Patent: *Oct. 6, 2020

(54) EXTRUDED EXTENDED RELEASE ABUSE DETERRENT PILL

(71) Applicant: Pharmaceutical Manufacturing Research Services, Inc., Horsham, PA (US)

(72) Inventors: Edwin R. Thompson, Horsham, PA (US); Eric R. Thompson, Chalfont, PA (US); Nicholas R. Myslinski, Bensalem, PA (US); Steven F. Kemeny, Philadelphia, PA (US)

(73) Assignee: Pharmaceutical Manufacturing Research Services, Inc., Horsham, PA (US)

( * ) Notice: Subject to any disclaimer, the term of this patent is extended or adjusted under 35 U.S.C. 154(b) by 73 days.

This patent is subject to a terminal disclaimer.

(21) Appl. No.: 15/270,327

(22) Filed: Sep. 20, 2016

(65) Prior Publication Data

US 2017/0007544 A1 Jan. 12, 2017

Related U.S. Application Data

(63) Continuation of application No. 14/574,005, filed on Dec. 17, 2014, now Pat. No. 9,492,444, and a (Continued)

(51) Int. Cl.
*A61K 9/20* (2006.01)
*B29K 71/00* (2006.01)
(Continued)

(52) U.S. Cl.
CPC .......... *A61K 9/2095* (2013.01); *A61K 9/2009* (2013.01); *A61K 9/2013* (2013.01);
(Continued)

(58) Field of Classification Search
CPC . A61K 9/2095; A61K 9/2031; B29K 2071/02
See application file for complete search history.

(56) References Cited

U.S. PATENT DOCUMENTS 3,439,089 A 4/1969 Cherkas
4,450,877 A 5/1984 Walker et al.
(Continued)

FOREIGN PATENT DOCUMENTS

CA 264736 A 10/1926
CA 265145 A 10/1926
(Continued)

OTHER PUBLICATIONS

Schilling ("Implications of Plasticization on the Properties of Hot-Melt Extruded Oral Dosage Forms"; 2009; Dissertation; https://repositories.lib.utexas.edu/bitstream/handle/2152/7527/schillings25096.pdf; accessed Jun. 4, 2018 (Year: 2009).*
(Continued)

*Primary Examiner* — Timothy P Thomas
(74) *Attorney, Agent, or Firm* — McCarter & English, LLP; Yu Lu

(57) ABSTRACT

The present disclosure relates to an oral, extended release pill containing a drug which is homogenously spread throughout a matrix. The pill can be prepared using a hot melt extrusion process and a forming unit. The formed pill meets regulatory guidelines for extended release formulations and can be abuse deterrent to parenteral administration due at least to particle size, viscosity, or purity limitations.

10 Claims, 19 Drawing Sheets

Related U.S. Application Data continuation-in-part of application No. 14/457,714, filed on Aug. 12, 2014, now Pat. No. 10,195,153.

(51) Int. Cl.
| | | |
|---|---|---|
| *A61K 31/485* | (2006.01) | |
| *B29C 48/00* | (2019.01) | |
| *B29C 48/30* | (2019.01) | |
| *B29C 48/40* | (2019.01) | |
| *B29C 48/875* | (2019.01) | |
| *B29K 105/00* | (2006.01) | |

(52) U.S. Cl.
CPC .......... *A61K 9/2018* (2013.01); *A61K 9/2027* (2013.01); *A61K 9/2031* (2013.01); *A61K 9/2054* (2013.01); *A61K 31/485* (2013.01); *B29C 48/0011* (2019.02); *B29C 48/0022* (2019.02); *B29C 48/022* (2019.02); *B29C 48/30* (2019.02); *B29C 48/303* (2019.02); *B29C 48/40* (2019.02); *B29C 48/875* (2019.02); *B29C 2948/92514* (2019.02); *B29C 2948/92704* (2019.02); *B29K 2071/02* (2013.01); *B29K 2105/0038* (2013.01)

(56) References Cited

U.S. PATENT DOCUMENTS

| | | | |
|---|---|---|---|
| 5,141,961 | A | 8/1992 | Coapman |
| 5,202,128 | A | 4/1993 | Morella et al. |
| 5,266,331 | A | 11/1993 | Oshlack et al. |
| 5,431,916 | A | 7/1995 | White |
| 5,458,879 | A | 10/1995 | Singh et al. |
| 5,614,218 | A | 3/1997 | Olsson et al. |
| 5,616,621 | A | 4/1997 | Popli et al. |
| 5,827,852 | A | 10/1998 | Russell et al. |
| 5,840,337 | A | 11/1998 | Cody et al. |
| 5,840,731 | A | 11/1998 | Mayer et al. |
| 5,866,164 | A | 2/1999 | Kuczynski et al. |
| 5,914,129 | A | 6/1999 | Mauskop |
| 6,024,980 | A | 2/2000 | Hoy |
| 6,068,855 | A | 5/2000 | Leslie et al. |
| 6,102,254 | A | 8/2000 | Ross |
| 6,159,501 | A | 12/2000 | Skinhoj |
| 6,160,020 | A | 12/2000 | Ohannesian et al. |
| 6,190,591 | B1 | 2/2001 | Van Lengerich |
| 6,207,674 | B1 | 3/2001 | Smith |
| 6,245,357 | B1 | 6/2001 | Edgren et al. |
| 6,251,430 | B1 | 6/2001 | Zhang et al. |
| 6,277,384 | B1 | 8/2001 | Kaiko et al. |
| 6,309,669 | B1 | 10/2001 | Setterstrom et al. |
| 6,432,450 | B1 | 8/2002 | Gergely et al. |
| 6,488,963 | B1 * | 12/2002 | McGinity ............ A61K 9/2031 424/486 |
| 6,500,459 | B1 | 12/2002 | Chhabra et al. |
| 6,572,891 | B1 | 6/2003 | Ugarkovic |
| 6,627,635 | B2 | 9/2003 | Palermo et al. |
| 6,706,281 | B2 | 3/2004 | Oshlack et al. |
| 6,713,470 | B2 | 3/2004 | Jackson |
| 6,740,333 | B2 | 5/2004 | Beckett et al. |
| 6,753,009 | B2 | 6/2004 | Luber et al. |
| 6,800,668 | B1 | 10/2004 | Odidi et al. |
| 6,869,618 | B2 | 3/2005 | Kiel et al. |
| 6,905,709 | B2 | 6/2005 | Oshlack et al. |
| 6,923,988 | B2 | 8/2005 | Patel et al. |
| 7,141,250 | B2 | 11/2006 | Oshlack et al. |
| 7,201,920 | B2 | 4/2007 | Kumar et al. |
| 7,214,385 | B2 | 5/2007 | Gruber |
| 7,316,821 | B2 | 1/2008 | Oshlack et al. |
| 7,384,653 | B2 | 6/2008 | Wright, IV et al. |
| 7,413,750 | B2 | 8/2008 | Kolter et al. |
| 7,514,100 | B2 | 4/2009 | Oshlack et al. |
| 7,544,676 | B2 | 6/2009 | Dolle et al. |
| 7,655,256 | B2 | 2/2010 | Hughes |
| 7,666,337 | B2 | 2/2010 | Yang et al. |
| 7,670,612 | B2 | 3/2010 | Miller |
| 7,670,627 | B2 | 3/2010 | Shefer et al. |
| 7,718,194 | B2 | 5/2010 | Chenevier et al. |
| 7,744,916 | B2 | 6/2010 | Pauletti et al. |
| 7,754,240 | B2 | 7/2010 | Staniforth et al. |
| 7,780,987 | B2 | 8/2010 | Zhou et al. |
| 7,790,215 | B2 | 9/2010 | Sackler et al. |
| 7,842,307 | B2 | 11/2010 | Oshlack et al. |
| 7,846,460 | B2 | 12/2010 | Chenevier et al. |
| 7,846,476 | B2 | 12/2010 | Oshlack et al. |
| 7,910,128 | B2 | 3/2011 | Chang et al. |
| 7,943,173 | B2 | 5/2011 | Breder et al. |
| 7,968,119 | B2 | 6/2011 | Farrell |
| 8,029,822 | B2 | 10/2011 | Faour et al. |
| 8,075,872 | B2 | 12/2011 | Arkenau-Maric et al. |
| 8,114,383 | B2 | 2/2012 | Bartholomaus et al. |
| 8,124,126 | B2 | 2/2012 | Bosse et al. |
| 8,133,507 | B2 | 3/2012 | Yum et al. |
| 8,138,169 | B2 | 3/2012 | Oronsky et al. |
| 8,143,267 | B2 | 3/2012 | Burch et al. |
| 8,188,108 | B2 | 5/2012 | Mayo-Alvarez et al. |
| 8,202,542 | B1 | 6/2012 | Mehta et al. |
| 8,216,610 | B2 | 7/2012 | Roberts et al. |
| 8,263,125 | B2 | 9/2012 | Vaya et al. |
| 8,313,757 | B2 | 11/2012 | van Lengerich |
| 8,318,105 | B2 | 11/2012 | Selinfreund et al. |
| 8,318,641 | B2 | 11/2012 | Selinfreund et al. |
| 8,333,989 | B2 | 12/2012 | Sukuru |
| 8,337,888 | B2 | 12/2012 | Wright et al. |
| 8,362,029 | B2 | 1/2013 | Evenstad et al. |
| 8,377,453 | B2 | 2/2013 | Han et al. |
| 8,383,152 | B2 | 2/2013 | Jans et al. |
| 8,394,813 | B2 | 3/2013 | Mickle et al. |
| 8,415,401 | B2 | 4/2013 | Yum et al. |
| 8,420,114 | B2 | 4/2013 | Zanella et al. |
| 8,426,411 | B2 | 4/2013 | Wishart et al. |
| 8,445,023 | B2 | 5/2013 | Guimberteau et al. |
| 8,465,776 | B2 | 6/2013 | Hoarau |
| 8,481,560 | B2 | 7/2013 | Stinchcomb et al. |
| 8,486,448 | B2 | 7/2013 | Rahmouni et al. |
| 8,486,449 | B2 | 7/2013 | Rahmouni et al. |
| 8,497,303 | B2 | 7/2013 | Wurn et al. |
| 8,501,160 | B2 | 8/2013 | Cailly-Dufestel et al. |
| 8,518,438 | B2 | 8/2013 | Rashid et al. |
| 8,524,267 | B2 | 9/2013 | Zanella et al. |
| 8,563,038 | B2 | 10/2013 | Andersen et al. |
| 8,575,196 | B2 | 11/2013 | Riggs-Sauthier et al. |
| 8,591,947 | B2 | 11/2013 | Vergez et al. |
| 8,597,681 | B2 | 12/2013 | Park et al. |
| 8,603,514 | B2 | 12/2013 | Yang et al. |
| 8,603,525 | B2 | 12/2013 | Oury et al. |
| 8,609,143 | B2 | 12/2013 | Fischer et al. |
| 8,617,605 | B2 | 12/2013 | Fischer et al. |
| 8,623,401 | B2 | 1/2014 | Modi |
| 8,623,412 | B2 | 1/2014 | Farid et al. |
| 8,652,511 | B2 | 2/2014 | Cottrell et al. |
| 8,653,066 | B2 | 2/2014 | Bosse |
| 8,658,631 | B1 | 2/2014 | Devarakonda et al. |
| 8,685,381 | B2 | 4/2014 | Schlessinger et al. |
| 8,709,479 | B2 | 4/2014 | Oury et al. |
| 8,722,086 | B2 | 5/2014 | Arkenau-Mari et al. |
| 2001/0031278 | A1 | 10/2001 | Oshlack et al. |
| 2001/0044472 | A1 | 11/2001 | Upadhyay et al. |
| 2001/0046971 | A1 | 11/2001 | Hammerly |
| 2002/0055512 | A1 | 5/2002 | Marin et al. |
| 2002/0068718 | A1 | 6/2002 | Pierce |
| 2002/0099013 | A1 | 7/2002 | Piccariello et al. |
| 2002/0164373 | A1 | 11/2002 | Maloney |
| 2003/0049318 | A1 | 3/2003 | Davis et al. |
| 2003/0068375 | A1 | 4/2003 | Wright et al. |
| 2003/0091635 | A1 | 5/2003 | Baichwal et al. |
| 2003/0092724 | A1 | 5/2003 | Kao et al. |
| 2003/0117622 | A1 | 6/2003 | Sevick-Muraca et al. |
| 2003/0125347 | A1 | 7/2003 | Anderson et al. |
| 2003/0180362 | A1 | 9/2003 | Park et al. |
| 2003/0185761 | A1 | 10/2003 | Dugger |
| 2003/0191147 | A1 | 10/2003 | Sherman et al. |
| 2003/0199439 | A1 | 10/2003 | Simon |

(56) References Cited

U.S. PATENT DOCUMENTS

| | | |
|---|---|---|
| 2003/0199496 A1 | 10/2003 | Simon |
| 2003/0203027 A1 | 10/2003 | Verreck et al. |
| 2003/0206898 A1 | 11/2003 | Fischkoff et al. |
| 2003/0224051 A1 | 12/2003 | Fink et al. |
| 2003/0235618 A1 | 12/2003 | Moros et al. |
| 2004/0009172 A1 | 1/2004 | Fischkoff et al. |
| 2004/0010000 A1 | 1/2004 | Ayer et al. |
| 2004/0022787 A1 | 2/2004 | Cohen et al. |
| 2004/0029864 A1 | 2/2004 | MacMillan |
| 2004/0043071 A1 | 3/2004 | Pauletti et al. |
| 2004/0062778 A1 | 4/2004 | Shefer et al. |
| 2004/0110781 A1 | 6/2004 | Harmon et al. |
| 2004/0122104 A1 | 6/2004 | Hirsh et al. |
| 2004/0156872 A1 | 8/2004 | Bosch et al. |
| 2004/0157928 A1 | 8/2004 | Kim et al. |
| 2004/0224020 A1 | 11/2004 | Schoenhard |
| 2004/0228802 A1 | 11/2004 | Chang et al. |
| 2004/0259948 A1 | 12/2004 | Tontonoz et al. |
| 2004/0265378 A1 | 12/2004 | Peng et al. |
| 2005/0004098 A1 | 1/2005 | Britten et al. |
| 2005/0013857 A1 | 1/2005 | Fu et al. |
| 2005/0020613 A1 | 1/2005 | Boehm et al. |
| 2005/0026842 A1 | 2/2005 | Simon |
| 2005/0059023 A1 | 3/2005 | Cantor |
| 2005/0106249 A1 | 5/2005 | Hwang et al. |
| 2005/0143471 A1 | 6/2005 | Gao et al. |
| 2005/0152905 A1 | 7/2005 | Omoigui |
| 2005/0169990 A1 | 8/2005 | Kao et al. |
| 2005/0222136 A1 | 10/2005 | Buschmann et al. |
| 2005/0226929 A1 | 10/2005 | Xie et al. |
| 2005/0233459 A1 | 10/2005 | Melker et al. |
| 2005/0245483 A1 | 11/2005 | Brogmann et al. |
| 2005/0265955 A1 | 12/2005 | Raman et al. |
| 2005/0266032 A1 | 12/2005 | Srinivasan et al. |
| 2005/0266072 A1 | 12/2005 | Oshlack et al. |
| 2006/0008527 A1 | 1/2006 | Lagoviyer et al. |
| 2006/0009478 A1 | 1/2006 | Friedmann et al. |
| 2006/0024365 A1 | 2/2006 | Vaya et al. |
| 2006/0024368 A1 | 2/2006 | Fassihi et al. |
| 2006/0039865 A1 | 2/2006 | Preston et al. |
| 2006/0052278 A1 | 3/2006 | Powell |
| 2006/0062734 A1 | 3/2006 | Melker et al. |
| 2006/0067971 A1 | 3/2006 | Story et al. |
| 2006/0073182 A1 | 4/2006 | Wong et al. |
| 2006/0074422 A1 | 4/2006 | Story et al. |
| 2006/0079557 A1 | 4/2006 | Dolle et al. |
| 2006/0093663 A1 | 5/2006 | Suzuki |
| 2006/0099254 A1 | 5/2006 | Desai et al. |
| 2006/0110327 A1 | 5/2006 | Emigh et al. |
| 2006/0111307 A1 | 5/2006 | Robbins |
| 2006/0115527 A1 | 6/2006 | Hassan et al. |
| 2006/0153915 A1 | 7/2006 | Park et al. |
| 2006/0165790 A1 | 7/2006 | Walden et al. |
| 2006/0177380 A1 | 8/2006 | Emigh et al. |
| 2006/0177381 A1 | 8/2006 | Brooks-Korn |
| 2006/0205752 A1 | 9/2006 | Whitehead |
| 2006/0210604 A1 | 9/2006 | Dadey et al. |
| 2006/0210631 A1 | 9/2006 | Patel et al. |
| 2006/0240105 A1 | 10/2006 | Devane et al. |
| 2006/0246134 A1 | 11/2006 | Venkatesh |
| 2006/0263429 A1 | 11/2006 | Feng |
| 2006/0292214 A1 | 12/2006 | Jenkins et al. |
| 2007/0003617 A1 | 1/2007 | Fischer et al. |
| 2007/0003622 A1 | 1/2007 | Srinivasan et al. |
| 2007/0009444 A1 | 1/2007 | Yamaguchi |
| 2007/0020339 A1 | 1/2007 | Bear |
| 2007/0027203 A1 | 2/2007 | Chen et al. |
| 2007/0042969 A1 | 2/2007 | Rauschkolb-Loffler et al. |
| 2007/0048228 A1 | 3/2007 | Arkenau-Maric et al. |
| 2007/0048377 A1 | 3/2007 | Rajabi-Siahboomi et al. |
| 2007/0072982 A1 | 3/2007 | Choi et al. |
| 2007/0087977 A1 | 4/2007 | Robbins |
| 2007/0104788 A1 | 5/2007 | Mulligan |
| 2007/0134493 A1 | 6/2007 | Meghpara |
| 2007/0140983 A1 | 6/2007 | Hall et al. |
| 2007/0148239 A1 | 6/2007 | Hall et al. |
| 2007/0167438 A1 | 7/2007 | Rosenzweig-Lipson |
| 2007/0190142 A1 | 8/2007 | Breitenbach et al. |
| 2007/0196491 A1 | 8/2007 | Venkatesh |
| 2007/0197661 A1 | 8/2007 | Bubnis et al. |
| 2007/0207200 A1 | 9/2007 | Plachetka et al. |
| 2007/0207222 A1 | 9/2007 | Yu et al. |
| 2007/0212417 A1 | 9/2007 | Cherukuri |
| 2007/0213717 A1 | 9/2007 | Trieu et al. |
| 2007/0213718 A1 | 9/2007 | Trieu |
| 2007/0213822 A1 | 9/2007 | Trieu |
| 2007/0213823 A1 | 9/2007 | Trieu |
| 2007/0213824 A1 | 9/2007 | Trieu |
| 2007/0215511 A1 | 9/2007 | Mehta et al. |
| 2007/0231268 A1 | 10/2007 | Emigh et al. |
| 2007/0232529 A1 | 10/2007 | Mickle et al. |
| 2007/0244093 A1 | 10/2007 | Boehm et al. |
| 2007/0249566 A1 | 10/2007 | Martin et al. |
| 2007/0254027 A1 | 11/2007 | Martin et al. |
| 2007/0281016 A1 | 12/2007 | Kao et al. |
| 2007/0281017 A1 | 12/2007 | Kao et al. |
| 2007/0281018 A1 | 12/2007 | Qiu et al. |
| 2007/0292461 A1 | 12/2007 | Tamarkin et al. |
| 2007/0292508 A1 | 12/2007 | Szamosi et al. |
| 2007/0292510 A1 | 12/2007 | Huang |
| 2007/0298103 A1 | 12/2007 | Hayes |
| 2008/0014228 A1 | 1/2008 | Darmuzey et al. |
| 2008/0014274 A1 | 1/2008 | Bubnis et al. |
| 2008/0020032 A1 | 1/2008 | Crowley et al. |
| 2008/0020039 A1 | 1/2008 | Parikh et al. |
| 2008/0026040 A1 | 1/2008 | Farr et al. |
| 2008/0026062 A1 | 1/2008 | Farr et al. |
| 2008/0031901 A1 | 2/2008 | Qiu et al. |
| 2008/0057122 A1 | 3/2008 | Toney-Parker et al. |
| 2008/0063725 A1 | 3/2008 | Guimberteau et al. |
| 2008/0069871 A1 | 3/2008 | Vaughn et al. |
| 2008/0069878 A1 | 3/2008 | Venkatesh et al. |
| 2008/0069889 A1 | 3/2008 | Cherukuri |
| 2008/0081071 A1 | 4/2008 | Sanghvi et al. |
| 2008/0085304 A1 | 4/2008 | Baichwal et al. |
| 2008/0085312 A1 | 4/2008 | Wilson et al. |
| 2008/0102113 A1 | 5/2008 | Rosenberg |
| 2008/0102123 A1 | 5/2008 | Schachter et al. |
| 2008/0103206 A1 | 5/2008 | Swann et al. |
| 2008/0132751 A1 | 6/2008 | Keller et al. |
| 2008/0152595 A1 | 6/2008 | Emigh et al. |
| 2008/0152704 A1 | 6/2008 | Bonadeo et al. |
| 2008/0171083 A1 | 7/2008 | Staniforth et al. |
| 2008/0175897 A1 | 7/2008 | Plachetka et al. |
| 2008/0193540 A1 | 8/2008 | Soula et al. |
| 2008/0207669 A1 | 8/2008 | Perez et al. |
| 2008/0226702 A1 | 9/2008 | Goldberg |
| 2008/0234237 A1 | 9/2008 | Maddaford et al. |
| 2008/0260815 A1 | 10/2008 | Hayes et al. |
| 2008/0260837 A1 | 10/2008 | Namburi et al. |
| 2008/0260844 A1 | 10/2008 | Soula et al. |
| 2008/0286343 A1 | 11/2008 | Cengic et al. |
| 2008/0286344 A1 | 11/2008 | Darmuzey et al. |
| 2008/0292683 A1 | 11/2008 | Sanghvi et al. |
| 2008/0293695 A1 | 11/2008 | Bristol et al. |
| 2008/0311162 A1 | 12/2008 | Darmuzey et al. |
| 2009/0004267 A1 | 1/2009 | Arkenau-Maric et al. |
| 2009/0004281 A1 | 1/2009 | Nghiem et al. |
| 2009/0004285 A1 | 1/2009 | Yu et al. |
| 2009/0022798 A1 | 1/2009 | Rosenberg et al. |
| 2009/0028873 A1 | 1/2009 | Gant et al. |
| 2009/0035315 A1 | 2/2009 | Christgau et al. |
| 2009/0041838 A1 | 2/2009 | Guimberteau et al. |
| 2009/0061011 A1 | 3/2009 | Talton |
| 2009/0068247 A1 | 3/2009 | Jay |
| 2009/0074866 A1 | 3/2009 | Chen |
| 2009/0081290 A1 | 3/2009 | McKenna et al. |
| 2009/0082466 A1 | 3/2009 | Babul |
| 2009/0087483 A1 | 4/2009 | Sison |
| 2009/0110724 A1 | 4/2009 | Giordano |
| 2009/0124697 A1 | 5/2009 | Cloutier et al. |
| 2009/0143761 A1 | 6/2009 | Cantor et al. |
| 2009/0155193 A1 | 6/2009 | Joabsson et al. |
| 2009/0169626 A1 | 7/2009 | Fleischer et al. |

(56) References Cited

U.S. PATENT DOCUMENTS

| | | |
|---|---|---|
| 2009/0175939 A1 | 7/2009 | Bosse et al. |
| 2009/0198248 A1 | 8/2009 | Yeung et al. |
| 2009/0220611 A1 | 9/2009 | Dargelas et al. |
| 2009/0220613 A1 | 9/2009 | Odidi et al. |
| 2009/0232887 A1 | 9/2009 | Odidi et al. |
| 2009/0238873 A1 | 9/2009 | Chattaraj et al. |
| 2009/0246257 A1 | 10/2009 | Modi |
| 2009/0258947 A1 | 10/2009 | Jain et al. |
| 2009/0317355 A1 | 12/2009 | Roth et al. |
| 2010/0003322 A1 | 1/2010 | Lai et al. |
| 2010/0003332 A1 | 1/2010 | Bae et al. |
| 2010/0010030 A1 | 1/2010 | Jain et al. |
| 2010/0021543 A1 | 1/2010 | Schierstedt |
| 2010/0041759 A1 | 2/2010 | Wilson et al. |
| 2010/0048602 A1 | 2/2010 | Riggs-Sauthier et al. |
| 2010/0051801 A1 | 3/2010 | Erfurth et al. |
| 2010/0076074 A1 | 3/2010 | Gant et al. |
| 2010/0080829 A1 | 4/2010 | Dulieu et al. |
| 2010/0098746 A1 | 4/2010 | King |
| 2010/0099696 A1 | 4/2010 | Soscia et al. |
| 2010/0111830 A1 | 5/2010 | Boyden et al. |
| 2010/0143449 A1 | 6/2010 | Kolesnikov |
| 2010/0152299 A1 | 6/2010 | Vasanthavada et al. |
| 2010/0172989 A1 | 7/2010 | Roth et al. |
| 2010/0196471 A1 | 8/2010 | Jain et al. |
| 2010/0196474 A1 | 8/2010 | Han et al. |
| 2010/0204259 A1 | 8/2010 | Tygesen et al. |
| 2010/0215737 A1 | 8/2010 | Coulter |
| 2010/0226943 A1 | 9/2010 | Brennan et al. |
| 2010/0226978 A1 | 9/2010 | Petereit et al. |
| 2010/0239667 A1 | 9/2010 | Hemmingsen et al. |
| 2010/0249045 A1 | 9/2010 | Babul |
| 2010/0260858 A1 | 10/2010 | Ruddy et al. |
| 2010/0266682 A1 | 10/2010 | Davar et al. |
| 2010/0286100 A1 | 11/2010 | First et al. |
| 2010/0291201 A1 | 11/2010 | Shah et al. |
| 2010/0291205 A1 | 11/2010 | Downie et al. |
| 2010/0304998 A1 | 12/2010 | Sem |
| 2011/0003005 A1 | 1/2011 | Venkatesh et al. |
| 2011/0003006 A1 | 1/2011 | Venkatesh et al. |
| 2011/0008424 A1 | 1/2011 | Chang et al. |
| 2011/0020440 A1 | 1/2011 | Modi et al. |
| 2011/0020451 A1 | 1/2011 | Bartholomaus et al. |
| 2011/0020776 A1 | 1/2011 | Nielsen et al. |
| 2011/0038930 A1 | 2/2011 | Barnscheid et al. |
| 2011/0052685 A1 | 3/2011 | Hou et al. |
| 2011/0077238 A1 | 3/2011 | Leech et al. |
| 2011/0091537 A1 | 4/2011 | Castan et al. |
| 2011/0091563 A1 | 4/2011 | Kurasawa et al. |
| 2011/0104214 A1 | 5/2011 | Oshlack et al. |
| 2011/0104272 A1 | 5/2011 | Hou |
| 2011/0118189 A1 | 5/2011 | Farr et al. |
| 2011/0129530 A1 | 6/2011 | Venkatesh et al. |
| 2011/0142905 A1 | 6/2011 | Bar-Shalom et al. |
| 2011/0142943 A1 | 6/2011 | Rariy et al. |
| 2011/0150989 A1 | 6/2011 | Park et al. |
| 2011/0159048 A1 | 6/2011 | Crain et al. |
| 2011/0159100 A1 | 6/2011 | Andersen et al. |
| 2011/0160239 A1 | 6/2011 | Brodbeck et al. |
| 2011/0165248 A1 | 7/2011 | Machonis |
| 2011/0182987 A1 | 7/2011 | Bawa et al. |
| 2011/0195116 A1 | 8/2011 | Hobbs et al. |
| 2011/0195520 A1 | 8/2011 | Leider et al. |
| 2011/0195989 A1 | 8/2011 | Rudnic et al. |
| 2011/0207761 A1 | 8/2011 | Losev et al. |
| 2011/0218209 A1 | 9/2011 | Yered |
| 2011/0229562 A1 | 9/2011 | Bar et al. |
| 2011/0230816 A1 | 9/2011 | Copp-Howland |
| 2011/0237614 A1 | 9/2011 | Jude-Fishburn et al. |
| 2011/0239745 A1 | 10/2011 | Satcher, Jr. et al. |
| 2011/0245208 A1 | 10/2011 | Diatchenko et al. |
| 2011/0262539 A1 | 10/2011 | Bosse et al. |
| 2011/0287095 A1 | 11/2011 | Park et al. |
| 2011/0311626 A1 | 12/2011 | Venkatesh et al. |
| 2011/0311628 A1 | 12/2011 | Muthusamy et al. |
| 2011/0311631 A1 | 12/2011 | Baer et al. |
| 2012/0009129 A1 | 1/2012 | Brzeczko |
| 2012/0010157 A1 | 1/2012 | Polvino et al. |
| 2012/0015007 A1 | 1/2012 | Bredenberg et al. |
| 2012/0015031 A1 | 1/2012 | Sesha |
| 2012/0021370 A1 | 1/2012 | Drapeau et al. |
| 2012/0022009 A1 | 1/2012 | Bryant |
| 2012/0034306 A1 | 2/2012 | Pollock et al. |
| 2012/0039957 A1 | 2/2012 | Brzeczko et al. |
| 2012/0045506 A1 | 2/2012 | Baer et al. |
| 2012/0059065 A1 | 3/2012 | Barnscheid et al. |
| 2012/0063996 A1 | 3/2012 | Bosch et al. |
| 2012/0064159 A1 | 3/2012 | Chauhan et al. |
| 2012/0065220 A1 | 3/2012 | Barnscheid et al. |
| 2012/0083506 A1 | 4/2012 | Herry et al. |
| 2012/0088786 A1 | 4/2012 | Dadagher et al. |
| 2012/0093929 A1 | 4/2012 | Oksche et al. |
| 2012/0100183 A1 | 4/2012 | Schlessinger et al. |
| 2012/0107400 A1 | 5/2012 | Muthusamy et al. |
| 2012/0121594 A1 | 5/2012 | Smith |
| 2012/0121724 A1 | 5/2012 | Maibach |
| 2012/0135075 A1 | 5/2012 | Mohammad |
| 2012/0135077 A1 | 5/2012 | Mehta et al. |
| 2012/0141554 A1 | 6/2012 | Dill |
| 2012/0164209 A1 | 6/2012 | Shah et al. |
| 2012/0164220 A1 | 6/2012 | Huang |
| 2012/0202838 A1 | 8/2012 | Ghosh et al. |
| 2012/0205532 A1 | 8/2012 | Mazza |
| 2012/0207825 A1 | 8/2012 | Roy et al. |
| 2012/0237556 A1 | 9/2012 | Schlessinger et al. |
| 2012/0245156 A1 | 9/2012 | Nguyen |
| 2012/0251590 A1 | 10/2012 | Cruz et al. |
| 2012/0282335 A1 | 11/2012 | Venkatesh et al. |
| 2012/0289534 A1 | 11/2012 | Pergolizzi et al. |
| 2012/0321674 A1 | 12/2012 | Vachon et al. |
| 2013/0004415 A1 | 1/2013 | Moudgil et al. |
| 2013/0011479 A1 | 1/2013 | Angeli et al. |
| 2013/0017262 A1 | 1/2013 | Mullen et al. |
| 2013/0022646 A1 | 1/2013 | Rudnic et al. |
| 2013/0022676 A1 | 1/2013 | Mullen et al. |
| 2013/0022677 A1 | 1/2013 | Mullen et al. |
| 2013/0023553 A1 | 1/2013 | Jude-Fishburn et al. |
| 2013/0028955 A1 | 1/2013 | Tolia |
| 2013/0028970 A1 | 1/2013 | Schwier et al. |
| 2013/0028972 A1 | 1/2013 | Schwier et al. |
| 2013/0030360 A1 | 1/2013 | Stopek et al. |
| 2013/0059010 A1 | 3/2013 | Herry et al. |
| 2013/0102959 A1 | 4/2013 | Stopek et al. |
| 2013/0115249 A1 | 5/2013 | Vergez et al. |
| 2013/0122098 A1 | 5/2013 | First et al. |
| 2013/0122101 A1 | 5/2013 | Habib et al. |
| 2013/0123294 A1 | 5/2013 | Lebon et al. |
| 2013/0129825 A1 | 5/2013 | Billoet |
| 2013/0129826 A1 | 5/2013 | Gei Ler et al. |
| 2013/0129828 A1 | 5/2013 | Talton |
| 2013/0136792 A1 | 5/2013 | Draper et al. |
| 2013/0156853 A1 | 6/2013 | Zhang et al. |
| 2013/0165467 A1 | 6/2013 | Hayes et al. |
| 2013/0168321 A1 | 7/2013 | Cannon et al. |
| 2013/0197021 A1 | 8/2013 | Mohammad et al. |
| 2013/0209557 A1 | 8/2013 | Barnscheid |
| 2013/0209561 A1 | 8/2013 | Kao et al. |
| 2013/0217777 A1 | 8/2013 | Kirkorian |
| 2013/0225412 A1 | 8/2013 | Sardari Lodriche et al. |
| 2013/0225625 A1 | 8/2013 | Barnscheid et al. |
| 2013/0225697 A1 | 8/2013 | Barnscheid et al. |
| 2013/0230587 A1 | 9/2013 | Pilgaonkar et al. |
| 2013/0237559 A1 | 9/2013 | Ortiz et al. |
| 2013/0245054 A1 | 9/2013 | Prater et al. |
| 2013/0259941 A1 | 10/2013 | O'Donnell |
| 2013/0273153 A1 | 10/2013 | Park et al. |
| 2013/0273162 A1 | 10/2013 | Li |
| 2013/0280176 A1 | 10/2013 | Diezi et al. |
| 2013/0280177 A1 | 10/2013 | Raman et al. |
| 2013/0280338 A1 | 10/2013 | Wening et al. |
| 2013/0303623 A1 | 11/2013 | Barnscheid et al. |
| 2013/0330409 A1 | 12/2013 | Mohammad |
| 2013/0345250 A1 | 12/2013 | Fleming |
| 2014/0010873 A1 | 1/2014 | Tygesen et al. |

(56) References Cited

U.S. PATENT DOCUMENTS

| | | | |
|---|---|---|---|
| 2014/0010874 A1 | 1/2014 | Sackler | |
| 2014/0017310 A1* | 1/2014 | Gower | A61K 9/0002 424/474 |
| 2014/0031734 A1 | 1/2014 | Saxena et al. | |
| 2014/0045801 A1 | 2/2014 | Rossi | |
| 2014/0050787 A1 | 2/2014 | Tygesen et al. | |
| 2014/0056979 A1 | 2/2014 | Huang | |
| 2014/0066516 A1 | 3/2014 | Clarke et al. | |
| 2014/0094438 A1 | 4/2014 | Mitchell | |
| 2014/0105977 A1 | 4/2014 | Devarakonda et al. | |
| 2014/0105987 A1 | 4/2014 | Rariy et al. | |
| 2014/0112984 A1 | 4/2014 | Arkenau-Maric et al. | |
| 2014/0112989 A1 | 4/2014 | Bartholomaus et al. | |
| 2014/0127300 A1 | 5/2014 | Tengler et al. | |
| 2014/0171481 A1 | 6/2014 | Liepold et al. | |
| 2015/0057304 A1 | 2/2015 | Thompson et al. | |
| 2015/0283087 A1 | 10/2015 | Vamvakas et al. | |

FOREIGN PATENT DOCUMENTS

| | | |
|---|---|---|
| CA | 265559 A | 11/1926 |
| CA | 2319353 A1 | 8/1999 |
| CA | 2408106 A1 | 11/2001 |
| CA | 2386794 A1 | 1/2002 |
| CA | 2544404 A1 | 6/2005 |
| CA | 2573583 A1 | 2/2006 |
| CA | 2649265 A1 | 8/2007 |
| CA | 2690829 A1 | 1/2009 |
| CA | 2737307 A1 | 4/2010 |
| CA | 2750400 A1 | 7/2010 |
| CA | 2766179 A1 | 12/2010 |
| CA | 2847613 A1 | 3/2013 |
| CN | 101824144 A | 9/2010 |
| CN | 101987081 A | 3/2011 |
| CN | 102344534 A | 2/2012 |
| CN | 102389423 A | 3/2012 |
| CN | 102648985 A | 8/2012 |
| CN | 103040829 A | 4/2013 |
| CN | 103070840 A | 5/2013 |
| CN | 103637987 A | 3/2014 |
| CN | 103637998 A | 3/2014 |
| DE | 2326141 A1 | 12/1973 |
| DE | 2705051 A1 | 8/1977 |
| DE | 10215067 A1 | 10/2003 |
| DE | 10215131 A1 | 10/2003 |
| DE | 202006014131 U1 | 1/2007 |
| DE | 102007021549 A1 | 11/2008 |
| EP | 103991 A2 | 3/1984 |
| EP | 0152292 A2 | 8/1985 |
| EP | 459387 A2 | 12/1991 |
| EP | 1663229 A2 | 6/2006 |
| EP | 1980245 A1 | 10/2008 |
| EP | 2007360 A1 | 12/2008 |
| EP | 2067471 A1 | 6/2009 |
| EP | 2106799 A1 | 10/2009 |
| EP | 2123626 A1 | 11/2009 |
| EP | 2343071 A1 | 7/2011 |
| EP | 2359812 A1 | 8/2011 |
| EP | 2444064 A1 | 4/2012 |
| EP | 2457900 A1 | 5/2012 |
| EP | 2548863 A1 | 1/2013 |
| EP | 2548876 A1 | 1/2013 |
| EP | 2586607 A1 | 5/2013 |
| EP | 2626358 A1 | 8/2013 |
| FR | 2850576 A1 | 8/2004 |
| FR | 2878158 A1 | 5/2006 |
| FR | 2878161 A1 | 5/2006 |
| FR | 2892937 A1 | 5/2007 |
| FR | 2960775 A1 | 12/2011 |
| GB | 135381 A | 12/1919 |
| HU | 9903375 A2 | 2/2000 |
| IN | 2005MU01013 | 6/2007 |
| IN | 2006KO00351 | 7/2007 |
| IN | 2005MU01012 | 8/2007 |
| IN | 2009DE00453 | 4/2013 |
| JP | 55084166 | 6/1980 |
| JP | 60092214 | 5/1985 |
| JP | 11033084 | 2/1999 |
| JP | 2009256214 A | 11/2009 |
| JP | 2010053078 A | 3/2010 |
| JP | 2010173976 A | 8/2010 |
| JP | 2011256115 A | 12/2011 |
| JP | 2013249458 A | 12/2013 |
| KR | 2008026754 | 3/2008 |
| KR | 1203186 | 11/2012 |
| PL | 133984 B2 | 7/1985 |
| WO | WO-8503439 A1 | 8/1985 |
| WO | WO-9107950 A1 | 6/1991 |
| WO | WO-9324154 A1 | 12/1993 |
| WO | WO-9408551 A2 | 4/1994 |
| WO | WO-9418970 A1 | 9/1994 |
| WO | WO-9425009 A1 | 11/1994 |
| WO | WO-9426731 A1 | 11/1994 |
| WO | WO-9523591 A1 | 9/1995 |
| WO | WO-9614059 A1 | 5/1996 |
| WO | WO-9623486 A1 | 8/1996 |
| WO | WO-9704780 A2 | 2/1997 |
| WO | WO-9720556 A1 | 6/1997 |
| WO | WO-9720561 A1 | 6/1997 |
| WO | WO-199733566 A2 | 9/1997 |
| WO | WO-9749384 A1 | 12/1997 |
| WO | WO-9803179 A1 | 1/1998 |
| WO | WO-9818610 A1 | 5/1998 |
| WO | WO-199825613 A2 | 6/1998 |
| WO | WO-9832427 A1 | 7/1998 |
| WO | WO-9850044 A1 | 11/1998 |
| WO | WO-9850075 A1 | 11/1998 |
| WO | WO-9907413 A1 | 2/1999 |
| WO | WO-9944591 A1 | 9/1999 |
| WO | WO-9953922 A1 | 10/1999 |
| WO | WO-9966919 A1 | 12/1999 |
| WO | WO-0021504 A1 | 4/2000 |
| WO | WO-0029022 A1 | 5/2000 |
| WO | WO-0029023 A1 | 5/2000 |
| WO | WO-0038649 A1 | 7/2000 |
| WO | WO-0061537 A2 | 10/2000 |
| WO | WO-0061541 A2 | 10/2000 |
| WO | WO-0108662 A1 | 2/2001 |
| WO | WO-0112584 A2 | 2/2001 |
| WO | WO-0115667 A1 | 3/2001 |
| WO | WO-0132101 A1 | 5/2001 |
| WO | WO-0132928 A2 | 5/2001 |
| WO | WO-0176576 A2 | 10/2001 |
| WO | WO-0185150 A2 | 11/2001 |
| WO | WO-0185257 A2 | 11/2001 |
| WO | WO-0191736 A2 | 12/2001 |
| WO | WO-0205647 A1 | 1/2002 |
| WO | WO-0232395 A2 | 4/2002 |
| WO | WO-0234237 A1 | 5/2002 |
| WO | WO-02051432 A1 | 7/2002 |
| WO | WO-02056861 A2 | 7/2002 |
| WO | WO-02100351 A2 | 12/2002 |
| WO | WO-2003004009 A1 | 1/2003 |
| WO | WO-03013481 A1 | 2/2003 |
| WO | WO-03020200 A2 | 3/2003 |
| WO | WO-03024430 A1 | 3/2003 |
| WO | WO-03032990 A2 | 4/2003 |
| WO | WO-03034991 A2 | 5/2003 |
| WO | WO-03051878 A1 | 6/2003 |
| WO | WO-03063834 A1 | 8/2003 |
| WO | WO-03065988 A2 | 8/2003 |
| WO | WO-03066029 A2 | 8/2003 |
| WO | WO-03066030 A2 | 8/2003 |
| WO | WO-03068197 A1 | 8/2003 |
| WO | WO-03079972 A2 | 10/2003 |
| WO | WO-03088991 A1 | 10/2003 |
| WO | WO-03092648 A1 | 11/2003 |
| WO | WO-03101476 A1 | 12/2003 |
| WO | WO-2004026256 A2 | 4/2004 |
| WO | WO-2004039320 A2 | 5/2004 |
| WO | WO-2004045551 A2 | 6/2004 |
| WO | WO-2004054542 A2 | 7/2004 |
| WO | WO-2004064832 A2 | 8/2004 |

(56) References Cited

FOREIGN PATENT DOCUMENTS

| | | |
|---|---|---|
| WO | WO-2004069135 A2 | 8/2004 |
| WO | WO-2004075832 A2 | 9/2004 |
| WO | WO-2004082588 A2 | 9/2004 |
| WO | WO-2004082719 A1 | 9/2004 |
| WO | WO-2004084868 A1 | 10/2004 |
| WO | WO-2004108163 A1 | 12/2004 |
| WO | WO-2005000310 A1 | 1/2005 |
| WO | WO-2005000331 A2 | 1/2005 |
| WO | WO-2005002597 A1 | 1/2005 |
| WO | WO-2005004989 A2 | 1/2005 |
| WO | WO-2005009409 A2 | 2/2005 |
| WO | WO-2005028539 A2 | 3/2005 |
| WO | WO-2005030181 A1 | 4/2005 |
| WO | WO-2005030182 A1 | 4/2005 |
| WO | WO-2005032474 A2 | 4/2005 |
| WO | WO-2005032555 A2 | 4/2005 |
| WO | WO-2005038049 A2 | 4/2005 |
| WO | WO-2005046727 A2 | 5/2005 |
| WO | WO-2005051356 A1 | 6/2005 |
| WO | WO-2005058303 A1 | 6/2005 |
| WO | WO-2005063206 A1 | 7/2005 |
| WO | WO-2005063219 A2 | 7/2005 |
| WO | WO-2005070465 A2 | 8/2005 |
| WO | WO-2005079760 A1 | 9/2005 |
| WO | WO-2005092306 A1 | 10/2005 |
| WO | WO-2005102338 A1 | 11/2005 |
| WO | WO-2005103070 A1 | 11/2005 |
| WO | WO-2005107467 A2 | 11/2005 |
| WO | WO-2005107726 A2 | 11/2005 |
| WO | WO-2005123192 A2 | 12/2005 |
| WO | WO-2005123193 A2 | 12/2005 |
| WO | WO-2006014967 A1 | 2/2006 |
| WO | WO-2006020930 A2 | 2/2006 |
| WO | WO-2006024018 A2 | 3/2006 |
| WO | WO-2006024881 A2 | 3/2006 |
| WO | WO-2006030402 A2 | 3/2006 |
| WO | WO-2006046114 A2 | 5/2006 |
| WO | WO-2006050165 A2 | 5/2006 |
| WO | WO-2006069030 A1 | 6/2006 |
| WO | WO-2006069202 A2 | 6/2006 |
| WO | WO-2006075123 A1 | 7/2006 |
| WO | WO-2006085101 A2 | 8/2006 |
| WO | WO-2006092691 A1 | 9/2006 |
| WO | WO-2006099541 A2 | 9/2006 |
| WO | WO-2006103418 A1 | 10/2006 |
| WO | WO-2006103551 A1 | 10/2006 |
| WO | WO-2006105205 A1 | 10/2006 |
| WO | WO-2006116148 A2 | 11/2006 |
| WO | WO-2006133733 A1 | 12/2006 |
| WO | WO-2006138278 A1 | 12/2006 |
| WO | WO-2007021970 A2 | 2/2007 |
| WO | WO-2007036671 A2 | 4/2007 |
| WO | WO-2007050631 A2 | 5/2007 |
| WO | WO-2007056142 A2 | 5/2007 |
| WO | WO-2007058960 A1 | 5/2007 |
| WO | WO-2007/070632 A2 | 6/2007 |
| WO | WO-2007072503 A2 | 6/2007 |
| WO | WO-2007087452 A2 | 8/2007 |
| WO | WO-2007089328 A2 | 8/2007 |
| WO | WO-2007094694 A1 | 8/2007 |
| WO | WO-2007106550 A2 | 9/2007 |
| WO | WO-2007128349 A1 | 11/2007 |
| WO | WO-2007128884 A1 | 11/2007 |
| WO | WO-2007131357 A1 | 11/2007 |
| WO | WO-2007133583 A2 | 11/2007 |
| WO | WO-2007135193 A2 | 11/2007 |
| WO | WO-2007141328 A1 | 12/2007 |
| WO | WO-2007149438 A2 | 12/2007 |
| WO | WO-2008001341 A1 | 1/2008 |
| WO | WO-2008007152 A2 | 1/2008 |
| WO | WO-2008008364 A2 | 1/2008 |
| WO | WO-2008011169 A2 | 1/2008 |
| WO | WO-2008013710 A2 | 1/2008 |
| WO | WO-2008/021394 A2 | 2/2008 |
| WO | WO-2008023261 A1 | 2/2008 |
| WO | WO-2008027350 A2 | 3/2008 |
| WO | WO-2008027442 A2 | 3/2008 |
| WO | WO-2008033351 A2 | 3/2008 |
| WO | WO-2008033523 A1 | 3/2008 |
| WO | WO-2008057579 A2 | 5/2008 |
| WO | WO-2008057608 A2 | 5/2008 |
| WO | WO-2008060552 A2 | 5/2008 |
| WO | WO-2008063625 A2 | 5/2008 |
| WO | WO-2008067222 A1 | 6/2008 |
| WO | WO-2008068471 A1 | 6/2008 |
| WO | WO-2008070268 A2 | 6/2008 |
| WO | WO-2008086804 A2 | 7/2008 |
| WO | WO-2008097976 A1 | 8/2008 |
| WO | WO-2008100977 A2 | 8/2008 |
| WO | WO-2008106429 A2 | 9/2008 |
| WO | WO-2008107410 A1 | 9/2008 |
| WO | WO-2008108957 A2 | 9/2008 |
| WO | WO-2008108958 A2 | 9/2008 |
| WO | WO-2008108986 A2 | 9/2008 |
| WO | WO-2008131056 A2 | 10/2008 |
| WO | WO-2008131057 A2 | 10/2008 |
| WO | WO-2008132712 A2 | 11/2008 |
| WO | WO-2008133928 A2 | 11/2008 |
| WO | WO-2008134600 A1 | 11/2008 |
| WO | WO-2008135283 A1 | 11/2008 |
| WO | WO-2008140459 A1 | 11/2008 |
| WO | WO-2008140460 A1 | 11/2008 |
| WO | WO-2008140461 A1 | 11/2008 |
| WO | WO-2008141189 A1 | 11/2008 |
| WO | WO-2008148798 A2 | 12/2008 |
| WO | WO-2008155620 A1 | 12/2008 |
| WO | WO-2008157308 A2 | 12/2008 |
| WO | WO-2009002299 A1 | 12/2008 |
| WO | WO-2009005613 A2 | 1/2009 |
| WO | WO-2009005803 A1 | 1/2009 |
| WO | WO-2009014534 A1 | 1/2009 |
| WO | WO-2009021055 A1 | 2/2009 |
| WO | WO-2009023672 A2 | 2/2009 |
| WO | WO-2009026241 A1 | 2/2009 |
| WO | WO-2009042960 A1 | 4/2009 |
| WO | WO-2009047175 A2 | 4/2009 |
| WO | WO-2009073686 A1 | 6/2009 |
| WO | WO-2009076361 A1 | 6/2009 |
| WO | WO-2009076764 A1 | 6/2009 |
| WO | WO-2009089134 A1 | 7/2009 |
| WO | WO-2009100118 A1 | 8/2009 |
| WO | WO-2009104838 A1 | 8/2009 |
| WO | WO-2009109911 A1 | 9/2009 |
| WO | WO-2009114648 A1 | 9/2009 |
| WO | WO-2009118764 A1 | 10/2009 |
| WO | WO-2009120889 A2 | 10/2009 |
| WO | WO-2009121496 A2 | 10/2009 |
| WO | WO-2009124755 A1 | 10/2009 |
| WO | WO-2009126931 A2 | 10/2009 |
| WO | WO-2009/137086 A1 | 11/2009 |
| WO | WO-2009134336 A1 | 11/2009 |
| WO | WO-2009143295 A1 | 11/2009 |
| WO | WO-2009143299 A1 | 11/2009 |
| WO | WO-2009/152133 A1 | 12/2009 |
| WO | WO-2010000073 A1 | 1/2010 |
| WO | WO-2010017821 A1 | 2/2010 |
| WO | WO-2010032128 A1 | 3/2010 |
| WO | WO-2010033195 A1 | 3/2010 |
| WO | WO-2010068789 A1 | 6/2010 |
| WO | WO-2010069050 A1 | 6/2010 |
| WO | WO-2010083894 A1 | 7/2010 |
| WO | WO-2010089132 A1 | 8/2010 |
| WO | WO-2010096045 A1 | 8/2010 |
| WO | WO-2010103365 A2 | 9/2010 |
| WO | WO-2010103367 A1 | 9/2010 |
| WO | WO-2010123999 A2 | 10/2010 |
| WO | WO-2010124089 A2 | 10/2010 |
| WO | WO-2010127345 A2 | 11/2010 |
| WO | WO-2010127346 A1 | 11/2010 |
| WO | WO-2010132095 A1 | 11/2010 |
| WO | WO-2010135340 A2 | 11/2010 |
| WO | WO-2010140007 A2 | 12/2010 |
| WO | WO-2010141505 A1 | 12/2010 |
| WO | WO-2010150930 A1 | 12/2010 |

(56) References Cited

FOREIGN PATENT DOCUMENTS

| | | |
|---|---|---|
| WO | WO-2010151020 A2 | 12/2010 |
| WO | WO-2010151823 A1 | 12/2010 |
| WO | WO-2011005671 A1 | 1/2011 |
| WO | WO-2011006012 A1 | 1/2011 |
| WO | WO-2011008298 A2 | 1/2011 |
| WO | WO-2011009603 A1 | 1/2011 |
| WO | WO-2011009604 A1 | 1/2011 |
| WO | WO-2011011060 A1 | 1/2011 |
| WO | WO-2011011199 A1 | 1/2011 |
| WO | WO-2011011543 A1 | 1/2011 |
| WO | WO-2011012715 A1 | 2/2011 |
| WO | WO-2011039768 A2 | 4/2011 |
| WO | WO-2011045769 A2 | 4/2011 |
| WO | WO-2011057199 A1 | 5/2011 |
| WO | WO-2011066287 A1 | 6/2011 |
| WO | WO-2011066980 A2 | 6/2011 |
| WO | WO-2011068723 A1 | 6/2011 |
| WO | WO-2011068881 A1 | 6/2011 |
| WO | WO-2011084593 A2 | 7/2011 |
| WO | WO-2011086193 A1 | 7/2011 |
| WO | WO-2011088140 A1 | 7/2011 |
| WO | WO-2011106076 A1 | 9/2011 |
| WO | WO-2011107750 A2 | 9/2011 |
| WO | WO-2011107855 A2 | 9/2011 |
| WO | WO-2011120084 A1 | 10/2011 |
| WO | WO 2011123719 A2 | 10/2011 |
| WO | WO-2011123866 A1 | 10/2011 |
| WO | WO-2011127467 A1 | 10/2011 |
| WO | WO-2011139595 A2 | 11/2011 |
| WO | WO-2012007159 A2 | 1/2012 |
| WO | WO-2012011917 A1 | 1/2012 |
| WO | WO-2012016569 A1 | 2/2012 |
| WO | WO-2012020097 A2 | 2/2012 |
| WO | WO-2012021819 A1 | 2/2012 |
| WO | WO-2012028319 A1 | 3/2012 |
| WO | WO-2012037457 A1 | 3/2012 |
| WO | WO-2012052955 A1 | 4/2012 |
| WO | WO-2012054071 A1 | 4/2012 |
| WO | WO-2012054831 A2 | 4/2012 |
| WO | WO-2012061779 A1 | 5/2012 |
| WO | WO-2012063257 A2 | 5/2012 |
| WO | WO-2012069175 A1 | 5/2012 |
| WO | WO-2012076907 A2 | 6/2012 |
| WO | WO-2012077110 A2 | 6/2012 |
| WO | WO-2012085236 A1 | 6/2012 |
| WO | WO-2012085656 A2 | 6/2012 |
| WO | WO-2012085657 A2 | 6/2012 |
| WO | WO-2012087377 A1 | 6/2012 |
| WO | WO-2012098281 A2 | 7/2012 |
| WO | WO-2012106343 A1 | 8/2012 |
| WO | WO-2012112933 A1 | 8/2012 |
| WO | WO-2012112952 A1 | 8/2012 |
| WO | WO-2012116278 A1 | 8/2012 |
| WO | WO-2012116279 A1 | 8/2012 |
| WO | WO-2012121461 A1 | 9/2012 |
| WO | WO-2012127506 A1 | 9/2012 |
| WO | WO-2012131463 A2 | 10/2012 |
| WO | WO-2012139191 A1 | 10/2012 |
| WO | WO-2012177986 A2 | 12/2012 |
| WO | WO-2013000578 A1 | 1/2013 |
| WO | WO-2013003845 A1 | 1/2013 |
| WO | WO-2013010880 A1 | 1/2013 |
| WO | WO-2013010881 A1 | 1/2013 |
| WO | WO-2013015545 A1 | 1/2013 |
| WO | WO-2013017234 A1 | 2/2013 |
| WO | WO-2013038267 A1 | 3/2013 |
| WO | WO-2013038268 A1 | 3/2013 |
| WO | WO-2013050539 A2 | 4/2013 |
| WO | WO-2013057570 A2 | 4/2013 |
| WO | WO-2013058496 A1 | 4/2013 |
| WO | WO-2013059805 A1 | 4/2013 |
| WO | WO-2013061161 A2 | 5/2013 |
| WO | WO-2013070617 A1 | 5/2013 |
| WO | WO-2013072395 A1 | 5/2013 |
| WO | WO-2013077851 A1 | 5/2013 |
| WO | WO-2013082308 A1 | 6/2013 |
| WO | WO-2013083710 A1 | 6/2013 |
| WO | WO-2013084059 A1 | 6/2013 |
| WO | WO-2013093877 A2 | 6/2013 |
| WO | WO-2013103537 A1 | 7/2013 |
| WO | WO-2013119231 A1 | 8/2013 |
| WO | WO-2013128276 A2 | 9/2013 |
| WO | WO-2013128447 A1 | 9/2013 |
| WO | WO-2013136078 A1 | 9/2013 |
| WO | WO-2013138118 A1 | 9/2013 |
| WO | WO-2013151638 A1 | 10/2013 |
| WO | WO-2013155430 A1 | 10/2013 |
| WO | WO-2013158810 A1 | 10/2013 |
| WO | WO-2013158814 A1 | 10/2013 |
| WO | WO-2013170052 A1 | 11/2013 |
| WO | WO-2013171146 A1 | 11/2013 |
| WO | WO-2013175511 A1 | 11/2013 |
| WO | WO-2014001268 A1 | 1/2014 |
| WO | WO-2014001904 A1 | 1/2014 |
| WO | WO-2014001905 A1 | 1/2014 |
| WO | WO-2014006004 A1 | 1/2014 |
| WO | WO-2014011830 A1 | 1/2014 |
| WO | WO-2014025638 A1 | 2/2014 |
| WO | WO-2014045305 A1 | 3/2014 |
| WO | WO-2014047731 A1 | 4/2014 |
| WO | WO-2014059512 A1 | 4/2014 |
| WO | WO-2015023675 A2 | 2/2015 |
| WO | WO-2015023704 A1 | 2/2015 |

OTHER PUBLICATIONS

"Poloxamer" from Wikipedia, the free encyclopedia—4 Pages.

Bartholomaus et al., "New Abuse Deterrent Formulation (ADF) Technology for Immediate-Release Opioids". Drug Development & Delivery, 2013, vol. 13, No. 8, pp. 76-81.

Benziger et al., "Differential Effects of Food on the Bioavailability of Controllied-Release Oxycodone Tablets and Immediate-Release Oxycodone Solution", Journal of Pharmaceutical Sciences, vol. 85, No. 4, pp. 407-410.

Borini et al., "Hot melt granulation of coarse pharmaceutical powders in a spouted bed", Powder Technology, 2009, vol. 189, No. 3, pp. 520-527.

Dahl et al., "Mechanisms to control drug release from pellets coated with a silicone elastomer aqueous dispersion", Pharmaceutical Research, 1992, vol. 9, No. 3, pp. 398-405.

Djuris et al., "Application of quality by design concepts in the development of fluidized bed granulation and tableting processes", Journal of Pharmaceutical Sciences, 2013, vol. 102, No. 6, pp. 1869-1882.

Gazzaniga et al., "A novel injection-molded capsular device for oral pulsatile delivery based on swellable/erodible polymers", AAPS PharmSciTech, 2011, vol. 12, No. 1, pp. 295-303.

Gohel et al., "Fabrication and Evaluation of Bi-layer Tablet Containing Conventional Paracetamol and Modified Release Diclofenac Sodium", Indian J. Pharm Sci., 2010, vol. 72, No. 2, pp. 191-196.

Gosai et al., "Bioequivalence of oxycodone hydrochloride extended release tablets to marketed reference products OxyContin® in Canada and US", Int J Clin Pharmacol Ther., 2013, vol. 51, No. 11, pp. 895-907.

Harris, et al., "Abuse potential, pharmacokinetics, pharmacodynamics, and safety of intranasally administered crushed oxycodone HCl abuse-deterrent controlled-release tablets in recreational opioid users", Journal of Clinical Pharmacology, 2014, vol. 54, No. 4, pp. 468-477.

International Search and Written Opinion based on International Application No. PCT/US2014/70942, dated Mar. 18, 2015—10 Pages.

International Search Report and Written Opinion based on International Application No. PCT/US2014/070949, dated Apr. 15, 2015—10 Pages.

International Search Report for International Application No. PCT/US2015/039336; Filing Date Jul. 7, 2015.

International Search Report for International Application No. PCT/US14/50737; International Filing Date Aug. 12, 2014.

(56) References Cited

OTHER PUBLICATIONS

King, "Tablets, Capsules, and Pills", Remington's Pharmaceutical Science, Mack Publishing Company, 15th Edition, 1975, pp. 1576-1607.

MP Biomedicals. Lecithin Melting Point Properties. Retrieved Feb. 2016.

Sako et al., "Relationship between gelation rate of controlled-release acetaminophen tablets containing polyethylene bride and colonic drug release in dogs", Pharmaceutical Research, 1996, vol. 13, No. 4, pp. 594-598.

Sako, et al., "Influence of water soluble fillers in hydroxypropylmethylcellulose matrices on in vitro and in vivo drug release", Journal of Controlled Release, 2002, vol. 81, No. 1-2, pp. 165-172.

Soininen et al., "Dissolution rate of different kinds of granulated micronized paracetamol with adjuvant incorporated either inter- or intragranularly", Acta Pharmaceutica Fennica, 1981, vol. 90, No. 2, pp. 153-162.

Soininen et al., "Effect of polyethylene glycol 20000 on bioavailability of micronized and crystalline paracetamol", Acta Pharmaceutica Fennica, 1981, vol. 90, vol. 4, pp. 381-386.

Stambaugh et al., "Double-blind, randomized comparison of the analgesic and pharmacokinetic profiles of controlled- and immediate-release oral oxycodone in cancer pain patients", 2001, vol. 41, No. 5, pp. 500-506.

Sunshine et al., "Analgesic Efficacy of Controlled-Release Oxycodone in Postoperative Pain", Journal of Clinical Pharmacology, 1996, vol. 36, No. 7, pp. 595-603.

Third Party Observation dated Sep. 8, 2015 for International Application No. PCT/US2014/050737.

Treffer, Daniel, et al., "Pellet Production by Hot Melt Extrusion and Die Face Pelletising", Pharmaceutical Solid State Research Cluster, May 7, 2013, pp. 1-5.

Upadhye et al., "Polyethylene Oxide and Ethylcellulose for Tamper Resistance and Controlled Drug Delivery", Melt Extrusion, AAPS Advances in the Pharmaceutical Sciences Series, 2013, vol. 9, pp. 145-158.

\* cited by examiner

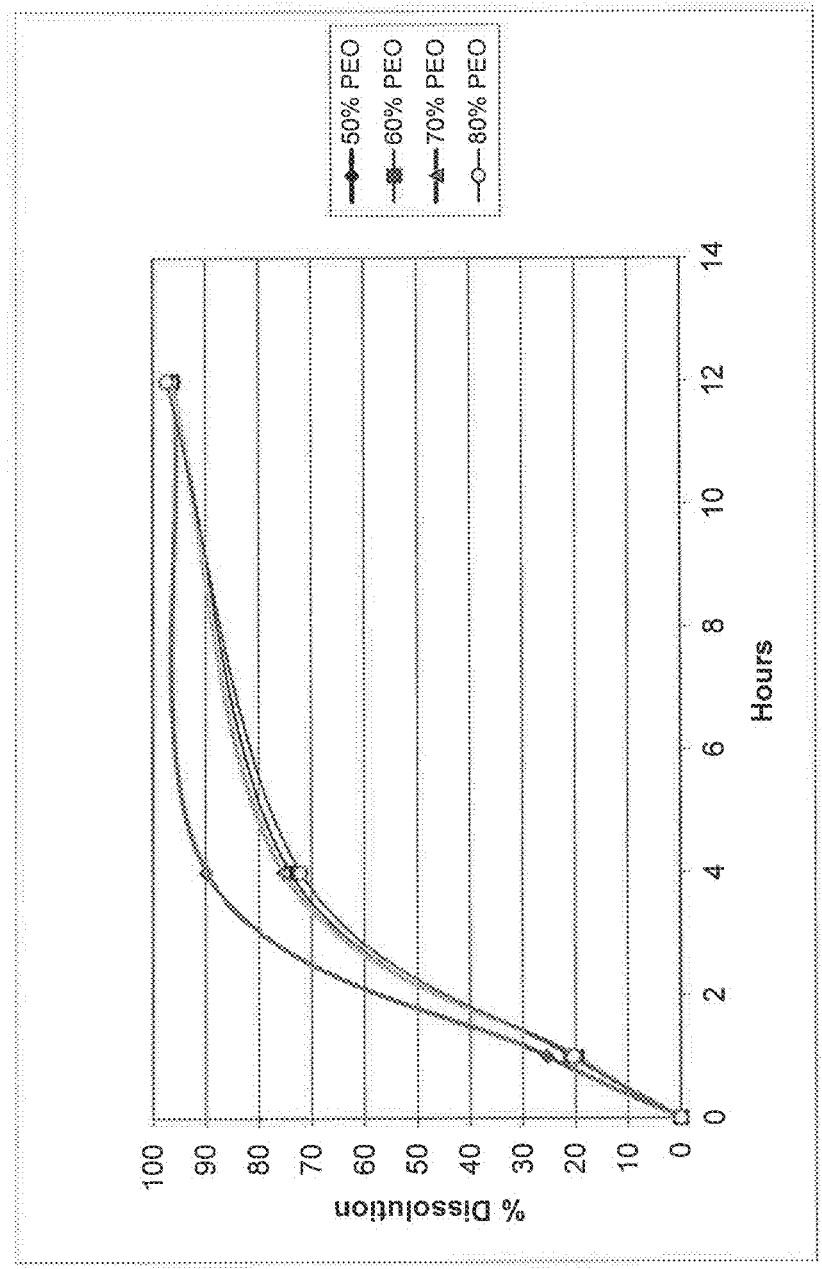

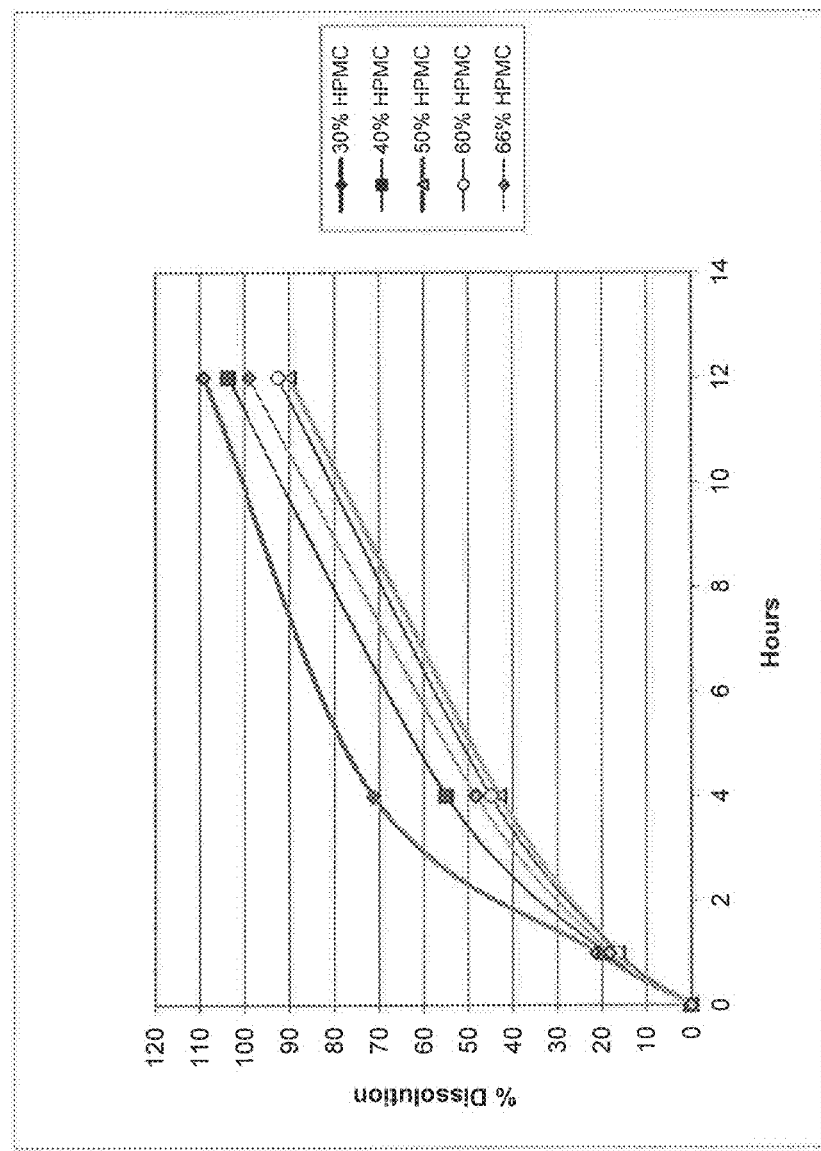

Figure 8

| 200mg Pills | Dosage (mg) | | | | | | | |
|---|---|---|---|---|---|---|---|---|
| Excipient | 10 | 15 | 20 | 30 | 40 | 50 | 60 | 80 |
| | Wt % | Wt % | Wt % | Wt % | Wt % | Wt % | Wt % | Wt % |
| Oxycodone HCl | 5.00% | 7.50% | 10.00% | 15.00% | 20.00% | 25.00% | 30.00% | 40.00% |
| Polyethylene Oxide 100,000 g/mol | 25.00% | 25.00% | 25.00% | 25.00% | 25.00% | 25.00% | 25.00% | 25.00% |
| Polyvinyl Acetate / Polyvinyl Pyrrolidone | 55.42% | 53.96% | 52.50% | 49.58% | 46.67% | 39.47% | 40.83% | 33.00% |
| Polyethylene Glycol 8,000 g/mol | 14.58% | 13.54% | 12.50% | 10.42% | 8.33% | 10.53% | 4.17% | 2.00% |

| 200mg Pills | Dosage (mg) | | | | | | | |
|---|---|---|---|---|---|---|---|---|
| Excipient | 10 | 15 | 20 | 30 | 40 | 50 | 60 | 80 |
| | Wt % | Wt % | Wt % | Wt % | Wt % | Wt % | Wt % | Wt % |
| Oxycodone HCl | 5.00% | 7.50% | 10.00% | 15.00% | 20.00% | 25.00% | 30.00% | 40.00% |
| Polyethylene Oxide 100,000 g/mol | 25.00% | 25.00% | 25.00% | 25.00% | 25.00% | 25.00% | 25.00% | 25.00% |
| Polyvinyl Acetate | 44.33% | 43.17% | 42.00% | 39.67% | 37.33% | 31.58% | 32.67% | 26.40% |
| Polyvinyl Pyrrolidone | 10.53% | 10.25% | 9.98% | 9.42% | 8.87% | 7.50% | 7.76% | 6.27% |
| Sodium Laurel Sulfate | 0.44% | 0.43% | 0.42% | 0.40% | 0.37% | 0.32% | 0.33% | 0.26% |
| Silica | 0.11% | 0.11% | 0.11% | 0.10% | 0.09% | 0.08% | 0.08% | 0.07% |
| Polyethylene Glycol 8,000 g/mol | 14.58% | 13.54% | 12.50% | 10.42% | 8.33% | 10.53% | 4.17% | 2.00% |

Figure 9

| 200mg Pills | 5 | 7.5 | 10 | 15 | 20 | 30 | 40 |
|---|---|---|---|---|---|---|---|
| | | | | Dosage (mg) | | | |
| Excipient | Wt % | Wt % | Wt % | Wt % | Wt % | Wt % | Wt % |
| Oxycodone HCl | 2.50% | 3.75% | 5.00% | 7.50% | 10.00% | 15.00% | 20.00% |
| Polyethylene Oxide 100,000 g/mol | 25.00% | 25.00% | 25.00% | 25.00% | 25.00% | 25.00% | 25.00% |
| Polyvinyl Acetate / Polyvinyl Pyrrolidone | 48.75% | 48.13% | 47.50% | 46.25% | 45.00% | 42.50% | 40.00% |
| Polyethylene Glycol 8,000 g/mol | 23.75% | 23.13% | 22.50% | 21.25% | 20.00% | 17.50% | 15.00% |

| 200mg Pills | 5 | 7.5 | 10 | 15 | 20 | 30 | 40 |
|---|---|---|---|---|---|---|---|
| | | | | Dosage (mg) | | | |
| Excipient | Wt % | Wt % | Wt % | Wt % | Wt % | Wt % | Wt % |
| Oxycodone HCl | 2.50% | 3.75% | 5.00% | 7.50% | 10.00% | 15.00% | 20.00% |
| Polyethylene Oxide 100,000 g/mol | 25.00% | 25.00% | 25.00% | 25.00% | 25.00% | 25.00% | 25.00% |
| Polyvinyl Acetate | 39.00% | 38.50% | 38.00% | 37.00% | 36.00% | 34.00% | 32.00% |
| Polyvinyl Pyrrolidone | 9.26% | 9.14% | 9.03% | 8.79% | 8.55% | 8.08% | 7.60% |
| Sodium Laurel Sulfate | 0.39% | 0.39% | 0.38% | 0.37% | 0.36% | 0.34% | 0.32% |
| Silica | 0.10% | 0.10% | 0.10% | 0.09% | 0.09% | 0.09% | 0.08% |
| Polyethylene Glycol 8,000 g/mol | 23.75% | 23.13% | 22.50% | 21.25% | 20.00% | 17.50% | 15.00% |

Figure 10

| 200mg Pills | | | | | | | | | |
|---|---|---|---|---|---|---|---|---|---|
| | | Dosage (mg) | | | | | | | |
| Excipient | 10 | 15 | 20 | 30 | 40 | 50 | 60 | 80 |
| | Wt % | Wt % | Wt % | Wt % | Wt % | Wt % | Wt % | Wt % |
| Oxycodone HCl | 5.00% | 7.50% | 10.00% | 15.00% | 20.00% | 25.00% | 30.00% | 40.00% |
| Polyethylene Oxide 300,000 g/mol | 29.00% | 29.00% | 29.00% | 29.00% | 29.00% | 29.00% | 29.00% | 29.00% |
| Hypromellose, K100M | 38.00% | 37.00% | 36.00% | 34.00% | 32.00% | 27.00% | 28.00% | 24.00% |
| Polyethylene Glycol 8,000 g/mol | 28.00% | 26.50% | 25.00% | 22.00% | 19.00% | 19.00% | 13.00% | 7.00% |

| 200mg Pills | | | | | | | | |
|---|---|---|---|---|---|---|---|---|
| | | Dosage (mg) | | | | | | |
| Excipient | 5 | 7.5 | 10 | 15 | 20 | 30 | 40 |
| | Wt % | Wt % | Wt % | Wt % | Wt % | Wt % | Wt % |
| Oxycodone HCl | 2.50% | 3.75% | 5.00% | 7.50% | 10.00% | 15.00% | 20.00% |
| Polyethylene Oxide 300,000 g/mol | 29.00% | 29.00% | 29.00% | 29.00% | 29.00% | 29.00% | 29.00% |
| Hypromellose, K100M | 35.10% | 34.65% | 34.20% | 33.30% | 32.40% | 30.60% | 28.80% |
| Polyethylene Glycol 8,000 g/mol | 33.40% | 32.60% | 31.80% | 30.20% | 28.60% | 25.40% | 22.20% |

Figure 11

| 10mg Experiment | PEO Grade | PEO % | PVAc/PVP % | PEG 8000 | API % | 1 Hour Average % | 4 Hour Average % | 12 Hour Average % | ADF % >500μm |
|---|---|---|---|---|---|---|---|---|---|
| 1 | N/A | 0 | 50 | 45 | 5 | 35.97 F | 66.10 F | 95.9 | 40 F |
| 2 | N/A | 0 | 60 | 35 | 5 | 31.30 F | 58.96 | 96.78 | 45 F |
| 3 | 100K | 15 | 50 | 30 | 5 | 29.56 F | 56.23 | 93.44 | 75 |
| 4 | 100K | 25 | 50 | 20 | 5 | 28.83 F | 62.67 | 95.07 | 79 |
| 5 | 100K | 15 | 60 | 20 | 5 | 24.48 | 54.17 | 88.37 | 73 |
| 5 (Range) | | 13-17 | 58-62 | 18-22 | | | | | |
| 6 | 100K | 25 | 60 | 10 | 5 | 19.69 | 40.42 F | 66.77 F | 95 |
| 7 | 100K | 25 | 55 | 15 | 5 | 23.13 | 44.49 | 71.92 F | 93 |
| 8 | 100K | 25 | 53 | 18 | 5 | 32.24 F | 61.75 | 83.16 | 85 |

| 80mg | PEO Grade | PEO % | PVAc/PVP % | PEG 8000 | API % | 1 Hour Average % | 4 Hour Average % | 12 Hour Average % | ADF % >500μm |
|---|---|---|---|---|---|---|---|---|---|
| 9 | 100K | 9.47 | 37.89 | 12.64 | 40 | 27.44 | 57.57 | 91.14 | 61 |
| 9 (Range) | | 8-12 | 36-39 | 10-14 | | | | | |
| 10 | 100K | 15 | 37.89 | 7.11 | 40 | 24.47 | 48.41 | 72.91 F | 71 |
| 11 | 100K | 25 | 33 | 2 | 40 | 27.67 | 57.8 | 86.9 | 79 |
| 11 (Range) | | 23-27 | 31-35 | 1-3 | | | | | |
| 12 | 100K | 25 | 35 | 0 | 40 | 38.17 F | 70.91 F | 92.06 | 75 |

| 10mg Experiment | PEO Grade | PEO % | HPMC 100K % | PEG 8000 | API % | 1 Hour Average % | 4 Hour Average % | 12 Hour Average % | ADF % >500μm |
|---|---|---|---|---|---|---|---|---|---|
| 13 | 300K | 60 | 10 | 25 | 5 | 20.83 | 74.00 F | 96.43 | 100 |
| 14 | 300K | 70 | 10 | 15 | 5 | 19.8 | 75.30 F | 96.46 | 98 |
| 15 | 300K | 80 | 10 | 5 | 5 | 20.35 | 72.08 F | 97.44 | 99 |
| 16 | 100K | 60 | 25 | 10 | 5 | 62.96 F | 102.15 F | 100.38 | N/A |
| 17 | 100K | 60 | 30 | 5 | 5 | 44.00 F | 103.07 F | 101.57 | N/A |
| 18 | 100K | 70 | 25 | 0 | 5 | 45.82 F | 95.86 F | 94.15 | N/A |
| 19 | 300K | 29 | 30 | 36 | 5 | 21.14 | 71.36 F | 109.14 | 92 |
| 20 | 300K | 29 | 40 | 26 | 5 | 19.39 | 54.95 | 103.7 | 98 |
| 20 (Range) | | 27-31 | 38-42 | 24-28 | | | | | |
| 21 | 300K | 29 | 50 | 16 | 5 | 16.40 F | 42.95 F | 90.04 | 98 |
| 22 | 300K | 29 | 60 | 6 | 5 | 16.51 F | 44.96 | 92.56 | 96 |
| 23 | 300K | 29 | 37 | 29 | 5 | 25.83 | 64.46 | 93.2 | 96 |
| 23 (Range) | | 27-31 | 35-39 | 27-31 | | | | | |

| 80mg | PEO Grade | PEO % | HPMC 100K % | PEG 8000 | API % | 1 Hour Average % | 4 Hour Average % | 12 Hour Average % | ADF % >500μm |
|---|---|---|---|---|---|---|---|---|---|
| 24 | 300K | 29 | 25 | 6 | 40 | 18.02 F | 53.38 F | 102.66 | 93 |
| 25 | 300K | 29 | 31 | 0 | 40 | 19.13 F | 50.39 F | 95.15 | 95 |
| 26 | 300K | 29 | 23 | 8 | 40 | 27.20 F | 72.60 F | 93.68 | 93 |

FIG. 15
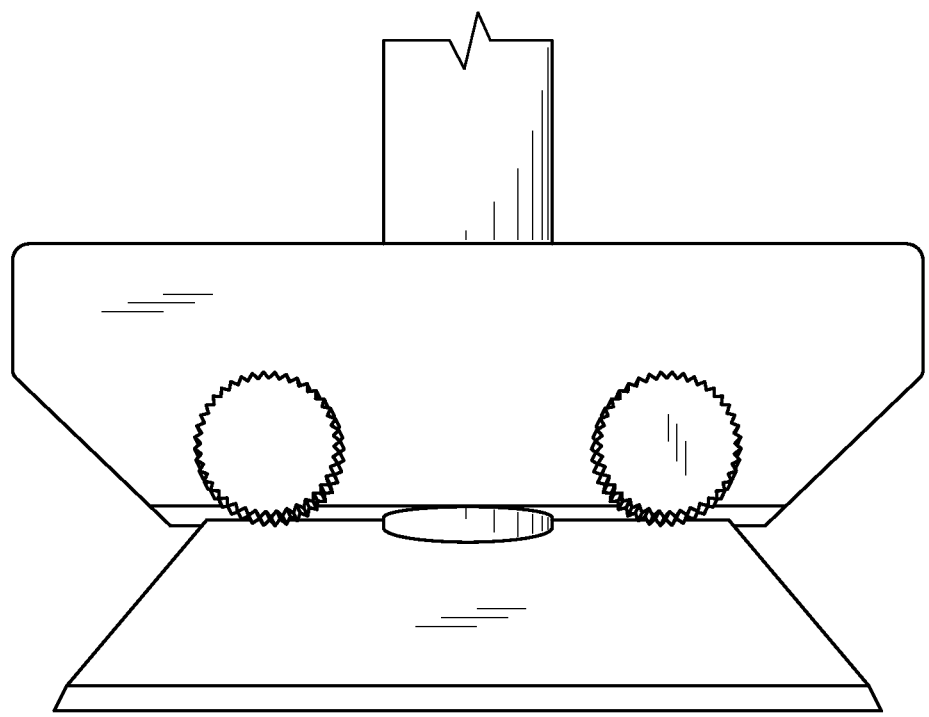
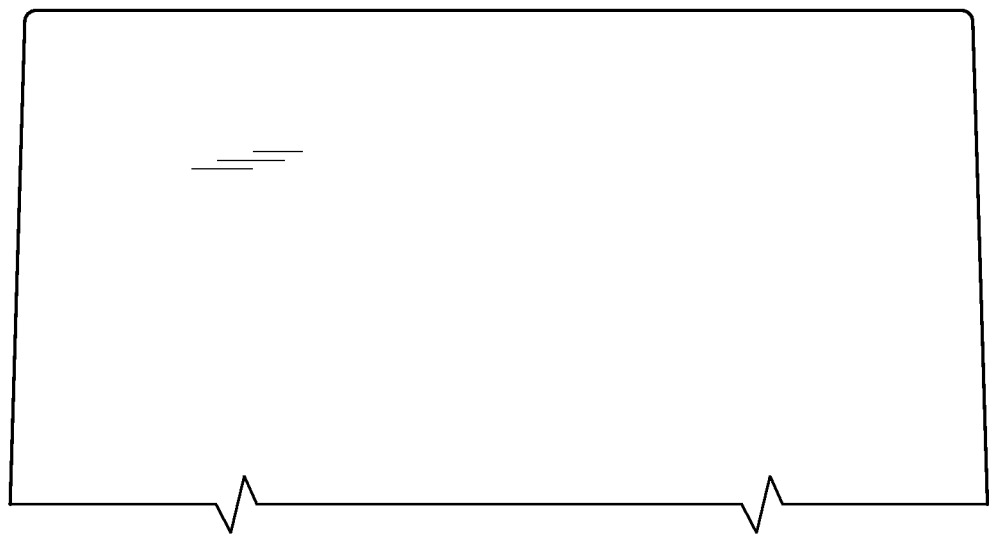

Figure 16

Cutting Force - Razor Blade

| Replicate | PMRS ER 10mg | PMRS ER 80mg | Opana® ER 5mg | Opana® ER 40mg | OxyContin® 10mg | OxyContin® 40mg | OxyContin® 60mg | OxyContin® 80mg |
|---|---|---|---|---|---|---|---|---|
| 1 | 77 | 90 | 133 | 119 | 55 | 37 | 46 | 46 |
| 2 | 79 | 86 | 135 | 120 | 50 | 52 | 47 | 49 |
| 3 | 85 | 87 | 133 | 136 | 42 | 40 | 45 | 52 |
| 4 | 64 | 86 | 119 | 127 | 42 | 44 | 43 | 46 |
| 5 | 85 | 76 | 133 | 138 | 43 | 43 | 44 | 53 |
| 6 | 83 | 90 | 131 | 129 | 44 | 43 | 45 | 45 |
| 7 | 80 | 93 | 129 | 141 | 47 | 44 | 46 | 45 |
| 8 | 79 | 81 | 127 | 142 | 46 | 39 | 45 | 48 |
| 9 | 82 | 89 | 116 | 135 | 40 | 44 | 42 | 48 |
| 10 | 81 | 89 | 117 | 125 | 41 | 43 | 53 | 47 |
| Minimum | 64 | 76 | 116 | 119 | 40 | 37 | 42 | 45 |
| Maximum | 85 | 93 | 135 | 142 | 55 | 52 | 53 | 53 |
| Average | 79 | 87 | 127 | 131 | 45 | 43 | 46 | 48 |
| %RSD | 7.7 | 5.7 | 5.7 | 6.6 | 12.2 | 9.4 | 6.9 | 5.7 |

Cutting Force - Fracture Wedge Set

| Replicate | PMRS ER 10mg | PMRS ER 80mg | Opana® ER 5mg | Opana® ER 40mg | OxyContin® 10mg | OxyContin® 40mg | OxyContin® 60mg | OxyContin® 80mg |
|---|---|---|---|---|---|---|---|---|
| 1 | 110 | 127 | 156 | 132 | 144 | 92 | 108 | 97 |
| 2 | 109 | 114 | 156 | 142 | 153 | 84 | 103 | 97 |
| 3 | 115 | 108 | 155 | 143 | 156 | 85 | 104 | 99 |
| 4 | 110 | 124 | 145 | 138 | 157 | 92 | 102 | 96 |
| 5 | 104 | 112 | 161 | 142 | 160 | 98 | 111 | 91 |
| 6 | 105 | 110 | 151 | 137 | 154 | 92 | 107 | 97 |
| 7 | 110 | 113 | 156 | 143 | 154 | 100 | 100 | 90 |
| 8 | 96 | 112 | 158 | 144 | 140 | 95 | 104 | 92 |
| 9 | 103 | 118 | 163 | 150 | 148 | 93 | 102 | 91 |
| 10 | 92 | 108 | 158 | 144 | 127 | 91 | 104 | 92 |
| Minimum | 92 | 108 | 145 | 132 | 127 | 85 | 100 | 90 |
| Maximum | 115 | 127 | 163 | 150 | 160 | 100 | 111 | 99 |
| Average | 105 | 115 | 156 | 141 | 149 | 93 | 104 | 95 |
| %RSD | 6.7 | 5.7 | 3.3 | 3.5 | 6.6 | 4.4 | 3.2 | 3.4 |

Figure 17

Particle Size Analysis - GRINDOMIX GM200

| Location | Replicate | Sample Name | | | | | | |
|---|---|---|---|---|---|---|---|---|
| | | PMRS ER 10mg | PMRS ER 80mg | Opana® ER 5mg | Opana® ER 40mg | OxyContin® 10mg | OxyContin® 40mg | OxyContin® 80mg | OxyContin® 80mg |
| Pan (<500µm) % | 1 | 5,116 | 7,283 | -1,728 | 3,479 | 23,075 | 11,918 | 21,636 | 25,919 |
| | 2 | 5,430 | 9,525 | 8,614 | 3,376 | 6,997 | 12,963 | 18,177 | 24,829 |
| | 3 | 5,914 | 7,401 | 0,600 | 3,320 | 18,485 | 23,140 | 17,785 | 23,150 |
| | Minimum | 5,914 | 7,283 | -1,728 | 3,320 | 6,997 | 11,918 | 17,785 | 23,150 |
| | Maximum | 5,430 | 9,525 | 8,614 | 3,479 | 23,075 | 23,140 | 21,636 | 25,919 |
| | Average | 1,544 | 8,070 | 2,295 | 3,392 | 16,185 | 16,340 | 19,198 | 24,632 |
| | %RSD | 418,385 | 15,633 | 241,364 | 2,375 | 51,168 | 36,578 | 11,043 | 5,662 |
| 35 Mesh (≥500µm) % | 1 | 94,884 | 92,717 | 101,728 | 96,521 | 76,925 | 88,082 | 78,364 | 74,081 |
| | 2 | 94,570 | 90,475 | 91,386 | 96,624 | 93,003 | 86,037 | 81,827 | 75,172 |
| | 3 | 105,914 | 92,589 | 100,600 | 96,680 | 81,515 | 76,860 | 82,215 | 76,850 |
| | Minimum | 94,570 | 90,475 | 91,386 | 96,521 | 76,925 | 76,860 | 78,364 | 74,081 |
| | Maximum | 105,914 | 92,717 | 101,728 | 96,680 | 93,003 | 88,082 | 82,215 | 76,850 |
| | Average | 98,456 | 91,930 | 97,905 | 96,608 | 83,815 | 83,660 | 80,802 | 75,368 |
| | %RSD | 6,562 | 1,372 | 5,670 | 0,083 | 9,881 | 7,144 | 2,624 | 1,851 |

Particle Size Analysis - Mr. Coffee® Grinder

| Location | Replicate | Sample Name | | | | | | |
|---|---|---|---|---|---|---|---|---|
| | | PMRS ER 10mg | PMRS ER 80mg | Opana® ER 5mg | Opana® ER 40mg | OxyContin® 10mg | OxyContin® 40mg | OxyContin® 60mg | OxyContin® 80mg |
| Pan (<500µm) % | 1 | 16,536 | 21,531 | 15,289 | 3,092 | 19,223 | 38,264 | 40,970 | 44,932 |
| | 2 | 17,891 | 26,499 | 11,785 | 15,311 | 22,266 | 41,150 | 37,439 | 45,045 |
| | 3 | 5,243 | 16,439 | 4,725 | 14,196 | 29,219 | 36,318 | 47,452 | 35,878 |
| | Minimum | 5,243 | 16,439 | 4,725 | 3,092 | 19,223 | 36,318 | 37,439 | 35,878 |
| | Maximum | 17,891 | 26,499 | 15,289 | 15,311 | 29,219 | 41,150 | 47,452 | 45,045 |
| | Average | 13,223 | 21,496 | 10,599 | 10,867 | 23,569 | 38,577 | 41,954 | 41,952 |
| | %RSD | 52,518 | 23,401 | 50,765 | 62,171 | 21,739 | 6,303 | 12,106 | 12,538 |
| 35 Mesh (≥500µm) % | 1 | 83,464 | 78,449 | 84,711 | 96,908 | 80,777 | 61,736 | 59,030 | 55,068 |
| | 2 | 82,109 | 73,501 | 86,215 | 84,689 | 77,734 | 58,850 | 62,561 | 54,955 |
| | 3 | 94,757 | 83,561 | 95,275 | 85,804 | 70,781 | 63,682 | 52,548 | 64,122 |
| | Minimum | 82,109 | 73,501 | 84,711 | 84,689 | 70,781 | 58,850 | 52,548 | 54,955 |
| | Maximum | 94,757 | 83,561 | 95,275 | 96,908 | 80,777 | 63,682 | 62,561 | 64,122 |
| | Average | 86,777 | 78,504 | 89,401 | 89,133 | 76,431 | 61,423 | 58,046 | 58,048 |
| | %RSD | 8,003 | 6,408 | 6,019 | 7,580 | 6,704 | 3,959 | 8,750 | 9,061 |

EXTRUDED EXTENDED RELEASE ABUSE DETERRENT PILL

CROSS-REFERENCE TO RELATED APPLICATIONS

This application is a continuation of U.S. application Ser. No. 14/574,005 filed Dec. 17, 2014, which is a continuation-in-part of U.S. application Ser. No. 14/457,714 filed Aug. 12, 2014, which claims priority to U.S. Provisional Application No. 61/980,254 filed Apr. 16, 2014, 61/980,259 filed Apr. 16, 2014, 61/917,074 filed Dec. 17, 2013 and 61/917,120 filed Dec. 17, 2013, each of which are incorporated herein by reference in their entirety.

FIELD OF THE TECHNOLOGY

The present disclosure relates to an abuse deterrent pill prepared using, e.g., a hot melt extrusion process and a forming unit. The pill exhibits an extended release profile of the active substance, and contains at least one abuse deterrent mechanism to reduce abuse by non-oral administration routes, e.g. intranasal and/or intravenous. The extrusion process and forming unit are designed to efficiently prepare the abuse deterrent pill under conditions that reduce, or substantially eliminate, degradation of the active substance.

BACKGROUND

FDA-approved drugs are provided in many different forms based on the type of active substance, the indication treated and the preferred route of administration. These forms include enteral formulations (e.g., tablets, capsules or pills), parenteral formulations (e.g., injectable formulations such as intravenous, subcutaneous, intramuscular and intraarticular), liquid formulations (e.g., elixirs), lyophilized formulations and topical formulations. A majority of the FDA-approved drugs are currently available in enteral form, as either a tablet or capsule.

The production of pharmaceutical drugs in pill form by hot melt extrusion is relatively uncommon. While the idea of dissolving drugs in polymers and using extrusion to produce a pill has been known for decades, only a handful of FDA-approved drugs are extruded. Recently, extrusion techniques have been investigated for preparing abuse deterrent formulations. For example, U.S. Pat. No. 7,776,314 (assigned to Grunenthal, GmbH) is directed to abuse deterrent dosage systems. These systems contain only viscosity increasing agents to protect against abuse and do not teach specific combinations of matrix agents and controlled release agents. U.S. Pat. No. 8,101,630 (assigned to Acura Pharmaceuticals, Inc.) is directed to extended release opioid abuse deterrent compositions. The compositions contain high molecular weight gel forming polymers. U.S. Pat. No. 8,337,888 (assigned to Purdue Pharma L.P.) is directed to a pharmaceutical formulation containing a gelling agent. The formulations teaching polyethylene oxide (PEO) based matrix agents are osmotic dosage forms comprising a bilayer core, a delivery layer and semipermeable wall. U.S. 2012/065220 (assigned to Grunenthal, GmbH) is directed to a tamper resistant dosage form having an anionic polymer. The dosage form requires the use of an ethylenically unsaturated monomer bearing an anionic functional group to improve the mechanical properties of the dosage form.

SUMMARY

The present disclosure relates to an abuse deterrent pill prepared, e.g., using a hot melt extrusion process and a forming unit. The formulation contains an active substance susceptible to abuse and at least one abuse deterrent mechanism to reduce abuse by non-oral administration routes (e.g., intranasal and/or intravenous). The abuse deterrent pill is designed for extended release of the active substance upon oral administration. In one embodiment, the method of preparing the pill utilizes a hot melt extrusion process coupled with an in-line forming unit which eliminates the need for traditional extrusion processing steps, such as chopping the extrudate and molding the cut extrudate into a final form. The hot melt extrusion process and forming unit are operated under conditions that reduce, or substantially eliminate degradation of the active substance.

In one embodiment, the present disclosure relates to an oral, extended release, abuse deterrent dosage formulation having an active substance susceptible to abuse; a matrix agent, wherein the matrix agent has an average molecular weight between about 50K Daltons and 1M Daltons; a controlled release agent; and optionally, a plasticizer, a dye, or both, wherein the active substance susceptible to abuse has an extended release profile, and wherein the formulation includes a physical barrier to reduce abuse. In some embodiments, the matrix agent is PEO and the average molecular weight may range from about 50K Daltons to about 1M Daltons, or from about 50K Daltons to about 350K Daltons, or from about 250K Daltons to about 350K Daltons, or from about 550K Daltons to about 650 Daltons.

The formulation can contain a controlled release agent. In some embodiments, the controlled release agent is polyvinyl acetate (PVAc), polyvinylpyrrolidone (PVP), hydroxypropyl methylcellulose (HPMC), or a combination thereof. The amounts of controlled release agent, and matrix agent, in the formulation are designed to produce a formulation wherein the active substance susceptible to abuse has an extended release profile, and the formulation includes a physical barrier to reduce abuse.

BRIEF DESCRIPTION OF THE DRAWINGS

FIG. 6 shows the dissolution profiles for exemplary formulations containing different wt % amounts of 300K Dalton PEO (e.g., 50-80 wt %).

FIG. 7 shows the dissolution profiles for exemplary formulations containing different wt % amounts of HPMC (e.g., 30-66 wt %).

FIG. 8 shows exemplary formulations containing 100K Dalton PEO.

FIG. 9 shows exemplary formulations containing 100K Dalton PEO.

FIG. 10 shows exemplary formulations containing 300K Dalton PEO.

FIG. 11 shows exemplary formulations related to the present disclosure and their dissolution profiles and abuse deterrent properties.

FIG. 15 shows equipment capable of executing a "cutting force" analysis including a razor blade attachment.

FIG. 16 shows cutting force data tables for the razor blade and the fracture wedge attachments.

FIG. 17 shows post grinding particle size analysis results for exemplary formulations and commercially available products.

DETAILED DESCRIPTION

Figure 1:
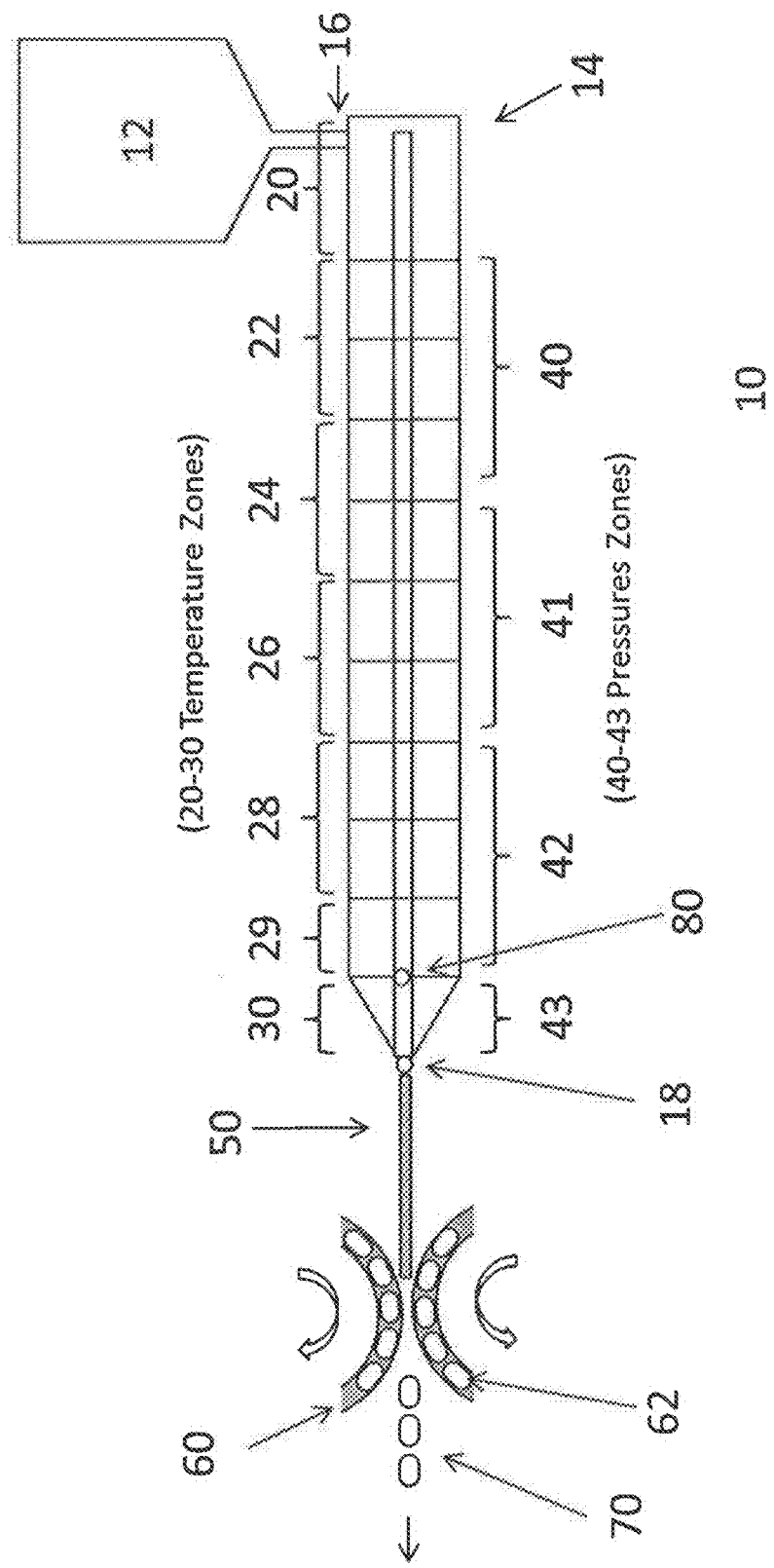
FIG. 1 shows an embodiment of the extruder (14) and forming unit (60). The extruder has multiple temperature zones (e.g., 20-30) and pressure zones (e.g., 20, 40-43) to control the formation of a uniform extrudate under conditions that reduce, or substantially eliminate, degradation of the active substance.

Abuse of prescription drugs, particularly opioids, is a serious and growing public health concern. To address this concern, new formulations are being developed that contain abuse-deterrent properties. Abuse deterrent properties include properties that make product manipulation more difficult or make abuse of the manipulated product less attractive or rewarding.

Recently the FDA issued a draft guidance for industry related to formulations having abuse deterrent properties. *Guidance for Industry: Abuse-Deterrent Opioids—Evaluation and Labeling*, U.S. Department of Health and Human Services, FDA, CDER, January 2013, the entire contents of which are incorporated herein by reference. These guidelines separate abuse deterrent formulations into six categories, including: physical/chemical barriers, agonist/antagonist combinations, aversion, delivery system, prodrug, or a combination of the aforementioned. As described by the FDA guidance, the categories are:

Physical/Chemical barriers—Physical barriers can prevent chewing, pulverizing, cutting, grating, or grinding. Chemical barriers can resist extraction of the opioid using common solvents like water, alcohol, or other organic solvents. Physical and chemical barriers can change the physical form of an oral drug rendering it less amenable to abuse.

Agonist/Antagonist combinations—An opioid antagonist can be added to interfere with, reduce, or defeat the euphoria associated with abuse. The antagonist can be sequestered and released only upon manipulation of the product. For example, a drug product may be formulated such that the substance that acts as an antagonist is not clinically active when the product is swallowed but becomes active if the product is crushed and injected or snorted.

Aversion—Substances can be combined to produce an unpleasant effect if the dosage form is manipulated prior to ingestion or a higher dosage than directed is used.

Delivery System (including depot injectable formulations and implants)—Certain drug release designs or the method of drug delivery can offer resistance to abuse. For example, a sustained-release depot injectable formulation that is administered intramuscularly or a subcutaneous implant can be more difficult to manipulate.

Prodrug—A prodrug that lacks opioid activity until transformed in the gastrointestinal tract can be unattractive for intravenous injection or intranasal routes of abuse.

Combination—Two or more of the above methods can be combined to deter abuse.

An opioid analgesic submitted for abuse deterrent formulation (ADF) labeling must show conformance to one or more of these categories. The present disclosure relates to an abuse deterrent pill for oral administration, which provides extended release of an active pharmaceutical substance and conforms to one or more of these categories. In one embodiment, the abuse deterrent formulation of the present disclosure conforms to at least one of the six FDA categories. In another embodiment, the abuse deterrent formulation of the present disclosure conforms to at least two of the six FDA categories. In another embodiment, the abuse deterrent formulation of the present disclosure conforms to at least three of the six FDA categories. In another embodiment, the abuse deterrent formulation of the present disclosure conforms to at least four of the six FDA categories. In another embodiment, the abuse deterrent formulation of the present disclosure conforms to at least five of the six FDA categories.

For example, an abuse deterrent pill of the present disclosure can reduce abuse by the incorporation of at least one physical barrier. The physical barrier is designed to prevent abuse based on chewing, pulverizing, cutting, grating or grinding. Preferably, the physical barrier prevents or reduces the effectiveness of these methods. As used herein, the phrase "abuse deterrent" means that the active substance cannot readily be separated from the formulation in a form suitable for abuse by such means as, for example, grinding. The abuse deterrent pill of the present disclosure cannot be easily ground, extracted from, or both. Abuse deterrent measures render it difficult to transform the pill into a powder or extract for non-oral administration, such as intranasal or intravenous.

In one embodiment, the present disclosure relates to a directly-formed, extruded oral, extended release, abuse deterrent pill. The pill includes an active substance susceptible to abuse, a matrix agent having an average molecular weight between about 50K Daltons and 350K Daltons, a controlled release agent and optionally a plasticizer, a dye, or both. The pill exhibits an extended release profile of the active substance and includes a physical barrier to reduce abuse. After extrusion, the extrudate is directly formed into the pill without further processing, such as the use of a cutting step.

As used herein, the term "active substance" or "active substance susceptible to abuse" means an opioid or opioid related compound subject to potential abuse. The active substance may include, without limitation, alfentanil, allylprodine, alphaprodine, amphetamine, anileridine, benzylmorphine, bezitramide, buprenorphine, butorphanol, clonitazene, codeine, cyclazocine, desomorphine, dextroamphetamine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levophenacylmorphan, levorphanol, lofentanil, meperidine, meptazinol, metazocine, methadone, metopon, morphine, myrophine, nalbulphine, narceine, nicomorphine, norpipanone, opium, oxycodone, papvretum, pentazocine, phenadoxone, phenazocine, phenomorphan, phenoperidine, piminodine, propiram, propoxyphene, sufentanil, tilidine, and tramadol, and/or pharmaceutically acceptable salts and mixtures thereof. Preferably, the active substance is oxycodone HCl, hydrocodone bitartrate, hydromorphone HCl, morphine sulfate, or methadone HCl. In one embodiment, the formulation of the present disclosure excludes oxymorphone. For example, the formulation of the present disclosure contains at least one active substance susceptible to abuse, provided the active substance is not oxymorphone.

The amount of active substance in the formulation may vary depending on the active substance, stability, release profile and bioavailability. The amount of active substance in the formulation may range from about 1.0 wt % to about 50 wt %. Particularly, the amount of active substance in the formulation may range from about 4 wt % to about 40 wt %. For example, the formulation may be a 200 mg pill having between about 8 mg and about 80 mg of active substance (e.g., oxycodone HCl). In another embodiment, the formulation may be a 500 mg pill having between 15 mg and about 200 mg of active substance (e.g., morphine sulfate)

The dosage form of the present disclosure can be rendered abuse deterrent by incorporating at least one matrix agent in the formulation to increase the strength of the tablet beyond that of conventional dosage forms. The matrix agent increases the dosage form's resistance to physical or mechanical forces, such as pulverizing or grinding. By selecting the appropriate molecular weight grade and the quantity of matrix agent present within a formulation, the strength characteristics of the dosage form can be manipulated in a way to create a wide array of abuse deterrent pills have extended release profiles.

The matrix agent may also render the dosage form abuse deterrent by acting as a gelling or viscosity increasing agent. Upon contact with a solvent (e.g., aqueous or semi-aqueous solution), the dosage form is capable of absorbing the solvent and swelling to form a viscous or semi-viscous substance. The formation of a viscous or semi-viscous substance significantly reduces and/or minimizes the amount of free solvent which can contain an amount of active substance, and which can be drawn into a syringe. The matrix agent can also reduce the overall amount of active substance extractable with the solvent by entrapping the active substance in a gel matrix. Typical matrix agents include pharmaceutically acceptable polymers, typically hydrophilic polymers, such as those that form hydrogels. These properties allow for an oral drug delivery system that satisfies at least one of the categories in the FDA guidance (e.g., "physical and chemical barriers can change the physical form of an oral drug rendering it less amenable to abuse").

The matrix agent may exhibit a high degree of viscosity upon contact with a suitable solvent. The high viscosity can enhance the formation of highly viscous gels when attempts are made to crush and dissolve the contents of a formulation in an aqueous or semi-aqueous vehicle and inject it intravenously. For example, when an abuser crushes and dissolves the formulation in a solvent, a viscous or semi-viscous gel is formed. The increase in the viscosity of the solution discourages the abuser from injecting the gel intravenously or intramuscularly.

In some embodiments, the matrix agent prevents extraction of the active ingredient susceptible to abuse. For example, when a formulation of the present disclosure is introduced to a small volume of aqueous or semi-aqueous solution, the matrix agent forms a viscous solution and/or hydrogel in a relatively short amount of time such that appreciable amounts of active substance are unable to be separated from the dosage form in a solution that can be abused. The formulation can be intact or can be adulterated, e.g., ground or broken up in to pieces. The small volume of water can be 0.1 mL, to 100 mL, particularly 1 mL to 10 mL. The concentration of the formulation in the small volume solution can be 10 mg/mL to 200 mg/mL, particularly 5 mg/mL to 80 mg/mL. In some embodiments, the small volume solution is agitated. In other embodiments, the small volume solution is not agitated. Under both agitated and unagitated conditions, the matrix agent prevents extraction of the active ingredient susceptible to abuse by forming a viscous solution and/or hydrogel.

Without wishing to be bound, it is believed that the when introduced to an aqueous media, the difference in the molecular weight of the matrix agent, e.g. PEO, affects the ability to abuse the dosage form. For example, the inclusion of low MW PEO (e.g., 50K Daltons to 500K, 600K, 700K, 800K, 900K, or 1M Daltons forms a hydrogel quickly and binds up the API when not agitated. The inclusion of higher MW PEO takes longer to form a hydrogel. Typically, the API is more water soluble than the high MW PEO because the API is a much smaller molecule and hydrates much faster than the PEO. As such, in situation where the API is more water soluble than the matrix agent, the API can leach out of the dosage form before a hydrogel forms, making it more easily abused.

Suitable matrix agents are natural or synthetic polymers capable of providing increased resistance to pulverizing or grinding. The matrix agent may be selected from the group consisting of agar, alamic acid, alginic acid, carmellose, carboxymethylcellulose sodium, chitosan, copovidone, dextrin, gelatin, hydroxyethyl cellulose, hydroxypropyl cellulose, hydroxypropyl methylcellulose, methylcellulose derivatives, microcrystalline cellulose, polyacrylic acid, polyalkalene oxide (e.g., polymethylene oxide, polyethylene oxide and polypropylene oxide), polyvinyl alcohol, povidone, propylene glycol alginate, polyvinylcaprolactam-polyvinyl acetate-polyethylene glycol graft co-polymers, pullulan, silicon dioxide, sodium alginate, starch, and vinylpyrrolidone-vinyl acetate copolymers. In one embodiment, the matrix agent is a polyethylene oxide. Polyethylene oxide is a non-ionic, water soluble polymer that is readily available in a wide range of molecular weight grades.

The matrix agent should be capable of ensuring the formation of a solid dosage form by extrusion or by other processes which utilizes force and heat; capable of aiding with extended release of the active substance, and/or capable of preventing abuse via pulverization or small volume extraction. The matrix agent can have a molecular weight of about 50K, 75K, 100K, 125K, 150K, 175K, 200K, 250K, 300K, 350K, 400K, 450K, 500K, 550K, 600K, 650K, 700K, 750K, 800K, 850K, 900K, 950K or 1000K Daltons. These values can also be used to define a range, such as about 75K Daltons to about 175K Daltons. In some embodiments, the formulation of the present disclosure can accomplish these capabilities by using a matrix agent having an appropriate molecular weight (or appropriate average molecular weight), such as between about 50K Daltons and about 650K Daltons. In one embodiment, the matrix agent has a molecular weight between about 50K and about 150K Daltons, or about 100K Daltons. In another embodiment, the matrix agent has a molecular weight between about 250K and about 350K Daltons, or about 300K Daltons. In another embodiment, the matrix agent has a molecular weight between about 550K and about 650K Daltons, or about 600K Daltons.

In one embodiment, the present disclosure relates to an oral, extended release, abuse deterrent dosage formulation having an active substance susceptible to abuse; and a matrix agent, wherein the matrix agent has an average molecular weight between about 50K Daltons and 150K Daltons; wherein the active substance susceptible to abuse has an extended release profile, and wherein the formulation includes a physical barrier to reduce abuse.

In another embodiment, the present disclosure relates to an oral, extended release, abuse deterrent dosage formulation comprising an active substance susceptible to abuse; and a matrix agent, wherein the matrix agent has an average molecular weight between about 250K Daltons and 350K Daltons; wherein the active substance susceptible to abuse has an extended release profile, and wherein the formulation includes a physical barrier to reduce abuse.

In another embodiment, the present disclosure relates to an oral, extended release, abuse deterrent dosage formulation comprising an active substance susceptible to abuse; and a matrix agent, wherein the matrix agent has an average molecular weight between about 550K Daltons and 650K Daltons; wherein the active substance susceptible to abuse has an extended release profile, and wherein the formulation includes a physical barrier to reduce abuse.

The performance of the matrix agent and the formulation is also dependent on the amount of matrix agent present in the formulation. The formulation, or final dosage form, may contain about 8, 10, 12, 14, 15, 16, 18, 20, 22, 23, 24, 26, 27, 28, 30, 32, 34, 36, 37, 38, 40, 42, 44, 46, 48, 50, 52, 54, 56, 58, 60, 62, 64, 66, 68, 70, 72, 74, 76, 78 or 80 wt % matrix agent. These values may also be used to define a range of matrix agent in the formulation, such as about 8 wt % to about 12 wt %, or about 15 wt % to about 40 wt %, or about 20 wt % to about 37 wt %, or about 23 wt % to about 30 wt %, or about 25 wt % to about 27 wt %, or any combination of values, such as about 23 wt % to about 27 wt % or about 37 wt % to 40 wt %.

For embodiments wherein the matrix agent has an average molecular weight between about 50K Daltons and 150K Daltons, the formulation, or final dosage form, may contain about 8 wt % to about 40 wt % matrix agent, or about 8 wt % to about 12 wt %, or about 15 wt % to about 35 wt %, or about 20 wt % to about 30 wt %, or about 23 wt % to about 27 wt %, or any combination of values. For embodiments wherein the matrix agent has an average molecular weight between about 250K Daltons and 350K Daltons, the formulation, or final dosage form, may contain about 15 wt % to about 40 wt % matrix agent, or about 20 wt % to about 37 wt %, or about 25 wt % to about 30 wt %, or any combination of values. For embodiments wherein the matrix agent has an average molecular weight between about 550K Daltons and 650K Daltons, the formulation, or final dosage form, may contain about 15 wt % to about 40 wt % matrix agent, or about 20 wt % to about 37 wt %, or about 25 wt % to about 30 wt %, or any combination of values.

The dosage form of the present disclosure can also contain at least one plasticizer in the formulation. Incorporation of a plasticizer, in some embodiments, is optional. The plasticizer may increase the abuse deterrent properties by providing added waxiness upon exposure to physical or mechanical forces, such as pulverizing or grinding. The plasticizer may also improve the manufacture or processing of the formulation by decreasing the melt temperature and viscosity of the formulation in the extruder. Additionally, the plasticizer may aide in extraction prevention by decreasing extract purity and subsequent reconstitution to a pure crystalline form. Suitable plasticizers may be selected from the group consisting of polyalkalene glycols (e.g., polyethylene glycol and polyethylene glycol monomethyl ether), acetyltributyl citrate, acetyltriethyl citrate, castor oil, diacetylated monoglycerides, dibutyl sebacate, diethyl phthalate, glycerin, propylene glycol, pullulan, sorbitol sorbitan solution, triacetin, tributyl citrate and triethyl citrate. In one embodiment, the plasticizer is polyethylene glycol.

The performance of the plasticizer is dependent on the size and the amount of plasticizer present in the formulation. The formulation of the present disclosure may include a plasticizer having a molecular weight between about 1K Daltons and about 15K Daltons. Particularly, the molecular weight is between about 1K Daltons and about 10K, about 3K and about 9K Daltons. The formulation, or final dosage form, may contain between about 0 wt % and about 40 wt %, or about 1 wt % and about 35 wt %, or about 2 wt % and about 35 wt %, or about 3 wt % and about 30 wt %, or about 5 wt % and about 30 wt %, or about 10 wt % and about 20 wt %, or about 10 wt % and about 15 wt % plasticizer, or any combination of values, such as about 1 wt % to about 3 wt %.

For embodiments wherein the matrix agent has an average molecular weight between about 50K Daltons and 150K Daltons, the formulation, or final dosage form, may contain about 0 wt % to about 30 wt % plasticizer, or about 1 wt % to about 25 wt %, or about 2 wt % to about 22 wt %, or about 3 wt % to about 18 wt %, or about 10 wt % to about 15 wt %, or any combination of values. For embodiments wherein the matrix agent has an average molecular weight between about 250K Daltons and 350K Daltons, the formulation, or final dosage form, may contain about 0 wt % to about 40 wt % plasticizer, or about 5 wt % to about 35 wt %, or about 10 wt % to about 32 wt %, or about 24 wt % to about 31 wt %, or about 27 wt % to about 30 wt %, or any combination of values. For embodiments wherein the matrix agent has an average molecular weight between about 550K Daltons and 650K Daltons, the formulation, or final dosage form, may contain about 0 wt % to about 40 wt % plasticizer, or about 5 wt % to about 35 wt %, or about 10 wt % to about 32 wt %, or about 24 wt % to about 31 wt %, or about 27 wt % to about 30 wt %, or any combination of values.

The dosage form of the present disclosure may also contain a controlled release agent. The controlled release agent provides for time-dependent drug release from the formulation after administration over an extended period of time. The controlled release agent may be selected from the group consisting of polyvinyl acetate, polyvinylpyrrolidone, cellulose ethers, cellulose esters, acrylic resins, and derivatives thereof, and combinations thereof. Particularly, the controlled release agent may be selected from ethylcellulose, hydroxypropyl methylcellulose, hydroxypropylcellulose, hydroxymethylcellulose, poly(meth)acrylic acid and derivatives thereof, such as the salts, amides or esters, and combinations thereof. The formulation, or final dosage form, may contain between about 8 wt %/o and about 62 wt % of controlled release agent, or about 10 wt % and about 60 wt %, or about 15 wt % and about 58 wt %, or about 20 wt % and about 50 wt %, or about 30 wt % and about 45 wt %, or about 32 wt % and about 43 wt %, or about 35 wt % and about 40 wt %, or any combination of lower and higher limits, such as about 58 wt % to about 62 wt %.

For embodiments wherein the matrix agent has an average molecular weight between about 50K Daltons and 150K Daltons, the formulation, or final dosage form, may contain about 8 wt % to about 60 wt % controlled release agent, or about 20 wt % to about 60 wt %, or about 30 wt % to about 55 wt %. For embodiments wherein the matrix agent has an average molecular weight between about 250K Daltons and 350K Daltons, the formulation, or final dosage form, may contain about 10 wt % to about 50 wt % controlled release agent, or about 15 wt % to about 45 wt %, or about 20 wt % to about 40 wt %. For embodiments wherein the matrix agent has an average molecular weight between about 550K Daltons and 650K Daltons, the formulation, or final dosage form, may contain about 10 wt % to about 50 wt % controlled release agent, or about 15 wt % to about 45 wt %, or about 20 wt % to about 40 wt %. In some embodiments, the wt % of the controlled release agent is the total of all controlled release agents in the formulation. In other embodiments, the wt % of the controlled release agent refers to only one component of the formulation.

In some embodiments, the controlled release agent should be capable of both increasing viscosity of a solution by forming a gel and allowing extended release of the active substance. The formulation of the present disclosure may accomplish both capabilities by using a controlled release agent having an appropriate viscosity, such as between about 1 k mPa·s and about 200 k mPa·s. Particularly, the viscosity is between about 3 k mPa·s and about 150 k mPa·s, or about 4 k mPa·s and about 100 k mPa·s.

The matrix agent can be formulated with a specific controlled release agent that enhances the matrix agent's performance. For example, a formulation having a PEO matrix agent having a molecular weight between about 50K Daltons and about 350K Daltons, or about 50K to about 650K, can be combined with a controlled release agent containing PVAc and PVP. In one embodiment, the amount of PVAc and PVP is about 29 wt % to about 60 wt %, or about 40 wt % to about 50 wt %. In another embodiment, the formulation contains about 24 wt % to about 48 wt % of PVAc and about 5 wt % to about 12 wt % of PVP as the combined controlled release agent.

In another example, a formulation having a PEO matrix agent having a molecular weight between about 50K Daltons and about 650K Daltons, or about 250K Daltons and about 350K Daltons, or about 100K Daltons or about 300 K Daltons, or about 600K Daltons can be combined with a controlled release agent containing HPMC. In one embodiment, the amount of HPMC is about 20 wt % to about 40 wt %.

Without wishing to be bound by any particular theory, in some embodiments, the controlled release agent (e.g., HPMC) is believed to provide swelling/gelling of the pill matrix upon contact with an aqueous medium. The swelling/gelling of the matrix allows for time dependent drug release due to surface erosion of the pill over an extended period. In other embodiments, it is believed the differential aqueous solubility of the controlled release agent allows for time dependent drug release by diffusion over an extended period. For example, the controlled release agent can be a combination of PVAc and PVP. The PVAc can melt during extrusion to form a homogenous matrix, while the PVP does not melt. When introduced to an aqueous medium, the non-water soluble PVAc can stay in place within the formulation whereas the water soluble PVP can dissolve and leach out of the formulation. Pores can form from the removed PVP from which the active substance can diffuse out. In one embodiment, the present disclosure comprises a controlled release agent having a first component (e.g., PVAc) that can melt during extrusion to form a homogenous matrix and is substantially non-soluble under aqueous conditions, such as while the active substance is being released after administration, and a second component (e.g., PVP) that is water soluble under such conditions and which can form pores or passageways for the active substance to diffuse out of.

In some embodiments, the formulation includes a dye. A dye is useful in deterring abuse by discouraging the abuser from intravenous injection. For example, extraction of the dye along with the active ingredient would result in a colored solution that would discourage the abuser from intravenous injection. Thus, in certain embodiments, the dye reduces abuse by extracting and injecting. The dye may be selected from known dyes suitable for use in pharmaceutical formulations or approved by the FDA for such use. For example, the dye may be FD&C Yellow No. 5 or a 50/50 wt % solution of FD&C Yellow No. 5 in polyethylene glycol. In another embodiment, the dye may be a green dye comprising FD&C Yellow No. 5 and FD&C Blue No. 2. The dye may be in a 50% PEG 3350 blend. In another embodiment, the dye may be a violet dye comprising FD&C Red No. 40 and FD&C Blue No. 1. The dye may be in a 50% PEG 3350 blend. In certain embodiments, 4 mg of dye blend is used in each pill or about 2 mg of concentrated dye. In certain embodiments a dye is used since it is visually deterring and non-transparent. The dosage form may comprise about 0.10 wt %, 0.20 wt %, 0.30 wt %, 0.40 wt %, 0.50 wt %, 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, or 20 wt % dye. Any of these values may be used to define a range for the wt % of the dye. For example, the dosage form may contain between about 0.10 wt % and about 15 wt % dye. Particularly, the dosage form may contain between about 0.20 wt % and about 1.5 wt % dye, about 0.50 wt % and about 1.0 wt % dye, or about 7 to about 14 wt % dye. In certain embodiments, the dosage form may comprise about 1 mg, 1.4 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg or 30 mg of dye. In another embodiment, the dosage form of the present disclosure excludes a dye.

In another embodiment, the formulation can include a preservative or antioxidant. The preservative or antioxidant reduces or limits the degradation or deterioration of the abuse deterrent dosage form. For example, the components of the oral drug delivery system (e.g., active substances, matrix agents) may undergo degradation (e.g., oxidative reduction, chain cleavage) due to oxidation. In some embodiments, preventing degradation is essential to maintaining an active substance concentration as well as intended abuse deterrent properties. For instance, the molecular weight of PEO in the formulation affects the resistance to pulverization and viscosity upon introduction to an aqueous medium. The addition of a preservative or antioxidant in the formulation that reduces or eliminates the degradation of the molecular chain lengths of PEO is useful to maintain the abuse deterrent properties of the dosage form (e.g., butylated hydroxytoluene). Additionally, the inclusion of an antioxidant may prevent the oxidation of the active substance and therefore preserve the integrity of the product (e.g., citric acid).

The preservative or antioxidant may be selected from preservatives or antioxidants known to one skilled in the art for use in pharmaceutical formulations, such as silica, sodium laurel sulfate, citric acid, ascorbic acid, ascorbyl palmitate, butylated hydroxyanisole (BHA), butylated hydroxytoluene (BHT), erythorbic acid, hypophosphorous acid, lactobionic acid, monothioglycerol, potassium metabisulfite, propyl gallate, racemethionine, sodium bisulfite, sodium formaldehyde sulfoxylate, sodium metabisulfite, sodium sulfite, sodium thiosulfate, stannous chloride, sulfur dioxide and tocopherols. The formulation, or final dosage form, may contain between about 0.1 wt % and about 3.0 wt %, or about 0.25 wt % and about 1.5 wt % of preservative or antioxidant. In another embodiment, the formulation of the present disclosure excludes a preservative or antioxidant.

The formulation may additionally include at least one additive independently selected from surfactants, fillers, bulking agents, lubricants, colorants, flavorings or combination thereof.

In certain embodiments, the present disclosure relates to an oral, extended release, abuse deterrent dosage formulation having oxycodone present at about 5 to about 40 wt %, PEO having an average molecular weight of about 50K to about 150K Daltons and present between about 8 wt % and 35 wt %; PVAc, PVP, or a combination thereof present between about 8 wt % and 60 wt %; polyethylene glycol having an average molecular weight of about 8K Daltons and present between about 0 wt % and 30 wt %; and optionally a dye blend having a ratio of FD&C dye to polyethylene glycol present between about 0% and 15%. The formulation also has an extended release profile of the active substance which passes the criteria for extended release oxycodone according to the USP monograph or the matching reference listed drug for extended release oxycodone and has at least 50 wt % of particles sized greater than 0.5 mm following physical or mechanical manipulation of the formulation. The formulation may also have PEO present between about 20 wt % and 70 wt %, PVAc, PVP, or a combination thereof present between about 20 wt % and 60 wt %, and polyethylene glycol present between about 2 wt % and 20 wt %. Alternatively, the formulation may also have PEO present between about 23 wt % and 40 wt %, PVAc, PVP, or a combination thereof present between about 30 wt % and 55 wt %, and polyethylene glycol present between about 2 wt % and 15 wt %.

In other embodiments, the present disclosure relates to an oral, extended release, abuse deterrent dosage formulation having oxycodone present at about 5 to about 40 wt %, PEO having an average molecular weight of about 250K to about 350K Daltons and present between about 15 wt % and 70 wt %; HPMC present between about 10 wt % and 50 wt %; polyethylene glycol having an average molecular weight of about 8K Daltons and present between about 0 wt % and 40 wt %; and optionally a dye blend having a ratio of FD&C dye to polyethylene glycol present between about 0% and 15%. The formulation also has an extended release profile of the active substance which passes the criteria for extended release oxycodone according to the USP monograph or the matching reference listed drug for extended release oxycodone and has at least 50 wt % of particles sized greater than 0.5 mm following physical or mechanical manipulation of the formulation. The formulation may also have PEO present between about 20 wt % and 40 wt %, HPMC present between about 15 wt % and 45 wt %, and polyethylene glycol present between about 5 wt % and 40 wt %. Alternatively, the formulation may also have PEO present between about 25 wt % and 30 wt %, HPMC present between about 20 wt % and 40 wt %, and polyethylene glycol present between about 10 wt % and 35 wt %.

In other embodiments, the present disclosure relates to an oral, extended release, abuse deterrent dosage formulation having oxycodone present at about 5 to about 40 wt %, PEO having an average molecular weight of about 550K to about 650K Daltons and present between about 15 wt % and 70 wt %; HPMC present between about 10 wt % and 50 wt %; polyethylene glycol having an average molecular weight of about 8K Daltons and present between about 0 wt % and 40 wt %; and optionally a dye blend having a ratio of FD&C dye to polyethylene glycol present between about 0% and 15%. The formulation also has an extended release profile of the active substance which passes the criteria for extended release oxycodone according to the USP monograph or the matching reference listed drug for extended release oxycodone and has at least 50 wt % of particles sized greater than 0.5 mm following physical or mechanical manipulation of the formulation. The formulation may also have PEO present between about 20 wt % and 40 wt %, HPMC present between about 15 wt % and 45 wt %, and polyethylene glycol present between about 5 wt % and 40 wt %. Alternatively, the formulation may also have PEO present between about 25 wt % and 30 wt %, HPMC present between about 20 wt % and 40 wt %, and polyethylene glycol present between about 10 wt % and 35 wt %.

The abuse deterrent pill of the present disclosure is capable of extended release of the active substance. The dosage form may be manufactured to provide a composition exhibiting an extended release profile of at least one active substance. As used herein, "extended release" refers to a dosage form that releases the active substance or a pharmaceutically acceptable salt thereof, into the gastrointestinal tract of the user over an extended period, e.g., 6-8 hours, 8-12 hours. Particularly, the active substance is released substantially continuously the period, e.g., 6-8 or 8-12 hours. In one embodiment, the amount of active substance released from the dosage form, e.g. oxycodone HCl, by exposure to simulated gastric fluid within 8-12 hours is about 85%. In another embodiment, the amount of active substance released from the dosage form, e.g. oxycodone HCl, by exposure to simulated gastric fluid within 6-8 hours is about 80%. The formulation of the present disclosure exhibits an extended release profile that passes the criteria for the USP monograph or for the matching reference listed drug (RLD) for extended release active substance.

In different embodiments, the amount of active substance released from the dosage form by exposure to simulated gastric fluid is shown in Tables 1-4. The values in Tables 1-4 represent acceptable USP criterion and may differ from values associated with the RLD specifications.

TABLE 1

Exemplary Release Profile (e.g. 10 mg, 20 mg, 40 mg active)

| Time (Hours) | Amount |
| --- | --- |
| 1 | between about 20% and about 40% |
| 2 | between about 35% and about 55% |
| 4 | between about 55% and about 75% |
| 6 | between about 70% and about 90% |
| 8 | Not less than about 80% |

TABLE 2

Exemplary Release Profile (e.g. 20 mg active)

| Time (Hours) | Amount |
|---|---|
| 1 | between about 33% and about 53% |
| 4 | between about 63% and about 83% |
| 12 | not less than about 85% |

TABLE 3

Exemplary Release Profile (e.g. 40 mg active)

| Time (Hours) | Amount |
|---|---|
| 1 | between about 37% and about 57% |
| 4 | between about 68% and about 88% |
| 12 | not less than about 85% |

TABLE 4a

Exemplary Release Profile (e.g. 80 mg active)

| Hour | Amount |
|---|---|
| 1 | between about 25% and about 45% |
| 2 | between about 45% and about 65% |
| 4 | between about 65% and about 85% |
| 6 | Not less than about 80% |

TABLE 4b

Exemplary Release Profile (e.g. 80 mg active)

| Hour | Amount |
|---|---|
| 1 | between about 31% and about 51% |
| 4 | between about 61% and about 81% |
| 12 | Not less than about 85% |

The formulation, or abuse deterrent pill, may also include at least one physical barrier to reduce abuse. The physical barrier may be the inability of the pill to be abused by pulverizing and snorting, pulverizing and injecting, or combinations thereof. For example, the abuse deterrent pill of the present disclosure may be incapable of being significantly pulverized by physical or mechanical force.

One of the most common means of abuse of an orally administered opioid analgesic involves the manipulation of the oral dosage form in order to cause rapid delivery to the bloodstream via nasal insufflation. In order for insufflation to be used as an effective means of abuse, the original dosage form must be manipulated so as to decrease the particle size of the ingested drug to about 0.5 mm or less. A particle size of about 0.5 mm or less is necessary for effective intranasal absorption to occur. By limiting the quantity of particles under about 0.5 mm that an abuser can obtain by reasonable methods, one can render insufflation ineffective as a means of abuse. One way this physical barrier may be created is by capturing the active substance susceptible to abuse in a plastic matrix which is resistant to being physically broken down to produce particles smaller than about 0.5 mm.

The dosage form of the present disclosure can inhibit manipulation by grinding or pulverizing using common equipment, such as a coffee grinder. For example, the formulation deters abuse by limiting the particle size to which the formulation may be ground. The formulation prevents the pill, or at least substantial portions of the pill, from being ground in particles having a particle size of about 0.5 mm or less that may pass through the membrane of the nasal cavity to cause rapid delivery of the active substance to the bloodstream. The dosage form can also significantly limit the extraction of the active substance by common solvents (e.g., cold water, hot water (small volume) or high proof ethanol) from the formulation. For example, the formulation deters abuse by limiting the ability to extract the active substance from the formulation (either intentionally or unintentionally), such that the active substance cannot easily be concentrated for parenteral administration. The abuse deterrent formulation may also include, but does not require, the incorporation of other deterrents such as antagonists or irritants.

In one embodiment, the abuse deterrent pill of the present disclosure may be incapable of being crushed by grinding into a form that may be abused. In a typical coffee grinder analysis (e.g., grinding in a coffee grinder at about 20,000+ rpm and for about 30-60 seconds) the pill remains in a form that may not be abused. The coffee grinder analysis may be performed using a commercial coffee grinder, or equivalent, capable of grinding abuse deterrent pills. The pills tested using the coffee grinder analysis have a substantial portion of the resulting particles with a particle size which is not able to be abused, i.e. intranasal administration. Abuse deterrent pills having a substantial amount of such particles reduce the incentive or cost-effectiveness to abuse the formulations. For example, a potential abuser who can only access for intranasal administration less than about 50% of the active substance will be deterred from abusing the formulation.

Upon exposure to a grinding force (e.g., the coffee grinder analysis or equivalent), the abuse deterrent pill may be grinded into particles wherein at least about 50 wt % of the grinded particles have a particle size greater than about 0.5 mm. Particularly, upon exposure to a grinding force, the abuse deterrent pill may be grinded into particles wherein at least about 55 wt % of the grinded particles, 60 wt % of the grinded particles, 65 wt % of the grinded particles, 70 wt % of the grinded particles, 75 wt % of the grinded particles, 80 wt % of the grinded particles, 85 wt % of the grinded particles, 90 wt % of the grinded particles, or 95 wt % of the grinded particles have a particle size greater than about 0.5 mm.

In another embodiment, the abuse deterrent pill of the present disclosure may be capable of forming a hydrogel upon exposure to an aqueous or semi-aqueous solution. The formation of the hydrogel deters abuse by limiting the ability of persons to extract the active substance from the formulation, such that the active substance cannot easily be concentrated for parenteral administration.

In another embodiment, the formulation, or abuse deterrent pill, may also include at least one chemical barrier to reduce abuse. A common means of abusing opioids is using commonly available solvents to extract the active substance into a solution of a very high purity. For example, oxycodone is soluble in ethanol whereas many other excipients are only partially soluble or completely insoluble. This allows abusers to pull the active substance out of the dosage form, eliminate the extended release features of the dosage form, and return the active substance to a crystalline form to render it for abuse. The formulation of the present disclosure contains excipients which are also soluble in many of the same solvents as the active substance so that the purity of the final solution is about 80%, 70%, 60%, 50%, 40%, 30%, or about 20% pure. The inclusion of these additional excipients prevents an abuser from returning the active substance to a pure crystalline form by forming a waxy, colored residue when attempted to be extracted. In some embodiments, the dosage form does not include a chemical barrier to reduce abuse.

In another embodiment, the present disclosure relates to a process for the production of an oral, extended release, abuse deterrent pill containing at least one active substance susceptible to abuse comprising processing a uniform blend of the at least one active substance susceptible to abuse, a matrix agent, a controlled release agent, a plasticizer, and a dye by hot melt extrusion to produce an extrudate. The extrudate may therein be formed into a pill using a forming unit. The directly-formed oral, extended release, abuse deterrent dosage form can have an active substance susceptible to abuse, a matrix agent, a controlled release agent, a plasticizer, and a dye and be formed directly from an extrusion process having a forming unit. The forming unit can be a calendar, a rotary, or chain forming machine.

Hot melt extrusion is a processing technique used to make the formulations and compositions of the present disclosure because it allows for the creation of homogeneous polymer matrices with specific abuse deterrent properties. For example, by varying the formulation and the processing parameters specific properties such as dissolution profile, crush resistance, material processability, and stability can be selectively modified. Formulations that include polymer matrix agents (e.g., PEO) can provide a unique advantage as they allow for formulations in which release characteristics can be controlled while also creating a physical barrier that prevents abuse (e.g., through means of nasal inhalation or intravenous injection). Furthermore, in a hot melt extrusion process, process analytic data can be provided in real time. The process may also be adapted for continuous process manufacturing procedure as opposed to traditional batch to batch processing.

The abuse deterrent pill of the present disclosure may be formed by hot melt extrusion using commercially available extruders, such as a twin screw extruder. The heat associated with the extrusion process may be added preceding, simultaneous, or subsequent to the manufacturing process. Several factors of the extrusion process may affect the final extrudate including: screw design (sheer rating), screw speed, temperature profile, feed rate, dwell time, die pressure and die size. These factors may be varied to obtain an extrudate with desired processing capabilities such that the extrudate is uniform, maintains its shape, and is capable of being formed into pills by a forming unit.

An exemplary extruder and forming unit system (10) is shown in FIG. 1. The extruder (14) includes a hopper or feeding unit (12) wherein a uniform blend of the formulation is made or transferred to. The uniform blend is fed into the inlet (16) of the extruder (14) by starve feeding via a gravimetric or volumetric dosing unit. The formulation of the present disclosure is preferably uniformly blended prior to introduction to the extrusion process. Insufficient blending of the components may produce a non-uniform extrudate and non-uniform abuse deterrent pills having inconsistent amounts of active substance. Over-blending may produce a poorly performing formulation. The blending process may be monitored using a process analytical technique to determine when a uniform blend is achieved. In one embodiment, the mixing bin or hopper (12) may be equipped with a near-infrared (NIR) monitoring system for in-line, continuous monitoring of the blend.

In one embodiment, monitoring of the blending process by NIR involves preparing a NIR standard spectrum for each formulation. The NIR standard spectra may be prepared empirically by monitoring the blending of different batches of the formulation. The blending conditions and/or the extrusion process may be correlated with NIR spectra to determine a NIR standard spectrum. Once the optimum NIR monitoring spectra and conditions are determined, the formulation is blended until the NIR standard is achieved. One of ordinary skill in the art armed with the present disclosure can implement a near-infrared monitoring system for in-line, continuous monitoring of the blend.

The extruder (14) then processes the blend into a melt and passes the extrudate (50) out of the extruder (14) through a die section (30) and through a die outlet (18). The extruder (14) may have temperature zones (20-30) and pressure zone (40-43). These zones may include components to heat and pressurize the extruder (14) or may include sensors to measure the temperature or pressure of each particular zone.

As used herein the term melt temperature refers to the temperature at which an excipient changes from solid to liquid state. As used herein the term softening temperature refers to the temperature at which an excipient changes from solid form into a malleable, dynamic solid.

The temperature profile of the extruder (14) is important to obtain a uniform extrudate (50) with little to no degradation products. Heat may be applied to soften, and in some embodiments to melt, the excipients (e.g., matrix agent, controlled release agent, plasticizer) to form a homogenous matrix to encapsulate the active substance. The extruder temperature profile, or the temperatures in the extruder zones (20-30), is preferably kept below the melting point, and often the degradation point, of the active substance.

For example, the melting temperature of PEO is about 67° C. and of polyethylene glycol is about 63° C. Common active substances begin to melt at temperatures much higher than this. For example, the melt temperature of oxycodone HCl is about 219° C. Preferably, the temperature of one or more of the zones (20-30) is kept at or below the melting point of the active pharmaceutical ingredients. In particular, the temperature of one or more of the zones (20-30) is kept below about 150° C., 140° C., 130° C., 120° C., 110° C., 100° C., 90° C., 80° C., 75° C., 70° C., 65° C., or 60° C.

In one embodiment, the temperature of at least one of the extruder zones (20-30) is kept at or below the melting point of the active pharmaceutical ingredients. Particularly, the temperature of at least one of the zones is kept below about 150° C. 140° C., 130° C., 120° C., about 110° C., about 100° C., about 90° C., about 80° C., about 75° C., about 70° C., about 65° C., or about 60° C.

In another embodiment, the temperature of at least two of the extruder zones (20-30) is kept at or below the melting point of the active pharmaceutical ingredients. Particularly, the temperature of at least two of the zones is kept below about 150° C., 140° C., 130° C., 120° C., about 110° C., about 100° C., about 90° C., about 80° C., about 75° C., about 70° C., about 65° C., or about 60° C.

In another embodiment, the temperature of at least three of the extruder zones (20-30) is kept at or below the melting point of the active pharmaceutical ingredients. Particularly, the temperature of at least three of the zones is kept below about 150° C., 140° C., 130° C., 120° C., about 110° C., about 100° C., about 90° C., about 80° C., about 75° C., about 70° C., about 65° C., or about 60° C.

In another embodiment, the temperature of at least four of the extruder zones (20-30) is kept at or below the melting point of the active pharmaceutical ingredients. Particularly, the temperature of at least four of the zones is kept below about 150° C., 140° C., 130° C., 120° C., about 110° C., about 100° C., about 90° C., about 80° C., about 75° C., about 70° C., about 65° C., or about 60° C.

In another embodiment, the temperature of at least five of the extruder zones (20-30) is kept at or below the melting point of the active pharmaceutical ingredients. Particularly, the temperature of at least five of the zones is kept below about 150° C., 140° C., 130° C., 120° C., about 110° C., about 100° C., about 90° C., about 80° C., about 75° C., about 70° C., about 65° C., or about 60° C.

In another embodiment, the temperature of at least six of the extruder zones (20-30) is kept at or below the melting point of the active pharmaceutical ingredients. Particularly, the temperature of at least six of the zones is kept below about 150° C., 140° C., 130° C. 120° C., about 110° C., about 100° C., about 90° C., about 80° C., about 75° C., about 70° C., about 65° C. or about 60° C.

In another embodiment, the temperature of all of the extruder zones (20-30) is kept at or below the melting point of the active pharmaceutical ingredients, with the optional exception of the die zone. Particularly, the temperature of all of the zones is kept below about 150° C., 140° C., 130° C., 120° C., about 110° C., about 100° C. about 90° C., about 80° C., about 75° C., about 70° C., about 65° C., or about 60° C., with the optional exception of the die zone.

The temperature of the die (18, 30) may be maintained at a slightly higher temperature than the temperature of one or more of the other zones. In some embodiments, the die temperature (18, 30) is held at or slightly above the melting point of the extrudate to ensure a uniform extrudate (50) exiting the die outlet (18).

The extruder (14) also has a pressure profile. Pressure is important to melt the excipients to make mixing more efficient and to force the extrudate (50) through the die outlet (18) to exit the extruder (14) in a consistent manner. Particularly, the pressures in the zones and also the pressure at the die outlet (18), is kept at or above about 30 bar, about 40 bar, about 50 bar, about 60 bar, about 70 bar, about 80 bar, about 90 bar, about 100 bar, about 110 bar, about 120 bar, about 130 bar, about 140 bar or about 150 bar.

In one embodiment, the pressure of one or more of the pressure zones (40-43) in the extruder (14) is kept at a high enough pressure to achieve melting, compression, and mixing of the matrix agent, controlled release agent and plasticizier with non-melting excipients (e.g., active substance, preservative/antioxidant, etc.) while the temperature of one or more of the temperature zones (20-30) is at or slightly below the melting point at standard pressure of one or more of these agents. The increased pressure allows for more efficient mixing due to compaction and shearing forces without having to dramatically increase temperature. These lower temperatures reduce, or substantially eliminate, the formation of degradation products from the active substances. In one embodiment, the pressure produced on the die (43) of the extruder (14) is kept sufficiently high enough to reduce pulsating flow and ensure a uniform extrudate (50) is delivered though the die outlet (18). A sufficiently high pressure assists in compacting the homogenous melt into a processable strand of desired diameter.

In one embodiment, the pressure of at least one of the pressure zones (40-43) is kept at a high enough pressure to achieve melting, compression, and mixing of the matrix and plasticizing agents with the active substance and any non-melting excipients. Particularly, the pressure of at least one of the zones is kept at or above about 30 bar, about 40 bar, about 50 bar, about 60 bar, about 70 bar, about 80 bar, about 90 bar, about 100 bar, about 110 bar, about 120 bar, about 130 bar, about 140 bar or about 150 bar.

In another embodiment, the pressure of at least two of the pressure zones (40-43) is kept at a high enough pressure to achieve melting, compression, and mixing of the matrix and plasticizing agents with the active substance and any non-melting excipients. Particularly, the pressure of at least two of the zones is kept at or above about 30 bar, about 40 bar, about 50 bar, about 60 bar, about 70 bar, about 80 bar, about 90 bar, about 100 bar, about 110 bar, about 120 bar, about 130 bar, about 140 bar or about 150 bar.

In another embodiment, the pressure of at least three of the pressure zones (40-43) is kept at a high enough pressure to achieve melting, compression, and mixing of the matrix and plasticizing agents with the active substance and any non-melting excipients. Particularly, the pressure of at least three of the zones is kept at or above about 30 bar, about 40 bar, about 50 bar, about 60 bar, about 70 bar, about 80 bar, about 90 bar, about 100 bar, about 110 bar, about 120 bar, about 130 bar, about 140 bar or about 150 bar.

In another embodiment, the pressure of all of the pressure zones (40-43) is kept at a high enough pressure to achieve melting, compression, and mixing of the matrix and plasticizing agents with the active substance and any non-melting excipients. Particularly, the pressure of all of the zones is kept at or above about 30 bar, about 40 bar, about 50 bar, about 60 bar, about 70 bar, about 80 bar, about 90 bar, about 100 bar, about 110 bar, about 120 bar, about 130 bar, about 140 bar or about 150 bar.

In another embodiment, the pressure parameter is not critical to the formation of the formulation. The pressure of all of the pressure zones (40-43) can be run at about 5 to about 20 bar, in particular from about 10 to about 15 bar.

The melt extrudate may be optionally analyzed within the extruder (14) using near-infrared technology. NIR spectroscopy can be used as a non-invasive alternative to high performance liquid chromatography techniques. A NIR probe (80) may be included within the extruder (14). The wavelengths and intensities at which raw organic materials of the melt extrudate absorb light energy can be plotted to produce spectra to compare against a standard. With the spectrum of the API known, it can be used to determine and monitor the % wt of the active pharmaceutical ingredient present in the extrudate in real time.

The extrudate from an extruder is directly formed into a pill using a forming unit, provided that the size or shape of the extrudate may be adjusted prior to introduction to the forming unit (e.g., via a rope sizer). In some embodiments, the extrudate is directly formed into a dosage form without a further processing step, such as a cutting or milling step. The forming unit may be a unit capable of forming the pill without cutting or milling the extrudate. The forming unit may be a calendar, rotary, or a chain forming machine. As shown in FIG. 1, the extrudate (50) may be shaped into the abuse deterrent form (70) by a forming unit (60). In one embodiment, the extrudate (50) is shaped into the abuse deterrent form (70) by a calendaring process.

The forming unit (60) may comprise two rotating components each having molds (62) inset in the rotating components and aligned such that the molds (62) overlap with each other as the rotating components interface. When the extrudate (50) is guided between the rotating components of the forming unit (60), the offset and aligned molds (62) (or cavities) accept the extrudate and form the extrudate into the dosage form as provided by the shape of the molds (62), provided a sufficient amount of extrudate is guided between and supplied to the rotating components.

Figure 2:
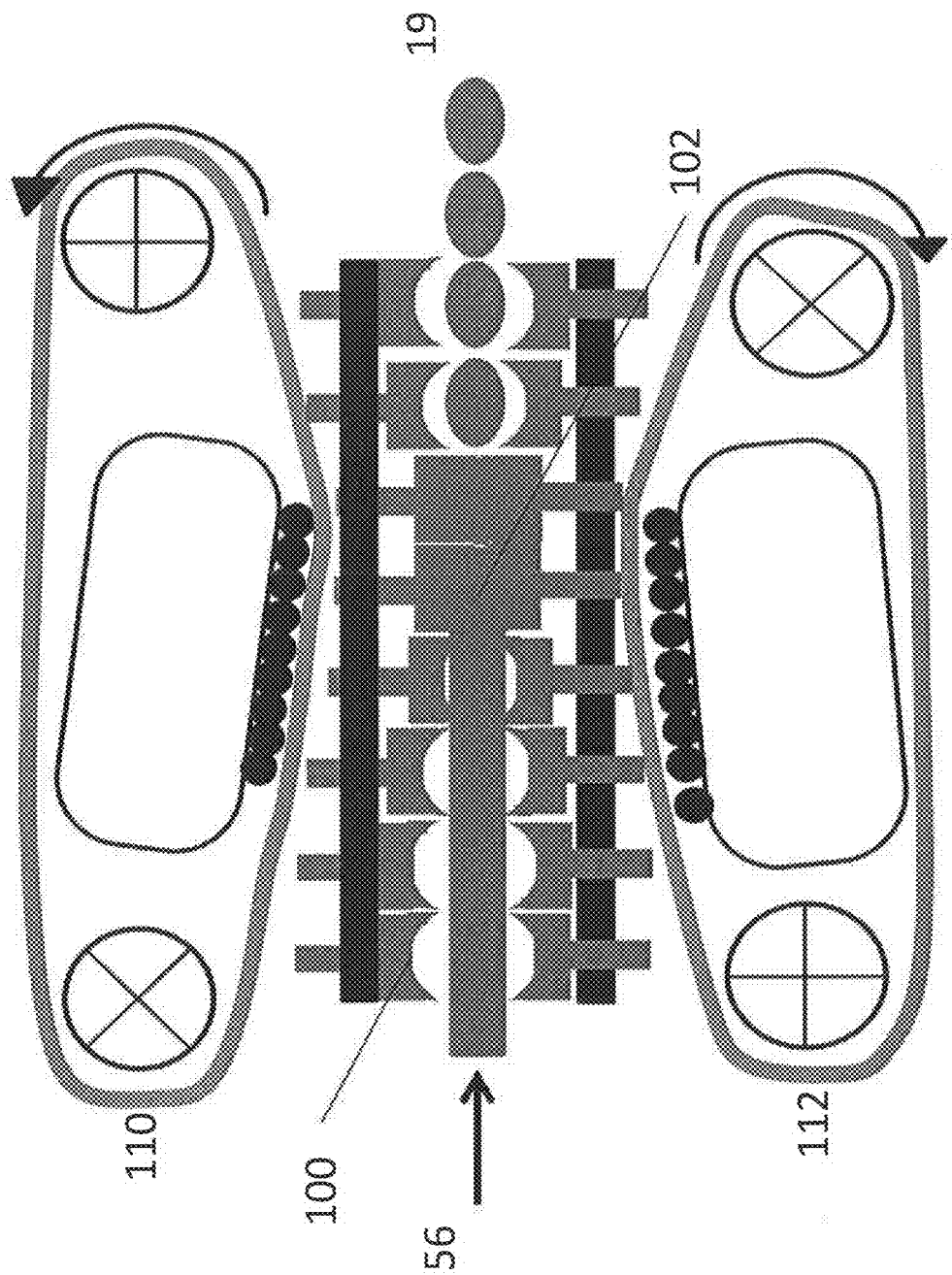
FIG. 2 shows an embodiment of a chain forming unit. The chain forming unit includes an upper and lower chain system (110 and 112) and tooling (100) to form the incoming extrudate (56) into formed pills (19).

In another embodiment, the forming unit may also comprise of a rotating set of punch dies with accompanying pinching ring, e.g. a chain die forming unit. FIG. 2 shows an embodiment of a chain forming unit. The chain forming unit includes an upper and lower chain system (110 and 112) and tooling (100) to form an incoming extrudate (56) into formed pills (19). When the extrudate (56) is fed into the chain die forming unit, the ring tooling (100) pinches the extrudate (56) to the exact weight of the finished pill and simultaneously presses it into a final form by the punches via a cam track. In one embodiment, the centripetal forces produced by the rotation of the machine aid in the ejection of the final pill form (19).

The extruder/forming unit system (10) may also be equipped with an additional component or transfer unit to assist the transfer of the extrudate (50) from the extruder (14) to the forming unit (60). The transfer unit may be capable of controlling the temperature, pressure, environment and/or shape of the extrudate. For example, the transfer unit may include heated/cooled sizing rollers which process the extrudate (50) into a consistent size (e.g., diameter) before entering the forming unit. The transfer unit may also be capable of guiding the extrudate into and between the rotating components of the forming unit (60).

Figure 3:
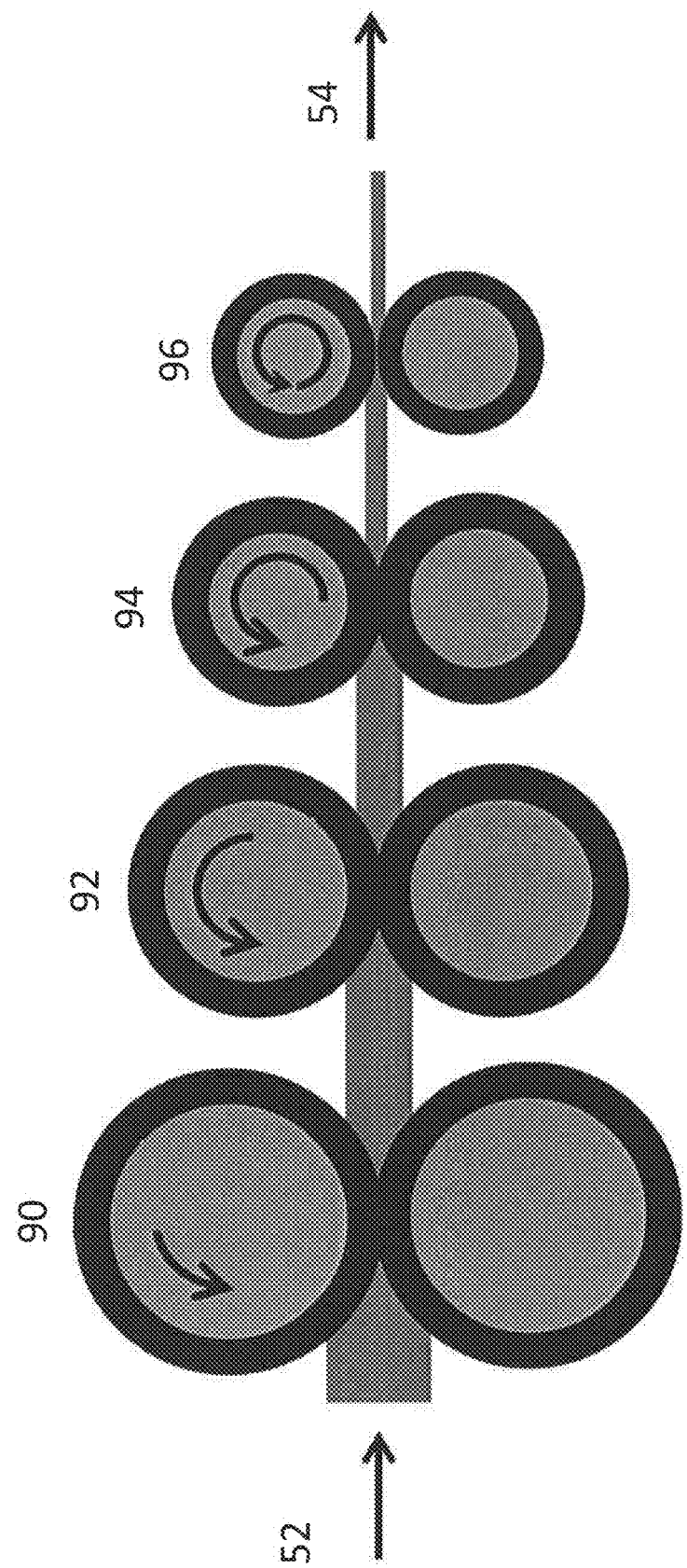
FIG. 3 shows an embodiment of an extrudate sizing apparatus (e.g., rope sizer). The rope sizer includes consecutive rollers (90-96) rotating at consecutively faster speeds for accepting an incoming extrudate (52) and expelling a faster moving, re-sized (smaller diameter) extrudate (54).

For example, the extrudate may be adjusted by an apparatus that re-sizes the extrudate, re-shapes the extrudate, or both. FIG. 3 shows an embodiment of an extrudate sizing apparatus (e.g., rope sizer). The rope sizer includes a number of consecutive rollers (90-96) to re-size or re-shape an incoming extrudate (52), either from the extruder (14) or from another step. The number, shape and orientation of the rollers (90-96) may vary depending on the degree of re-sizing and/or re-shaping desired. In some embodiments, the extrudate will be re-sized into a smaller diameter extrudate. In these embodiments, the rotating rollers will rotate at consecutively faster speeds. As such, the re-sized and/or re-shaped extrudate having a smaller diameter will be moving at a faster speed exiting the rope sizer.

The size and shape of the extrudate (50) may be designed to efficiently interact with different shaped molds (62). For example, an oval shaped extrudate may be formed to interact with a wide and shallow set of molds (62). Also, the speed and mass (or volume) of the extrudate (50) may be designed to efficiently interact with the size and speed of the forming unit. The speed and mass (or volume) of the extrudate (50) guided between the rotating components of the forming unit (60) should be sufficient to fill each set of molds completely with no voids.

The size and shape, and the speed and mass (or volume) of the extrudate (50) as well as size and shape of the molds (62) and the speed of the forming unit may be matched to reduce the amount of excess extrudate that is not formed into the dosage form (e.g., reduce waste). The two processes may be synchronized by attaching both to the same drive system. Preferably, the forming unit is capable of forming abuse deterrent pills from the extrudate wherein more than about 90% of the extrudate is utilized (e.g., formed into the dosage form). More preferably, the forming unit utilizes more than about 95% of the extrudate. Even more preferably, the forming unit utilizes more than about 99% of the extrudate.

The molds (62) may optionally be formed with a non-uniform bottom or lower surface to allow for easy removal of the pill after formation. The molds (62) may also have markings in the bottom or lower surface to provide marking on the abuse deterrent pills upon formation.

After formation, the quality, volume and weight of each pill may be determined using an automated optical inspection technique. The optional inspection technique combines a weight determination step and a visual inspection step into a single step. For example, the visualization step may include taking multiple pictures of each pill. From these pictures, an estimated volume is determined. The estimated volume and the pre-determined density of the composition of the formulation may provide an estimated weight for each pill. Those pills that satisfy certain quality, volume and weight criteria will pass the optical inspection.

In another embodiment, the present disclosure relates to a process for the production of an oral, extended release, abuse deterrent pill containing at least one active substance susceptible to abuse comprising combining the at least one active substance susceptible to abuse, a matrix agent, a controlled release agent, a plasticizer, and a dye in a hopper to form a mixture; blending the mixture in the hopper until a uniform blend is achieved; monitoring the mixture during blending using a process analytical technique to determine when a uniform blend is achieved; feeding the uniform blend into an extruder; processing the uniform blend by hot melt extrusion to produce an extrudate; optionally monitoring of the extrudate at the die head via PAT NIR probe; transferring the extrudate to a forming unit using a transfer line capable of controlling the temperature, pressure, environment, and/or shape of the extrudate; forming the extrudate using the forming unit into the pill; and determining the quality, volume and weight of the pill using an optical inspection technique.

In another embodiment, the extended release, abuse deterrent pill containing at least one active substance susceptible of the present disclosure is prepared using a process combining direct tableting and preceding, simultaneous, or subsequent heat to cure the dosage form. The process involves blending the excipients to a homogenous blend, directly compressing using a tablet press, and adding preceding, simultaneous, or subsequent heat to form a hard shell around the dosage form to deter crushing. In some embodiments, this process may be carried out utilizing an oven or coating pan. The process temperature of this step is kept at a point that does not significantly melt or deform the pill. Particularly, the process temperature is kept at or below 150° C., 140° C., 130° C., 120° C., 110° C., 100° C., 90° C. 80° C., 70° C., 60° C., 50° C., or 40° C. In other embodiments, this process may be carried out utilizing tablet press tooling which is heated prior to and/or during compression.

In another embodiment, the present disclosure relates to a method of treating pain comprising administering to an individual in need thereof a therapeutically effective amount of a dosage form as described herein. The dosage form provides analgesia for the treatment of moderate to severe pain over a period of about 12 hours.

The disclosures of all cited references including publications, patents, and patent applications are expressly incorporated herein by reference in their entirety. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention is further defined in the following Examples. It should be understood that these Examples, while indicating preferred embodiments of the invention, are given by way of illustration only.

EXAMPLES

Example 1

Initial testing was performed using abuse deterrent formulations containing acetaminophen. Acetaminophen was utilized as a tracer in place of oxycodone HCl for early experiments due to its availability, similar dissolution/solubility profile and cost-effectiveness. Extended release abuse deterrent pills containing acetaminophen in place of oxycodone HCl were manufactured according to the following formulation as provided in Tables 5-6.

TABLE 5

Exemplary Extended Release Abuse Deterrent Pill Formulation Ranges

| Components | % Wt. |
|---|---|
| Active Substance | 5.0-40.0 |
| Matrix/Controlled Release Agent | 20.0-70.0 |
| Plasticizer (8K Da) | 20.0-70.0 |

TABLE 6

Exemplary Extended Release Abuse Deterrent Pill Formulation Ranges

| Components | % Wt. |
|---|---|
| Active Substance | 5.0-40.0 |
| Polyvinyl Acetate | 25.0-50.0 |
| Polyvinylpyrrolidone | 5.0-15.0 |
| Sodium Lauryl Sulfate | 0.1-0.75 |
| Silica | 0.01-0.2 |
| Polyethylene Glycol (8k Da) | 2.0-15.0 |
| Antioxidants | 0.0-2.0 |
| Dye | 0.0-2.0 |

Abuse deterrent pills containing acetaminophen were made by blending the formulation components in a Turbula T2F mixer shaker at 30 RPM for 5 minutes.

Extrusion was performed by means of a twin screw extruder of type Steer Omega 20. To achieve a uniform extrudate with good processing capabilities a medium sheer screw design was used at a relatively slow screw speed (150 RPM). The temperature profile was designed to immediately melt the melting excipients (e.g., PEO, polyethylene glycol, and/or PVAc). Thereafter, the temperature was adjusted to be at or above the melting temperature of the melting excipients of the formulation at standard pressure to achieve mixing, decrease viscosity, and limit high torque forces on the extruder. Adequate mixing was achieved by maintaining high pressures in the extruder.

At times, the die was heated above the general melt temperature of the extrudate. It was found that at die temperatures at the melt temperature of the extrudate, the portion of the extrudate in contact with the inside die surface sheared off due to friction. An increase in die temperature decreased this frictional force and allowed the extrudate to slide along the die producing a glossy, uniform extrudate. Operating temperatures and pressures are provided in Table 7. The temperature and pressure zones in Table 7 correspond to the zones shown in FIG. 1.

TABLE 7

Extrusion Temperature and Pressure

| | Temp | Pressure |
|---|---|---|
| Zone 1 | 60-70° C. | |
| Zone 2 | 60-70° C. | |
| Zone 3 | 70-80° C. | |
| Zone 4 | 70-80° C. | |
| Zone 5 | 80-90° C. | |
| Zone 6 | 90-100° C. | |
| Zone 7 | 90-100° C. | |
| Die | 100-125° C. | |
| Melt Pressure | | 30-150 bar |

The temperature profile, feed rate, and die size all have an effect on the pressure produced on the die head. A die size of 6 mm was used. The temperature profile was kept relatively static. The feed rate was adjusted to maintain a consistent and high pressure on the die head of about 50 bar.

For the experiment, a Carver Press was used to form the extrudate into a pill form. The Carver Press is a manual hydraulic press, utilizing a free standing set of Natoli upper and lower punches that meet at a die. Dedicated tooling was made for the experiment in order to produce 200-400 mg pills.

The extrudate was hand cut, based on weight (200-400 mg). The die was placed on top of the bottom punch, the cut extrudate was placed in the die cavity, and the top punch placed through the top section of the die. The cut extrudate was formed into a pill at around 1+/−0.5 metric tons of force, using the Carver Press and Natoli die set.

Dissolution Testing

The abuse deterrent pills containing acetaminophen were tested for dissolution. Additional pills were formed and tested containing oxycodone HCl as the active substance. Dissolution testing was performed with reference to USP Monograph on Oxycodone Hydrochloride Extended-Release Tablets. These tests were performed on a dissolution apparatus utilizing UPS <711> Apparatus I (Baskets), with 900 mL Simulated Gastric Fluid (no enzymes) as media and a basket speed of 100 rpm. Japanese Sinker Baskets (Part Number PSCUSBSK-JPMAG) were utilized. A 1.5 mL sample was pulled at 1 hour, 4 hours, and 12 hours (Dissolution Test 2 according to the USP monograph on Oxycodone Hydrochloride Extended-Release Tablets) and submitted for HPLC analysis. HPLC conditions were modified from the USP monograph in order to observe the release of acetaminophen or oxycodone HCl. The HPLC conditions were as follows: Injection Volume: 20 μL, (acetaminophen), 30 μL (oxycodone); Flow Rate 1.5 mL/min (acetaminophen), 1.7 mL/min (oxycodone); Detection: UV at 295 nm (acetaminophen), UV at 225 nm (oxycodone); Column Temp: 25° C.; Autosampler Temperature: ambient; Gradient: Isocratic; and Runtime: 5 minutes. In another embodiment, the dissolution tests were performed on a dissolution apparatus utilizing UPS <711> Apparatus I (Baskets), with 900 mL Simulated Gastric Fluid (no enzymes) as media and a basket speed of 100 rpm. Japanese Sinker Baskets (Part Number PSCUSBSK-JPMAG) were utilized. A 1.5 mL sample was pulled at 1 hour, 2 hours, 4 hours, 6 hours, and 8 hours (Dissolution Test 1 according to the USP monograph on Oxycodone Hydrochloride Extended-Release Tablets) and submitted for HPLC analysis. HPLC conditions were modified from the USP monograph in order to observe the release of oxycodone HCl. The HPLC conditions were as follows: Injection Volume: 30 μL; Flow Rate 1.7 mL/min; Detection: UV at 225 nm; Column Temp: 25° C.; Autosampler Temperature: ambient; Gradient: Isocratic; and Runtime: 5 minutes. The specifications for dissolution testing are provided in Tables 1-4.

In order to determine the extended release characteristics of a pill, the effect of varying the wt % of the controlled release agent (e.g., PVAc/PVP or H-HPMC) in the formulation was tested. In the initial phase of testing, PVAc/PVP was tested as a duel matrix/controlled release agent. The general formulation as provided in Tables 5 and 6 was tested for dissolution with the wt % of PVAc/PVP offset by the plasticizer.

Figure 4:
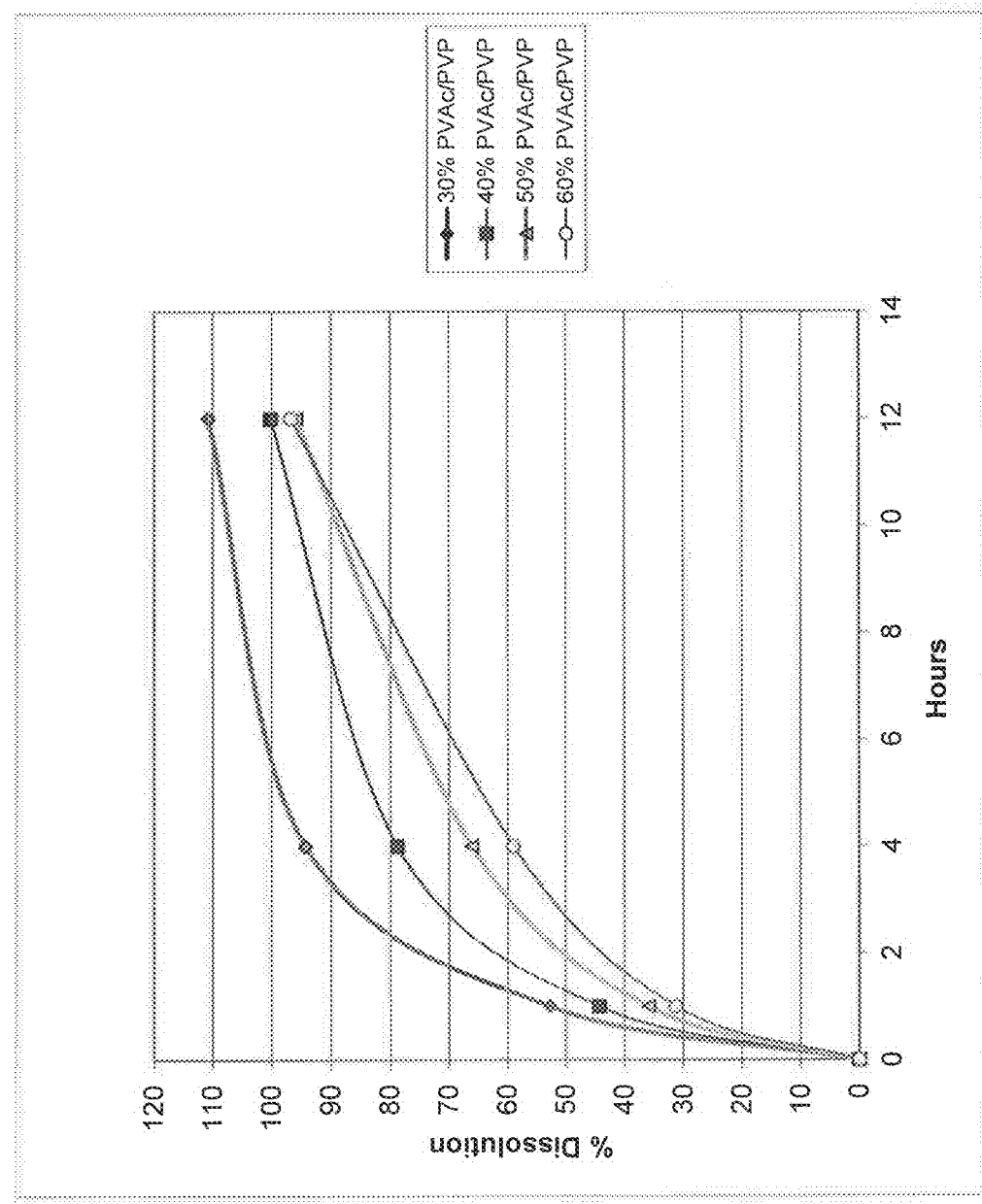
FIG. 4 shows the dissolution profiles for exemplary formulations containing different wt % amounts of PVAc/PVP (e.g., 30-60 wt %).

FIG. 4 shows the dissolution for four formulations having a different wt % of PVAc/PVP (30-60 wt. %). The higher the PVAc/PVP content, the slower the release of active substance at the 1, 4, and 12 hour time points, thus wt % of PVAc/PVP has a direct correlation to release profile.

Abuse Deterrent Testing

The abuse deterrent pills were tested for resistance to pulverizing/grinding using a coffee grinder analysis. The tested formulations contained materials mentioned in Tables 5 and 6. Three (3) pills for each specific wt % of PEO were selected and placed in a commercially available coffee grinder (Mr. Coffee®, model number IDS55). The coffee grinder was run for about 30 seconds with occasional pulsing. The grinded pills were submitted to a particle size analysis using an ATM L3P sonic sifter separator (screen size 35 Mesh) for 2 minutes. The 35 Mesh corresponds to a sieve size of 500 µm. The wt % of particles above 500 m was used as a metric for measuring abuse deterrence against pulverization and grinding for subsequent insufflation.

The combination of PVAc and PVP was tested for its application in a matrix agent for abuse deterrence in formulations mentioned in Tables 5 and 6. In formulations with more than 40%, 50%, and 60% of PVAc/PVP, less than 45% of the particles were above 500 µm after being pulverized in the coffee grinder for 30 seconds. The PVAc/PVP alone does not have enough deterrence against pulverization when it is used as a duel matrix/controlled release agent.

Example 2

Due to Example 1 having low abuse deterrence from pulverization, a separate matrix agent was needed which could act to prevent pulverization of the pill while not having a large effect on dissolution profile. PEO was selected for its ability to prevent pulverization due to entanglement of polymer chain lengths. Extended release abuse deterrent pills were manufactured according to Tables 8 and 9.

TABLE 8

Exemplary Extended Release Abuse Deterrent Pill Formulation Ranges

| Components | % Wt. |
| --- | --- |
| Active Substance | 5.0-40.0 |
| Matrix Agent (50K-150K Da) | 8.0-35.0 |
| Controlled Release Agent | 8.0-60.0 |
| Plasticizer (8k Da) | 0.0-22.0 |

TABLE 9

Exemplary Extended Release Abuse Deterrent Pill Formulation Ranges

| Components | % Wt. |
| --- | --- |
| Active Substance | 5.0-40.0 |
| Polyethylene Oxide (50K-150K Da) | 23.0-27.0 |
| Polyvinyl Acetate | 25.0-50.0 |
| Polyvinylpyrrolidone | 5.0-15.0 |
| Sodium Lauryl Sulfate | 0.1-0.75 |
| Silica | 0.01-0.2 |
| Polyethylene Glycol (8k Da) | 1.0-15.0 |
| Antioxidants | 0.0-2.0 |
| Dye | 0.0-2.0 |

Figure 5:
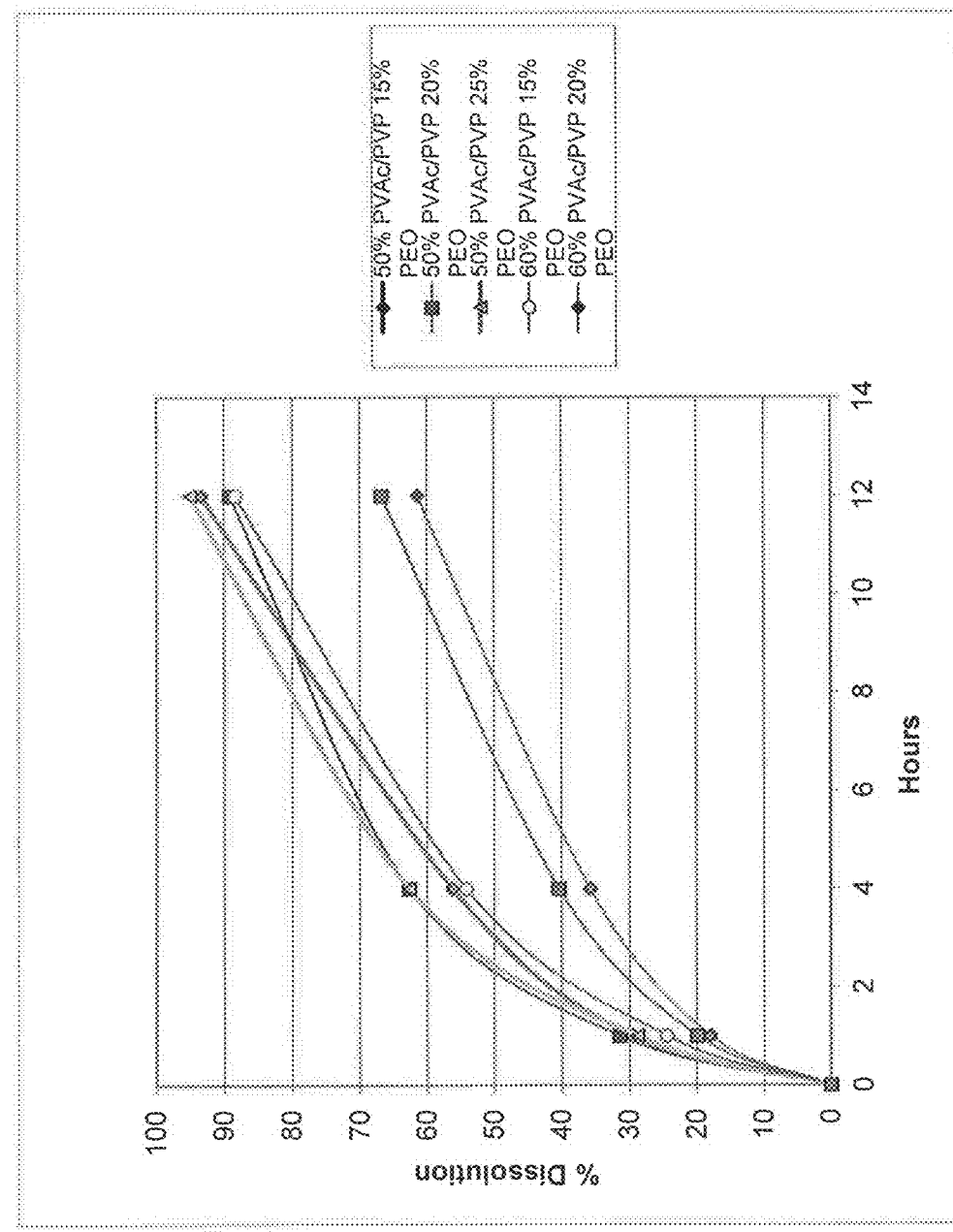
FIG. 5 shows the dissolution profiles for exemplary formulations containing different wt % amounts of 100K Dalton PEO and wt % amounts of PVAc/PVP.

The formulations for extended release abuse deterrent pills described in Tables 8 and 9 underwent the same manufacturing procedure and dissolution testing as described in Example 1. FIG. 5 shows the dissolution of six formulations containing three wt % s of 100K Dalton PEO at two wt % s of PVAc/PVP. The PVAc/PVP is believed to be the controlled release rate modifying agent for this formulation with the 100K Dalton PEO having no effect on controlled release of the drug.

Abuse Deterrent Testing

The abuse deterrent pills were tested for resistance to pulverizing/grinding using a coffee grinder analysis. The tested formulations contained materials mentioned in Tables 8 and 9. The tests were performed in the same manner as described in Example 1 and the same 500 µm particle size was used as a metric for measuring abuse deterrence against pulverization and grinding for subsequent insufflation.

The addition of 100K Dalton PEO to the abuse deterrent pills with PVAc/PVP significantly increased the percentage particles over the 500 µm size after the coffee grinder testing. This suggests that the 100K Dalton PEO helps to make the pills more abuse deterrent.

With 10-15% 100K Dalton PEO in the formulation the percentage of particles over 500 µm increased to 70-80% and if the PEO percentages were 20-25% the particles over 500 µm increased to over 80% in most cases after grinding, see Table 10. In Table 10, the PVAc/PVP and a plasticizer were adjusted to complete the rest of the formulations.

TABLE 10

Effect of 100K Dalton PEO on the Pulverization of the Pills

| 100K Dalton PEO (% in formulation) | ADF properties (% Particles >500 µm) |
| --- | --- |
| 0% | 13%-45% |
| 10%-15% | 71%-76% |
| 20%-25% | 79-95% |

The effect of 100K Dalton PEO on pulverization was independent of the PVAc/PVP wt %. The coffee grinder analysis was performed on formulations with 15% wt 100K Dalton PEO and with PVAc/PVP having a wt % varied from 38%, 50% and 60%. The percentage of particles over 500 m was between 70-75% for all three PVAc/PVP wt %, suggesting that PEO was controlling the resistance to pulverization. See Table 11.

TABLE 11

Effect of Changes in PVAc/PVP % on the Pulverization in a Formulation with 15% PEO

| PVAc/PVP (% in formulation) | ADF properties (% Particles >500 μm) |
|---|---|
| 37.89% | 71% |
| 50% | 75% |
| 60% | 73% |

The percentage of the active ingredient in the formulation was also tested to see if there would be any reduction in the pulverization of the pills with increased level of active ingredient. The test formulation contained 15 wt % 100K Dalton PEO and either 5 wt %, 20 wt % or 40 wt % active ingredient. The PVAc/PVP and plasticizer were used to complete the rest of the formulation. The effect of the dosing percentage on the pulverization level is shown in Table 12. As shown in Table 12, the percentage of the active ingredient did not affect the ADF properties of the formulation when the PEO percentage was held constant.

TABLE 12

Effect of Dosing Percentage on the Pulverization Levels

| Active Ingredient (% in formulation) | ADF properties (% Particles >500 μm) |
|---|---|
| 5% | 73-75% |
| 20% | 76% |
| 40% | 71% |

These formulations meet or exceed the metrics for abuse deterrent properties with regards to pulverization and grinding. The inclusion of 10-15 wt % of 100K Dalton PEO in the formulation results in good abuse deterrent properties and 20-25 wt % of 100K Dalton PEO in the formulation results in excellent abuse deterrent properties against insufflation.

Example 3

Testing was also performed using abuse deterrent formulations containing HPMC as a controlled release rate modifying agent. Acetaminophen was utilized as a tracer in place of oxycodone HCl for these experiments due to its availability, similar dissolution/solubility profile and cost-effectiveness. Extended release abuse deterrent pills containing acetaminophen in place of oxycodone HCl were manufactured according to the following formulation as provided in Tables 13 and 14. These were produced using the same manufacturing and dissolution method described in Example 1.

TABLE 13

Exemplary Extended Release Abuse Deterrent Pill Formulation Ranges

| Components | % Wt. |
|---|---|
| Active Substance | 5.0-40.0 |
| Matrix Agent (100K-350K Da) | 15.0-40.0 |
| Controlled Release Agent | 10.0-50.0 |
| Plasticizer (8k Da) | 0.0-40.0 |

TABLE 14

Exemplary Extended Release Abuse Deterrent Pill Formulation Ranges

| Components | % Wt. |
|---|---|
| Active Substance | 5.0-40.0 |
| Polyethylene Oxide (100K-350K Da) | 20.0-31.0 |
| Hydroxypropyl Methylcellulose | 15.0-42.0 |
| Polyethylene Glycol (8k Da) | 5.0-40.0 |
| Antioxidants | 0.0-2.0 |
| Dye | 0.0-2.0 |

Initial testing using 300K Dalton PEO with HPMC was done to test the effect of PE( ) on dissolution. The wt % of the PEO was varied while maintaining the HPMC wt %. FIG. 6 shows the dissolution profile of four formulations with varied wt % of 300K Dalton PEO (50-80 wt %). These results show very similar dissolution profiles at higher wt % 300K Dalton PEO in the formulation (i.e., 60, 70, and 80 wt %). The 50 wt % formulation exhibited a faster release profile. This experiment indicates that 300K Dalton PEO does not have a molecular weight high enough to provide controlled release of the active substance.

Additional testing was done to test the controlled release effects of varying the wt % of HPMC in the formulation while holding 300K Dalton PEO constant. Formulations were manufactured according to Tables 13 and 14. FIG. 7 shows the dissolution profile of 5 formulations with varying wt % of HPMC (30-66 wt %).

The results show very similar data points at the 1 hour time point regardless of wt % of HPMC. At the 4 hour time point, the release profile is inversely proportional to the wt % of HPMC, which ceases to change at 50 wt %. This experiment shows there is a direct correlation between wt % of HPMC and the release rate of active substance below 50 wt % of HPMC.

Abuse Deterrence Testing

The abuse deterrent pills were tested for resistance to pulverizing/grinding using a coffee grinder analysis in the same manner as described in Example 1. The tested formulations contained materials mentioned in Tables 13 and 14. The same 500 μm metric was used as a marker for abuse deterrence against pulverization and grinding for insufflation.

Abuse deterrent pills containing 300K Dalton PEO were tested for resistance to pulverizing/grinding using the coffee grinder analysis. All of the formulations containing ≥29 wt % 300K Dalton PEO have a 90% or higher weight percentage of particles over the size of 500 μm after pulverization in a coffee grinder (92%-100%). Table 15 below outlines the results.

Additional testing was done on pills that were formulated using 300K Dalton PEO with a larger final pill weight. Formulations were made with 300 mg and 400 mg pill weights and showed there was no appreciable change in the particle size distribution compared to a similar 200 mg formulation. Table 15 details the results of this experiment.

TABLE 15

Coffee Grinder Analysis for Higher Pill Weight Experiments

| Pill Weight | ADF properties (% Particles >500 μm) |
|---|---|
| 200 mg | 92%-100% |
| 300 mg | 93%-96% |
| 400 mg | 94%-98% |

The percentage of HPMC was varied to test the effect on the ability of the pill to prevent pulverization. Formulations of 29% and 60% 300K Dalton PEO were used as constants while the HPMC levels were varied. The plasticizer was used to fill the percentages of the formulations to maintain the same pill weight. It was found that the wt % of HPMC had no effect on the pulverization results. When the wt % of HPMC was varied from 5%-66% the wt % of particles greater than 500 μm following the coffee grinder analysis was 92% or higher. The results are outlined in Table 16.

TABLE 16

Effect of HPMC on Abuse deterrence properties

| Percentage of HPMC | ADF properties (% Particles >500 μm) |
| --- | --- |
| 5%-25% (60% PEO) | 95%-100% |
| 30%-66% (29% PEO) | 92%-98% |

All formulations met or exceeded the metric for abuse deterrent properties with regards to pulverization and grinding. Pills containing ≥29-60 wt % 300K Dalton PEO and 5-66 wt % HPMC as the extended release agent are difficult to pulverize or grind into a form that could be insufflated.

Example 4

Formulations using oxycodone HCl as an active substance were manufactured according to Tables 13 and 14 in a similar method described in Example 1 with a theoretical dosage of 10 mg. Three pills listed as percent active dissolved at a given time point are shown in Table 17.

TABLE 17

10 mg Oxycodone HCl Dissolution Data

|  | Average | Pill 1 | Pill 2 | Pill 3 |
| --- | --- | --- | --- | --- |
|  | 1 Hour | | | |
| Actual | 25.83 | 25.077 | 27.657 | 24.753 |
| RLD Specification | 18%-28% | | | |
|  | 4 Hours | | | |
| Actual | 64.46 | 62.229 | 68.13 | 63.023 |
| RLD Specification | 44%-65% | | | |
|  | 12 Hours | | | |
| Actual | 93.20 | 90.976 | 93.664 | 94.961 |
| RLD Specification | 77%-95% | | | |

The results show the average percent of active dissolved at each time point is within specification of the Reference List Drug for a 10 mg extended release oxycodone HCl pill.

Similarly, a formulation utilizing a theoretical dosage of 80 mg oxycodone HCl was made in accordance with Tables 13 and 14. Three pills were subjected to dissolution testing listed as percent active dissolved at the given time point, shown in Table 18.

TABLE 18

80 mg Oxycodone HCl Dissolution Data

|  | Average | Pill 1 | Pill 2 | Pill 3 |
| --- | --- | --- | --- | --- |
|  | 1 Hour | | | |
| Actual | 38.17 | 36.406 | 38.629 | 39.473 |
| USP Specification | 31%-51% | | | |
|  | 4 hours | | | |
| Actual | 70.91 | 66.43 | 71.54 | 74.772 |
| USP Specification | 61%-81% | | | |
|  | 12 hours | | | |
| Actual | 92.06 | 87.937 | 91.308 | 96.938 |
| USP Specification | >85% | | | |

These results show the dissolution at the 1, 4, and 12 hour time points for the 80 mg formulation listed in Tables 13 and 14 are within the criteria defined by the USP for an 80 mg oxycodone HCl ER tablet.

Abuse Deterrence Testing

The abuse deterrent pills were tested for resistance to pulverizing/grinding using a coffee grinder assay in the same manner as described in Example 1. The tested formulations contained materials mentioned in the rest of this example containing oxycodone HCl as the active substance. The same 500 μm particle size was used as a metric for measuring abuse deterrence against pulverization and grinding for subsequent insufflation It was found that the abuse deterrent pills performed the equal to or better than previous pulverization tests performed in Examples 1-3. The 10 mg and 80 mg dosage pills were tested to confirm the ability to prevent abuse via pulverization. Both 100K Dalton PEO and 300K Dalton PEO were also tested using oxycodone HCl as the active ingredient. It was found at all of the pills with these formulations and oxycodone as the API had more than 70% of the weight percentage of particles over the size of 500 μm after pulverization in a coffee grinder, see Table 19.

TABLE 19

Oxycodone HCl pill Pulverization results.

| Experiment | ADF properties (% Particles >500 μm) |
| --- | --- |
| 10 mg Pill | 85%-96% |
| 80 mg Pill | 75%-93% |

Exemplary oxycodone I-IC formulations are provided in FIGS. 8-11. FIG. 8 shows exemplary formulations having 10 mg to 80 mg active substance and 100K Dalton PEO. The wt % values for PEO, PVAc/PVP (combined and separate) and PEG listed in FIG. 8 may be varied up to +/−1% and +/−3% within each formulation. For example, the 10 mg dosage form may contain about 23 wt % to about 27 wt % PEO, about 53 wt % to about 57 wt % PVAc/PVP, and about 12 wt % to about 16 wt % PEG. FIG. 9 shows exemplary formulations having 5 mg to 40 mg active substance and 100K Dalton PEO. The wt % values for PEO, PVAc/PVP (combined and separate) and PEG listed in FIG. 9 may also be varied up to +/−1% and +/−3% within each formulation. FIG. 10 shows exemplary formulations having 5 mg to 80 mg active substance and 300K Dalton PEO. The wt % values for PEO, HPMC and PEG listed in FIG. 10 may be varied up to +/−1% and +/−3% within each formulation.

Additional oxycodone HCl formulations having 10 mg and 80 mg active substance were prepared having varying amounts of excipients as provided in FIG. 11. The formulations were evaluated for dissolution profile and abuse deterrent properties, as described above. Formulations exhibiting an acceptable dissolution profile and abuse deterrent property are identified (e.g., experiments 5, 9, 11, 20 and 23) in FIG. 11. Formulations comprising PEO, PVAc/PVP or HPMC, and PEG which vary up to +/−1% and +/−3% within each formulation are contemplated by the present disclosure. For example, an 80 mg dosage form may contain about 27 wt % to about 31 wt % 300K Dalton PEO, about 35 wt % to about 39 wt % HPMC and about 27 wt % to about 31 wt % PEG.

Example 5

Active substance dose dumping of extended release dosage forms in ethanol is another way drug products can be abused. With regards to dose dumping in alcohol, to be classified as abuse deterrent a drug product should be able to resist dumping the active substance in a media containing alcohol. Dose dumping is commonly defined as the "unintended, rapid drug release in a short period of time of the entire amount or a significant faction of the drug contained in a modified release dosage form." To test a real life scenario, a media was created which consisted of 90% simulated gastric fluid (the oxycodone HCl dissolution media) and 10% ethanol or 810 mL Simulated Gastric Fluid (SGF) and 90 mL ethanol (EtOH). This is an equivalent environment to the stomach of a person who has consumed 7.22 fluid ounces of 80 proof alcohol. Rapid drug release was defined as a significant increase in dissolved drug at the 60 minute time point. Experiments were based on formulations detailed in Tables 8, 9, 13 and 14.

Results for the PEO and PVAc/PVP matrix tablets show a negligible difference in dissolution in alcoholic environments. Reference Table 20 for results. The largest increase in dissolution is only 1.82%. The formulations containing PEO and HPMC show only a slightly reduced amount of dissolved active substance at the 60 minute time point. These results suggest the presence of alcohol may actually decrease the release rate of active substance. The formulation of the present disclosure is not subject to alcohol dose dumping. The formulation of the present disclosure exhibits less than about a 50% increase, or about a 40% increase, or about a 30% increase, or about a 20% increase, or about a 10% increase, or about a 5% increase of active substance released in a simulated alcoholic gastric fluid environment. The formulation of the present disclosure is also not subject to ineffective release in alcoholic environments.

TABLE 20

Extended Release Alcohol Dose Dumping Study

| Media | Pill 1 | Pill 2 | Pill 3 | Average | Variance from Baseline |
|---|---|---|---|---|---|
| PEO/PVAc/PVP Dissolution at 60 Minutes | | | | | |
| 100% SFG | 22.81 | 25.09 | 25.54 | 24.48 | |
| 90% SGF: 10% EtOH | 25.03 | 25.31 | 25.91 | 25.42 | 0.94 |
| 100% SFG | 16.29 | 19.24 | 18.45 | 17.99 | |
| 90% SGF: 10% EtOH | 19.33 | 20.31 | 19.80 | 19.81 | 1.82 |
| 100% SFG | 27.71 | 25.66 | 28.95 | 27.44 | |
| 90% SGF: 10% EtOH | 26.33 | 25.94 | 26.68 | 26.32 | −1.13 |
| PEO/HPMC Dissolution at 60 Minutes | | | | | |
| 100% SFG | 25.077 | 27.657 | 24.753 | 25.83 | |
| 90% SGF: 10% EtOH | 23.106 | 23.661 | 22.741 | 23.17 | −2.66 |
| 100% SFG | 25.248 | 27.483 | 28.865 | 27.20 | |
| 90% SGF: 10% EtOH | 20.808 | 23.64 | 23.347 | 22.60 | −4.60 |

Extraction Example

The inclusion of one or more dyes in a drug formulation is one method to render a formulation abuse deterrent. Significant discoloration of an extraction product from a formulation subject to abuse can discourage a potential abuser from using (e.g., injecting or ingesting) the extraction product. A study was conducted to investigate the effect of dyes in the formulations of the present disclosure. Extraction products from whole or cut formulations were visually inspected to determine abuse deterrence following alcohol extraction, and also following subsequent filtration.

Color is one identifying characteristic of commercial drug products. Color can be applied to the dosage form in two ways: dye or coating. High potency alcohol (i.e., ≥190 proof (95%)) is one extraction solvent that can be used by abusers for APIs which are insoluble in water or in order to separate the API from other water soluble excipients. Dyes or coatings can potentially be used to alter the physical appearance of the extracted solution of drug product (i.e., turn the resulting solution a noticeable color).

In this study, 190 proof ethanol was utilized as an extraction solvent. A commercially available coffee filter was used to filter out any particulate matter of several drug products. The resulting solution was analyzed for physical appearance. The difference in physical appearance (if any) between drug products which are dyed or coated was evaluated.

Experimental

Oxycodone 10 mg and 80 mg (Extended Release) as described in the present disclosure, Opana® ER 5 mg (reformulated) (Endo Health Solutions); Opana® ER 40 mg (reformulated) (Endo Health Solutions); OxyContin® 10 mg (reformulated) (Purdue Pharma); OxyContin® 40 mg (reformulated) (Purdue Pharma); OxyContin® 60 mg (reformulated) (Purdue Pharma); OxyContin® 80 mg (reformulated) (Purdue Pharma). A summary of all of the samples tested is provided in the table below.

TABLE 21

List of Samples Tested
Dosage Units Descriptions

| Sample | Sample Name | Manufac. Process | Manufac. Process Color | API | Release Timeframe |
|---|---|---|---|---|---|
| 4 | Present Disclosure ER 10 mg | Extrusion | Dye | Oxycodone | Extended |
| 5 | Present Disclosure ER 80 mg | Extrusion | Dye | Oxycodone | Extended |
| 6 | Opana ® ER 5 mg | Extrusion | Coating | Oxymorphone | Extended |
| 7 | Opana ® ER 40 mg | Extrusion | Coating | Oxymorphone | Extended |
| 8 | OxyContin ® 10 mg | Compress & Cure | Coating | Oxycodone | Controlled |
| 9 | OxyContin ® 40 mg | Compress & Cure | Coating | Oxycodone | Controlled |
| 10 | OxyContin ® 60 mg | Compress & Cure | Coating | Oxycodone | Controlled |
| 11 | OxyContin ® 80 mg | Compress & Cure | Coating | Oxycodone | Controlled |

The formulations of the samples of the present disclosure tested, i.e., samples 4 and 5, are provided in the table below.

TABLE 22

Formulations of Samples Tested

| Component | Sample 4 | Sample 5 |
|---|---|---|
| Oxycodone HCl | 5.00% | 33.33% |
| PEO, 100K Daltons | 40.00% | 40.00% |
| HPMC, K100M | 37.50% | 20.00% |
| PEG, 8K Daltons | 15.75% | 4.67% |
| Citric Acid | 1.00% | 1.00% |
| Dye | 0.75% | 1.00% |
| Total weight | 200 mg | 240 mg |
| Release characteristics | ER | ER |

In additional embodiments of the present disclosure, the amount of active substance in the formulation can range from about 0.50 Wt % to about 40 Wt %. Particularly, the amount of active substance in the formulation may range from about 1.0 Wt % to about 35 Wt %, or from about 5.0 Wt % to about 33 Wt %. In additional embodiments of the present disclosure, the amount of plasticizer (e.g., PEG) can range from about 0.25 Wt % and about 20 Wt % plasticizer.

For each sample, both whole and cut dosage units were tested. For whole dosage units, two (2) whole dosage units were placed in a 25 mL Erlenmeyer flask containing 10 mL of EtOH. For cut dosage units, all cut pieces of the dosage unit were placed in similar flasks. Cut dosage units were cut into about 8 pieces using diagonal pliers. Each flask was sealed with parafilm and shaken on a platform shaker for at least 10 hours at about 150 rpm. The resulting solution was filtered through a coffee filter to remove any particulate matter. The filtered solution was collected in a 50 mL Nessler color comparison tube. After 30 minutes, each sample tube was visually examined for color (if any), clarity/turbidity, and if any noticeable difference in filtered solution volume exists (i.e., a significant decrease from the original 10 mL EtOH). The results for the whole and cut dosage units are provided in the two tables below.

TABLE 23

Whole Dosage Unit Extraction Data
Visual Examination - Whole Dosage Units

| Sample | Sample Name | Color Change | Color Observed | Intensity | Notes (clarity/turbidity, volume change, etc.) |
|---|---|---|---|---|---|
| 4 | Present Disclosure ER 10 mg | Yes | Blue | Dark | Clear, ~3 mL volume decrease |
| 5 | Present Disclosure ER 80 mg | Yes | Green | Dark | Clear, ~4 mL volume decrease |
| 6 | Opana ® ER 5 mg | No | None | None | Clear, no volume change |
| 7 | Opana ® ER 40 mg | Yes | Yellow | Faint | Clear, no volume change |
| 8 | OxyContin ® 10 mg | Yes | White | Faint | Slightly turbid, no volume change |
| 9 | OxyContin ® 40 mg | Yes | White | Faint | Slightly turbid, no volume change |
| 10 | OxyContin ® 60 mg | Yes | Red | Faint | Slightly turbid, no volume change |
| 11 | OxyContin ® 80 mg | Yes | Blue | Faint | Slightly turbid, no volume change |

TABLE 24

Cut Dosage Unit Extraction Data
Visual Examination - Cut Dosage Units

| Sample | Sample Name | Color Change | Color Observed | Intensity | Notes (clarity/turbidity, volume change, etc.) |
|---|---|---|---|---|---|
| 4 | Present Disclosure ER 10 mg | Yes | Blue | Dark | Clear, ~3 mL volume decrease |
| 5 | Present Disclosure ER 80 mg | Yes | Green | Dark | Clear, ~4 mL volume decrease |
| 6 | Opana ® ER 5 mg | No | None | None | Clear, ~1 mL volume decrease |
| 7 | Opana ® ER 40 mg | Yes | Yellow | Faint | Clear, ~1 mL volume decrease |
| 8 | OxyContin ® 10 mg | Yes | White | Faint | Slightly turbid, ~1 mL volume decrease |
| 9 | OxyContin ® 40 mg | Yes | White | Medium | Turbid, ~1 mL volume decrease |
| 10 | OxyContin ® 60 mg | Yes | Red | Medium | Turbid, ~2 mL volume decrease |
| 11 | OxyContin ® 80 mg | Yes | Blue | Faint | Turbid, slight volume change |

During filtration, samples passed through the filter at various rates. For example, samples 6-11 took approximately 20 seconds for the entire volume to completely pass through the coffee filter. Samples 4 and 5 took approximately 60 minutes for the entire volume to completely pass through the coffee filter. After filtration, samples 4-5 were uniform in color after sitting for approximately 30 minutes, while samples 8-11 had significant sediment at the bottom of the comparison tubes. Samples 6 and 7 had no noticeable sediment but were significantly less colored than the batches of the present disclosure.

Approximately 5 mL of the filtrate from each cut dosage form sample was passed through a 25 mm, 0.2 μm PTFE Titan syringe filter (Scientific Resources, Inc. Cat No. 42225-PC, Lot 709029003054). Each resulting solution was then assigned a number according to a scale of 0-5, with 0 (zero) representing a sample with no color and 5 representing a sample with a dark, significant color, (0—no color; 1—faint; 2—light; 3—medium; 4—brilliant; and 5—dark). Samples with at least light color, including dark coloration, can deter potential abusers from injecting or ingesting the filtered extract (e.g., colors 2 and above, 3 and above, 4 and above, or 5). The table below shows the color number assignments for the syringe filtered cut dosage unit solutions.

TABLE 25

Cut Dosage Unit Color Numbers
Visual Examination - Cut Dosage Units

| Sample | Sample Name | Color Number |
|---|---|---|
| 4 | Present Disclosure ER 10 mg | 5 |
| 5 | Present Disclosure ER 80 mg | 5 |
| 6 | Opana ® ER 5 mg | 0 |
| 7 | Opana ® ER 40 mg | 1 |
| 8 | OxyContin ® 10 mg | 0 |
| 9 | OxyContin ® 40 mg | 0 |
| 10 | OxyContin ® 60 mg | 0 |
| 11 | OxyContin ® 80 mg | 0 |

In some embodiments, the formulation of the present disclosure incorporates the dye throughout the entire dosage unit as opposed to incorporating the dye only in a coating. The dye can be water soluble, alcohol soluble or both. The dye can have a solubility in water, alcohol or both that is greater than about 0.01 g/100 mL, about 0.1 g/100 mL, about 1 g/100 mL or about 10 g/100 mL. Traditional drug formulation dyes are not soluble, or significantly soluble, in water, alcohol or both. They are often formulated into the coatings of the drug formulations. In some embodiment, the dyes are water soluble, alcohol soluble or both, and are dyes that are approved for, or considered acceptable, for oral administration. In some instances, the solubility of the dye in alcohol is important because of the potential for compounding effects of, and interactions associated with, consuming both alcohol and the extracted API.

The following table lists the relative solubility of exemplary components of a formulation. A number of different dyes are listed along with their solubility information taken from the various literature sources and tested experimentally (200 proof ethanol and filtered through a 0.22 micrometer PTFE filter).

TABLE 26

General Solubility of Exemplary Components

| Exemplary Components | Water Solubility | Alcohol Solubility (Literature) | Alcohol Solubility (tested) |
|---|---|---|---|
| Oxycodone HCl | Yes | Yes | N/A |
| Polyethylene Oxide | Yes | No | N/A |
| Polyethylene Glycol | Yes | Yes | N/A |
| Hydroxypropylmethylcellulose | Yes | No | N/A |
| Microcrystalline Cellulose | No | No | N/A |
| Lactose | Yes | No | N/A |
| Blue #1 | Yes | Yes | Yes |
| Blue #2 | Yes | Yes | Yes |
| Yellow #5 | Yes | Yes | Yes |
| Yellow #6 | Yes | Yes | Yes |
| Red #40 | Yes | Yes | Yes |
| Lake Dyes | No | No | N/A |

The sediment observed at the bottom of the comparison tubes of the OxyContin® batches (samples 8-11) is indicative of a suspension rather than a solution. Typically, suspensions can be centrifuged or filtered to obtain a more clear solution (and in some cases, a colorless solution). Conversely, solutions cannot be further centrifuged or filtered using a common household coffee filter or a readily available syringe filter to obtain a more clear solution because the dye is completely dissolved in the solution. Dyed formulations can provide an additional mechanism of abuse deterrence than coated formulations.

The amount of dye present in the formulation can be an amount that produces an extract or a filtered extract using water, alcohol or a combination of both with a color that is greater than 0, or greater than 1, or greater than 2, or greater than 3 or greater than 4 on the visual scale disclosed, or similar scale. The amount of dye can vary depending on the formulation and components present. In some embodiments, the formulation can contain at least 0.1% dye, at least 0.2% dye, at least 0.3% dye, at least 0.4% dye, at least 0.5% dye, at least 0.6% dye, at least 0.7% dye, at least 0.8% dye, at least 0.9% dye, at least 1.0% dye, at least 1.5% dye, at least 2.0% dye, or any range of these values (e.g., between about 0.1% and about 1.0% dye).

It was also observed that a volume change occurred (~3-4 mL decrease) for samples 4 and 5 following extended filtration time. Certain excipients (e.g., HPMC) can cause the resulting solution to become too viscous to fully pass through a coffee filter. Additional abuse deterrence (e.g., extended extraction time and volume loss) can be obtained by formulations including HPMC, or equivalents.

Additional Exemplary Formulations

Additional exemplary formulations of the present disclosure are provided in the tables below.

TABLE 27

Additional Exemplary Formulations

| Component | 15 mg API | 20 mg API | 30 mg API | 40 mg API | 60 mg API |
|---|---|---|---|---|---|
| Oxycodone HCl | 7.50% | 10.00% | 15.00% | 20.00% | 30.00% |
| PEO, 100K Daltons | 40.00% | 40.00% | 40.00% | 40.00% | 40.00% |
| HPMC, K100M | 33.00% | 31.00% | 29.00% | 29.00% | 28.00% |
| PEG, 8K Daltons | 17.50% | 17.85% | 14.60% | 9.25% | 0.25% |
| Citric Acid | 1.00% | 1.00% | 1.00% | 1.00% | 1.00% |
| Dye | 1.00% | 0.15% | 0.40% | 0.75% | 0.75% |
| Total weight | 200 mg | 200 mg | 200 mg | 200 mg | 200 mg |
| Release characteristics | ER | ER | ER | ER | ER |

TABLE 28

Additional Exemplary Formulations

| Component | 10 mg API | 80 mg API |
|---|---|---|
| Oxycodone HCl | 4.0-6.0% | 32.0-35.0% |
| PEO, 100K Daltons | 38.0-42.0% | 38.0-42.0% |
| HPMC, K100M | 36.0-39.0% | 18.0-22.0% |
| PEG, 8K Daltons | 14.0-17.0% | 4.0-6.0% |
| Citric Acid | 0.8-1.2% | 0.8-1.2% |
| Dye | 0.6-0.9% or 0.5-1.0% | 0.8-1.2% or 0.5-1.5% |
| Release characteristics | ER | ER |

TABLE 29

Additional Exemplary Formulations

| Component | | | | | |
|---|---|---|---|---|---|
| Hydrocodone Bitartrate | 6.0-9.0% | 8.0-12.0% | 13.0-17.0% | 18.0-22.0% | 28.0-32.0% |
| PEO, 100K Daltons | 38.0-42.0% | 38.0-42.0% | 38.0-42.0% | 38.0-42.0% | 38.0-42.0% |
| HPMC, K100M | 31.0-35.0% | 29.0-33.0% | 27.0-31.0% | 27.0-31.0% | 26.0-30.0% |
| PEG, 8K Daltons | 16.0-19.0% | 16.0-19.0% | 13.0-16.0% | 8.0-11.0% | 0.2-0.3% |
| Citric Acid | 0.8-1.2% | 0.8-1.2% | 0.8-1.2% | 0.8-1.2% | 0.8-1.2% |
| Dye | 0.8-1.2% or 0.75-1.25% | 0.1-0.3% or 0.1-0.5% | 0.3-0.5% or 0.3-0.8% | 0.6-0.9% or 0.5-1.0% | 0.6-0.9% or 0.5-1.0% |
| Release characteristics | ER | ER | ER | ER | ER |

TABLE 30

Additional Exemplary Formulations

| Component | | | | | |
|---|---|---|---|---|---|
| Hydromorphone HCl | 6.0-9.0% | 8.0-12.0% | 13.0-17.0% | 18.0-22.0% | 28.0-32.0% |
| PEO, 100K Daltons | 38.0-42.0% | 38.0-42.0% | 38.0-42.0% | 38.0-42.0% | 38.0-42.0% |
| HPMC, K100M | 31.0-38.0% | 29.0-35.0% | 27.0-31.0% | 27.0-31.0% | 26.0-30.0% |
| PEG, 8K Daltons | 16.0-19.0% | 16.0-19.0% | 13.0-16.0% | 8.0-11.0% | 0.2-5.0% |
| Citric Acid | 0.8-1.2% | 0.8-1.2% | 0.8-1.2% | 0.8-1.2% | 0.8-1.2% |
| Dye | 0.8-1.2% or 0.75-2.25% | 0.1-0.3% or 1.0-2.5% | 0.3-0.5% or 0.4-2.0% | 0.6-0.9% or 0.5-2.5% | 0.6-0.9% or 0.5-4.5% |
| Release characteristics | ER | ER | ER | ER | ER |

Cutting Force Example

Figure 12:
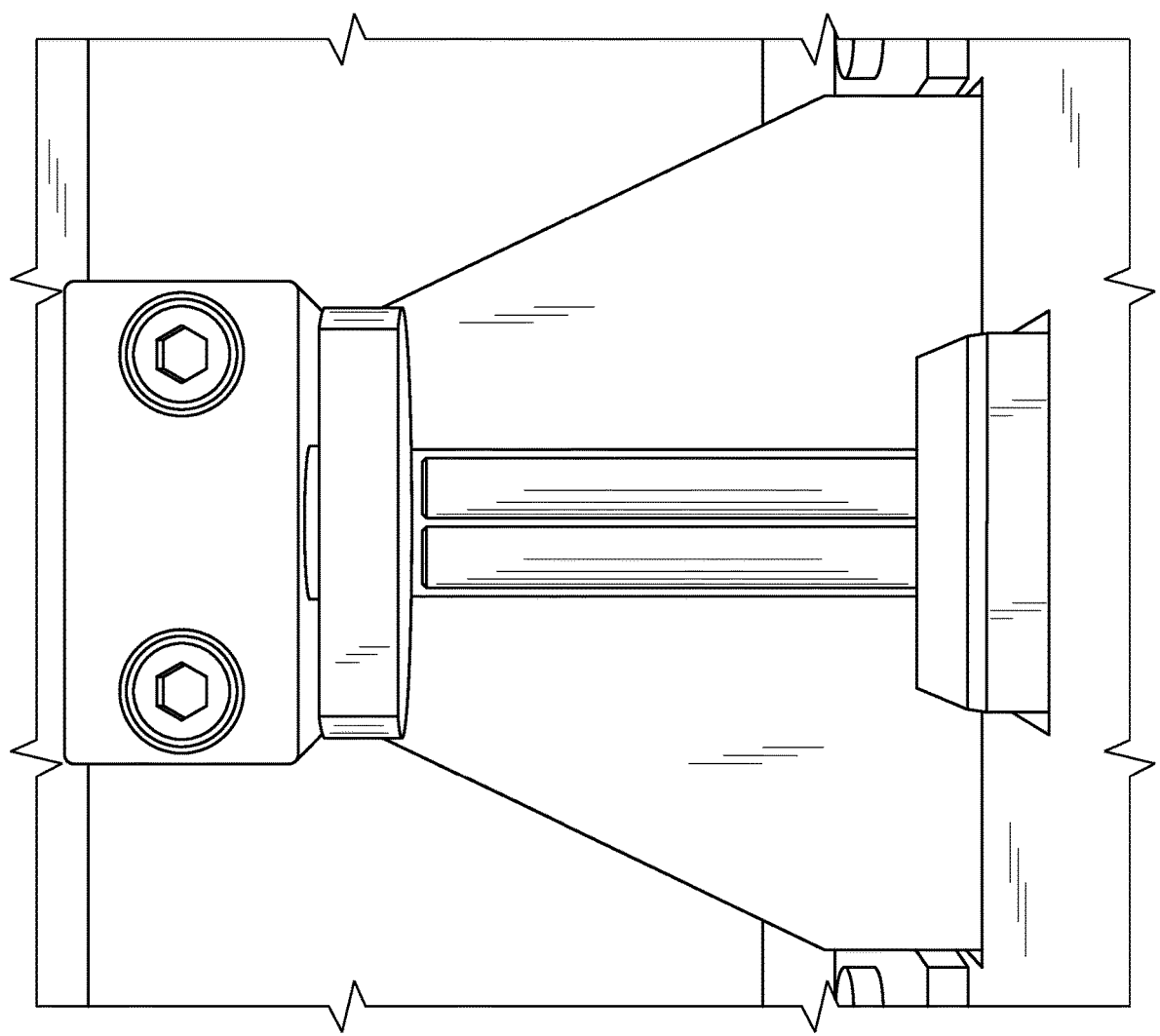
FIG. 12 shows equipment capable of executing traditional "tablet breaking force" analysis.

The existing methodology used to evaluate abuse deterrence with regards to the cutting or breaking of a dosage form is based on the USP "tablet breaking force" test. This test defines "tablet breaking force" as the force required to cause tablets to fail (i.e., break) in a specific plane. The USP describes the test as follows "[t]he tablets are generally placed between two platens, one of which moves to apply sufficient force to the tablet to cause fracture. The platens should be parallel. Their faces should be polished smooth and precision-ground perpendicularly to the direction of movement. Perpendicularity must be preserved during platen movement, and the mechanism should be free of any bending or torsion displacements as the load is applied. The contact faces must be larger than the area of contact with the tablet." FIG. 12 shows equipment capable of executing traditional "tablet breaking force" analysis.

The USP further explains the applications of tablet breaking force and why it is utilized in the industry. "Tablets must be able to withstand the rigors of handling and transportation experienced in the manufacturing plant, in the drug distribution system, and in the field at the hands of the end users (patients/consumers). Manufacturing processes such as coating, packaging, and printing can involve considerable stresses, which the tablets must be able to withstand. For these reasons, the mechanical strength of tablets is of considerable importance and is routinely measured." The intent of these applications is for traditional formulations which may be subjected to forces which could break the tablets (i.e., vigorous shaking in a tablet bottle). The intent is not to address abuse deterrence potential. Furthermore, this test is only applicable to and instructive to evaluate tablet formulations. The test is not applicable to or instructive to evaluate pill, or other formulations, prepared by extrusion methodologies.

Figure 13:
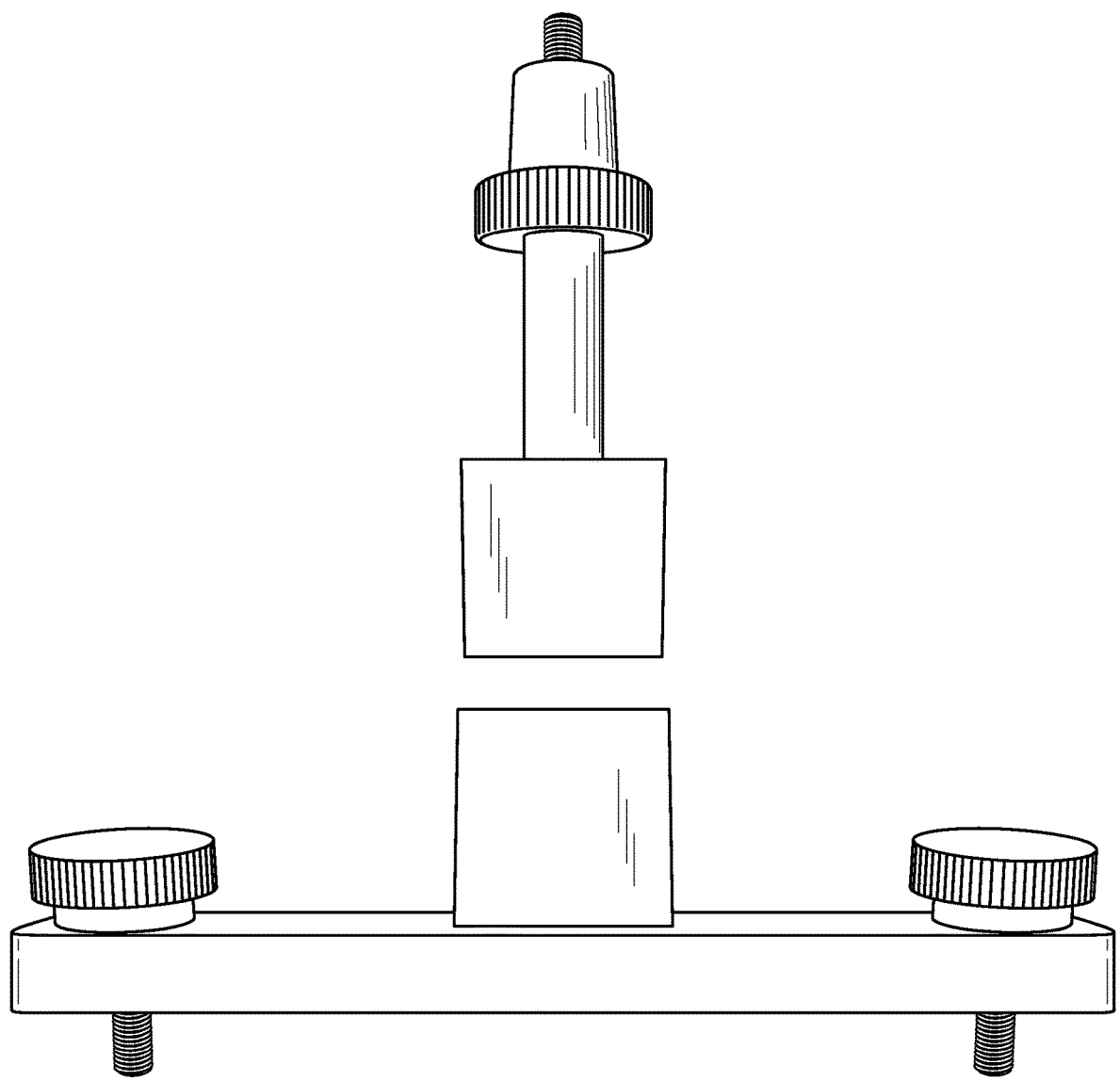
FIG. 13 shows one view of equipment capable of executing a "cutting force" analysis including a fracture wedge set attachment used to mimic common kitchen scissors.
Figure 14:
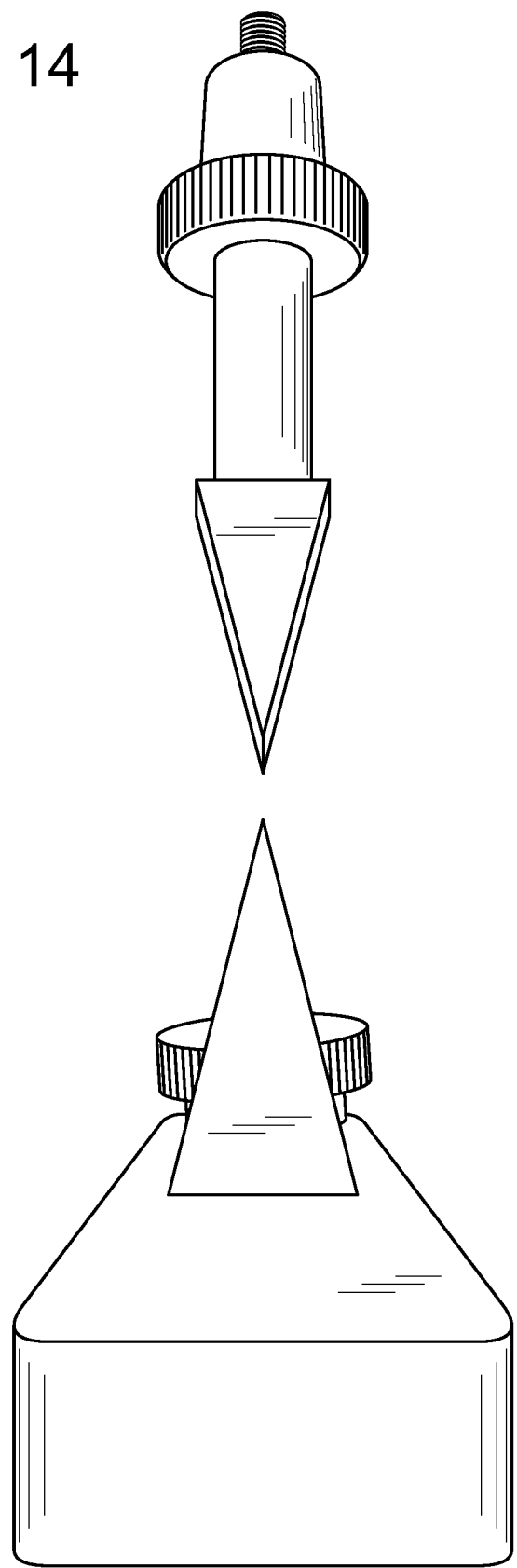
FIG. 14 shows another view of equipment capable of executing a "cutting force" analysis including a fracture wedge set attachment used to mimic common kitchen scissors.
Figure 18:
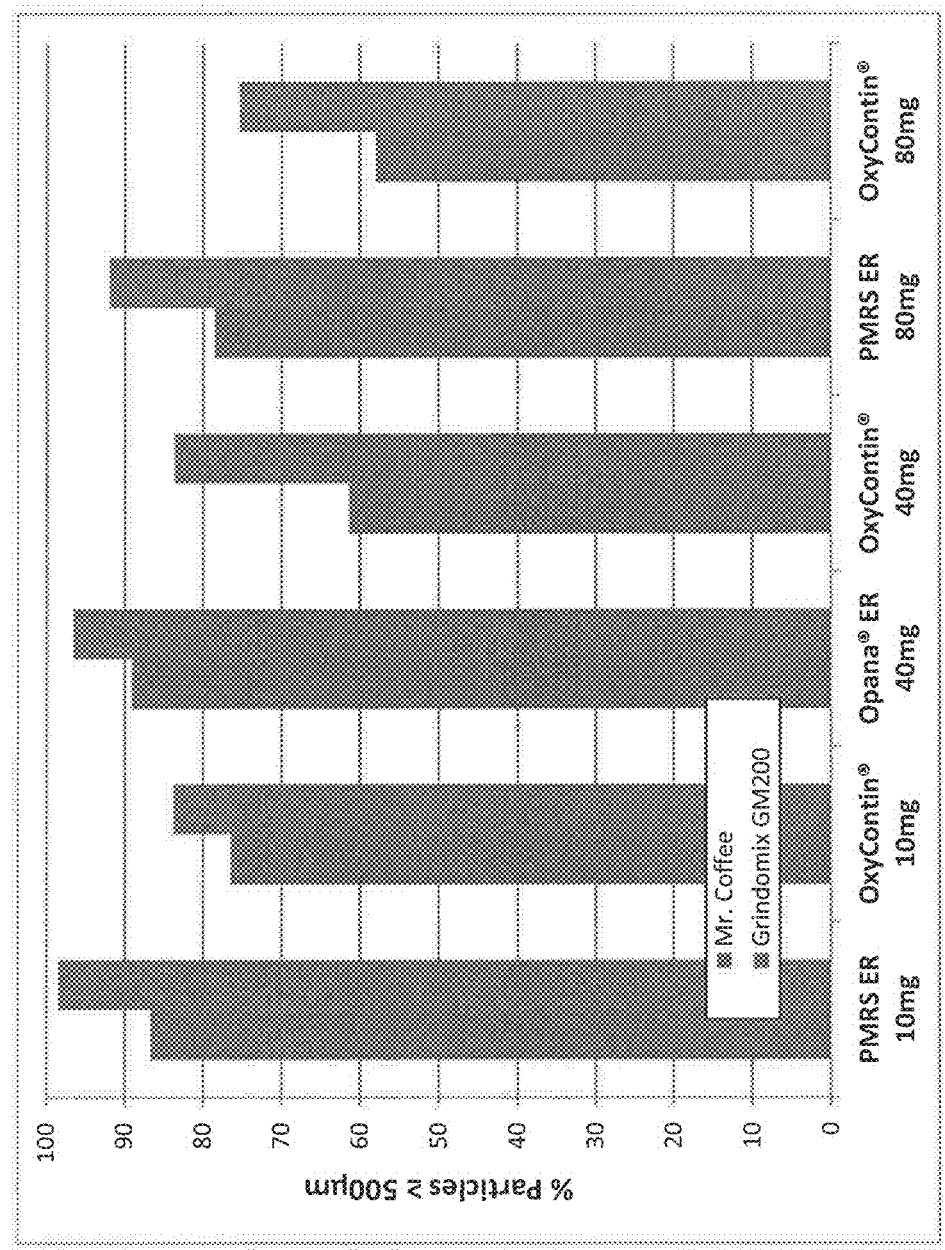
FIG. 18 shows a representation of particle size results (%≥500 μm) when comparing the tested Extended Release (ER) CII narcotic drug products between manufacturers/dosages.

In formulations utilizing excipients such as PEO, and using such excipients in an extrusion process, the parameter "tablet breaking force" does not apply. For example, the long molecular chain lengths of the PEO (e.g., 100,000 Daltons-7,000,000 Daltons) cause the drug product (relative to other traditional drug products) to be flattened, but never actually "fail" (i.e., break) when applying "tablet breaking force" in the traditional sense. The traditional application of "tablet breaking force" needs to be modified to evaluate formulations containing malleable excipients (such as PEO) for the "cutting force" of the dosage form, specifically dosage forms which are intended to deter abuse. The modification of the traditional "tablet breaking force" test presented in this study consists of a change from the "platens" utilized to cause the dosage forms to "fail" (i.e., break), namely from contact faces "larger than the area of contact with the tablet" to sharp planes which mimic commonly used tools for abuse. FIGS. 13, 14 and 15 show reference attachments including a fracture wedge set (used to mimic common kitchen scissors, FIGS. 13 and 14 showing different views of the same set) and a razor blade (FIG. 15).

The purpose of this study was to perform and summarize the cutting force needed to cut different formulations of CII narcotic drug products. Texture analysis is the mechanical testing of pharmaceutical products in order to measure their physical properties. A Texture Analyzer XT2i can perform testing of numerous physical properties of pharmaceutical products, including cutting force. The cutting force needed to cut several different formulations of CII narcotic drug products utilizing different attachments on a Texture Analyzer (TE37) was investigated. Multiple tools were utilized to cut drug products with the intent of abuse including two attachments which mimic readily available tools used for abuse (e.g., a razor blade and kitchen scissors). The cutting force for all evaluated drug products was evaluated with each attachment.

Experimental

The samples tested include those samples listed in Table 21. The formulations of the samples of the present disclosure tested are listed in Table 13 and 14. The Texture Analyzer, Model XT2i HR was operated at the following conditions: Pre Test Speed: 1 mm/s; Test Speed: 0.25 mm/s; Post Test Speed: 10 mm/s; Distance: 99.9% (% Strain); Trigger Type: Auto (Force=0.2N) and Break Detect: Off. A sample size of N=10 was used for each sample per cutting attachment. The cutting force results of the CII narcotic drug products utilizing both cutting attachments (razor blade and fracture wedge set) were determined. FIG. 16 shows the cutting force data tables for the razor blade and the fracture wedge set.

The individual maximum cutting force needed to cut any tested CII narcotic drug products utilizing the razor blade was 142 Newtons (N) (sample 7). The highest average cutting force needed to cut any tested CII narcotic drug products utilizing the razor blade was 131N (sample 7). The individual maximum cutting force needed to cut any tested CII narcotic drug products utilizing the fracture wedge set was 163N (sample 6). The highest average cutting force needed to cut any tested CII narcotic drug products utilizing the fracture wedge set was 156N (sample 6).

All of the tested CII narcotic drug products can indeed be cut, and therefore potentially be abused, with force which is substantially lower than what has been reported using the breaking strength test or equivalent (>500N, See U.S. Pat. No. 8,309,060) utilizing conventional means (i.e., common kitchen scissors or a razor blade). "Flattening" the tablets utilizing forces >500N (with traditional "tablet breaking force" definitions) does not address abuse deterrence potential in the tested CII narcotic drug products.

In one embodiment, the formulation of the present invention exhibits a cutting strength (i.e., force needed to cut the formulation) of greater than about 40 N, about 50 N, about 60 N, about 70 N, about 80 N, about 90 N, about 100 N, about 110 N, about 120 N, or about 130 N, or any range of these values (e.g., between about 40 N and about 120 N), as tested by either the Cutting Force-Razor Blade test or by the Cutting Force—Fracture Wedge Set test, or both.

Samples 4 and 5 of the present disclosure exhibit improved cutting strength compared to the compress-and-cure samples (i.e., samples 8-11). Samples prepared via a compress-and-cure procedure undergo dry mixing of the components only. These components are then compressed into a dosage form, and placing on a drying pan which applies heat to the dosage form. It is believed that compress-and-cure dosage forms are not melted or similarly liquefied to create significant homogeneity within the dosage form as compared to extrusion based procedures. The dosage formulations of the present invention are prepared by extrusion and, therefore, possess significant homogeneity as a result of the extrudate mixing within the extruder under melt flow conditions. The extrudate experiences high shear forces that produce the mechanical energy needed to ensure the required hardness and strength are achieved. The high shear forces can act on select components, for example PEO, to transform them into matrices that exhibit increased strength and stability.

Grinding Example

The purpose of this study was to perform and summarize the grinding potential of different formulations of CII narcotic drug products. The Retsch Knife Mill GRINDOMIX GM200 was utilized to mimic a commercially available coffee grinder (Mr. Coffee®) in order to grind CII drug products into a particle size that is suitable for intranasal abuse (insufflation). A commercially available coffee grinder was also evaluated for comparison purposes. Particle size analysis was conducted utilizing an ATM L3P Sonic Sifter, utilizing a 500 micrometer (µm) particle size sieve (35 mesh). For the purposes of this study, any particles less than 500 µm in diameter were considered suitable for intranasal abuse. It is generally accepted as an industry standard that any particle greater than 500 µm in diameter cannot be sufficiently absorbed by the blood vessels in the nasal passages.

The Retsch Knife Mill GRINDOMIX GM200 utilizes a circular blade attachment to mimic commercially available coffee grinders. The GM200 has a top speed of 10,000 revolutions per minute (rpm), while commercially available coffee grinders have a top speed of approximately 20,000 rpm (an approximate two-fold increase in speed when comparing the GM200 to a Mr. Coffee® grinder). However, the approximate two-fold increase in blade diameter (118 mm vs. 60 mm, when comparing the GM200 to a Mr. Coffee® grinder, respectively) compensates for the approximate twofold decrease in top speed via the inversely proportional relationship of the two variables. Further, the torque provided by the GM200 is significantly higher than the torque provided by a Mr. Coffee® grinder (0.860 Nm (Newton meters) of the GM200 vs. 0.062 Nm of the Mr. Coffee® grinder, respectively), which additionally illustrates the ability (or lack thereof) of the Mr. Coffee® grinder to modify the drug products into a particle size suitable for intranasal abuse. The study evaluated the difference in particle sizes of several different formulations of CII narcotic drug products following modification (grinding) by the GM200 and Mr. Coffee® grinder.

Experimental

The samples tested include those samples listed in Table 21. The formulations of the samples of the present disclosure tested are listed in Tables 13 and 14. The following test equipment was used: Retsch Knife Mill GRINDOMIX GM200, Coffee Grinder (Mr. Coffee®), ATM L3P Sonic Sifter, 500 µm sieve (35 mesh) and a Shimpo Instruments Tachometer. The following testing conditions were used: Analysis speed: 10,000 rpm (GM200), 20,000 rpm (Mr. Coffee®); Analysis time: 30 seconds; Sieve Size: 500 µm (35 mesh); Analysis time: 2 minutes (no pulse). Each sample was prepared in triplicate (N=3).

For each sample, three (3) dosage units were weighed and tested. The following conditions were used with the GM200: a 30 second analysis time and a speed of 10,000 rpm. Both parameters were set prior to each analysis. The composite sample was transferred to a tared weigh boat and the weight of the sample was recorded. The following equation was used to calculate the % sample loss:

$$\text{Sample Loss (\%)} = 100 - \left(\frac{\text{Aanalyzed Sample (mg)}}{\text{Sample Weight (mg)}} \times 100\right)$$

The weight of the 35 mesh sieve and sample pan was recorded. The testing apparatus was assembled with the 35 mesh sieve above the sample pan. The composite sample was transferred to the testing apparatus and analyzed utilizing the following parameters: 2 minute analysis time and no pulse. The analyzed 35 mesh sieve and sample pan were weighed. The % material remaining on the 35 mesh sieve (≥500 µm) and in the sample pan (≤500 µm) was calculated using the following equation:

$$\text{Percent on Sieve (\%)} = \frac{\text{Weight of Sample on Sieve (mg)}}{\text{Total Weight of Sample on Sieve (mg)}} \times 100$$

The procedure was repeated for the Mr. Coffee grinder in place of the GM200. The Mr. Coffee grinder has 1 operating speed (~20.000 rpm). The particle size analysis and grinding results are shown in FIG. 17. FIG. 17 is a representation of particle size results (%≥500 µm) when comparing the tested Extended Release (ER) CII narcotic drug products between manufacturers.

Statistical significance was tested against a 95% confidence interval or a p-value of <0.05. Combined OxyContin® batches provide statistically different (lower) amounts of particles ≥500 µm than combined formulations of the present disclosure (e.g., ER samples and combined Opana® batches following grinding and particle size analysis as described in the protocol).

The results were combined per manufacturer, i.e. the present disclosure, Opana® ER batch results, and OxyContin® results, and analyzed as groups. The combined Opana® batches provide statistically similar amounts of particles ≥500 µm as the combined formulations of the present disclosure (e.g., ER samples) following grinding and particle size analysis.

Alcohol Extraction Example

The purpose of this study was to perform and summarize the results of an alcohol extraction, filtration, and purity testing of the resulting extraction solution for different formulations. Formulations of CII narcotic drug products can be modified from their intended dosage form in order to remove the full dose of the active substance from the dosage form. This is known as making the drug product "abusable." Formulation development has occurred which is intended to reduce the ability of patients to modify the products into this "abusable" form. Extrusion and compress-and-curing are two methods for manufacturing CII drug products. Both methods, when formulated appropriately, possess characteristics which reduce the ability of patients to modify the products into an "abusable" form (when compared to traditional methods).

Twin Screw extrusion can be described as mixing a blended formulation by using shear forces. The co-rotating screws create shear/frictional forces through material contact between the two screws and between the screws and barrel wall. The shear forces work on the material based on its viscosity (inter-particulate friction) to create a homogenous polymer melt. The heated barrels control the melt by maintaining constant temperatures in the various zones of the extruder as well as add additional heat to maintain energy in the process. This happens in a simultaneous continuous process while the material is transferred through the extruder. The polymer melt can then be pushed through a die to form a uniform extrudate. This differs from compress-and-curing which can be described as initially compressing (with force) the blended formulation and then curing (with heat) after the compression in a separate sequential process to produce a finished drug product. CII drug products which utilize each manufacturing method are currently commercially available. In some embodiments, the formulation of the present disclosure is formed by an extrusion process under sufficient shear stresses to impart strength and stability to the formulation. The formulation can be prepared using an extruder wherein shear forces, pressure, and heating are applied together or separately in different zones of the extruder. In some embodiments, the formulation is prepared by reaching a melt flow temperature of the specific formulation in the extruder to assist in producing a uniform extrudate (i.e., localized uniformity). In other embodiments, the formulation is prepared using a compress-and-cure process utilizing preceding, simultaneous, or subsequent heat.

Three principal methods of modifying CII drug products in order to make them "abusable" exist, namely cutting, grinding, and extraction. Cutting the dosage form can be performed in order to increase the surface area of the product prior to ingesting it in an effort to increase the rate of dissolution into the digestive tract. Cutting can also be used to increase the efficiency of grinding or extraction. Cutting alone, however, is not sufficient to render a formulation abuseable. Readily available tools used for cutting are razor blades and common kitchen scissors. Grinding the dosage form is performed in order to decrease the particle size of the product in an effort to insufflate (snort) for immediate release into the blood vessels of the nasal passages. Additional abuse pathways exist which follow the grinding of the product. A readily available tool used for grinding is a commercially available coffee grinder. Extraction is performed in order to dissolve the active substance of the dosage form into a liquid which can be filtered and subsequently swallowed, injected, or otherwise abused. A readily available tool used for extraction is high potency alcohol (i.e., ≥190 proof (95%)).

Figure 19:
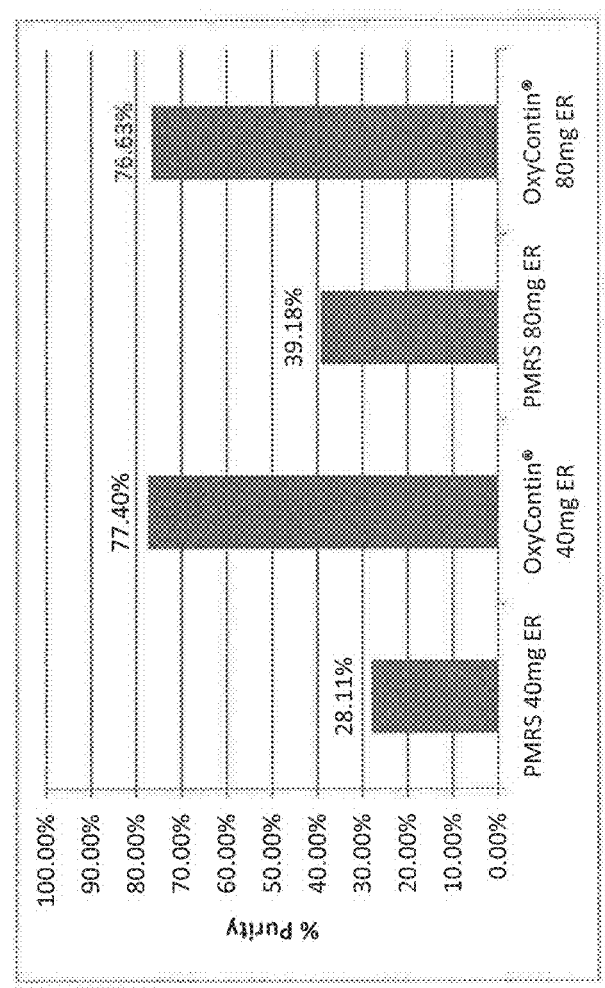
FIG. 19 shows the percent purity of 4 dosage different forms following alcohol extraction.

The purpose of this study was to determine the purity of an alcohol extraction sample using large volumes of high potency alcohol. For this experiment, 40 mg and 80 mg ER formulations of the present disclosure were compared to 40 mg and 80 mg OxyContin® of the RLD. Four (4) whole dosage units were ground using a Retsch Knife Mill GRINDOMIX GM200 at 10,000 RPM for 30 seconds. The samples were then placed in 40.0 mL of 190 proof ethanol. The samples were covered and shaken on a platform shaker at 250 RPM for 3 hours. 5.0 mL of the resulting solution was pipetted off and placed in a beaker. The beaker was heated at ~100° C. until all the ethanol evaporated. Once cooled, the residue was scrapped off weighed, dissolved, and analyzed via a HPLC method validated for quantifying oxycodone HCl content. FIG. 19 shows the percent purity of each of the 4 dosage forms following alcohol extraction. While it is assumed each dosage had ~100% of label claim in the alcohol solution, the ER formulations of the present disclosure have a roughly 2-3 fold decrease in purity of alcohol extract. This is significant due to the fact the alcohol cannot be directly intravenously injected; formulations of a lower purity following alcohol extraction are thought to deter abuse via intravenous injection.

Small Volume Extraction Example

The purpose of this study was to determine if the active substance can be extracted from a dosage form using a small volume of water (relative to a single dosage unit) in a relatively short amount of time. The use of small volumes of water is a common method for abuse since the materials are readily available and the waiting period is generally 1 hour or less. A dosage form able to prevent or reduce small volume extraction is another deterrent to abuse.

As a measure of whether a solution would be able to be intravenously injected by an abuser the viscosity of the resulting small volume extraction solutions is measured or calculated. An extended release 80 mg dosage form of the present disclosure was compared to an 80 mg OxyContin® (reformulated), a 40 mg Opana® ER (reformulated), and a 30 mg Roxicodone® IR dosage form. Ten (10) pills of each dosage form were cut in half and placed in 30 mL of water at 90° C. Three (3) beakers of each dosage form were set up in order to test three time points: 30 minutes, 45 minutes, and 60 minutes. The samples were left unagitated. It is believed that non-agitation is a preferred method for extracting the active substance without increasing the solution viscosity. Agitation is believed to activate the high molecular weight, water soluble excipients. At each given time point, a 1 mL sample was taken for HPLC analysis of oxycodone HCl content and presented as percent of label claim. The remaining solution was subsequently decanted from the beaker for viscosity analysis via capillary viscometer at 25° C. The results of the oxycodone HCl content and resulting viscosity are represented in Table 31 and Table 32, respectively.

TABLE 31

Aqueous Small Volume Extraction Oxycodone HCl Content

| Product | Oxycodone HCl Content (% of Label Claim) | | |
|---|---|---|---|
| | 30 minutes | 45 minutes | 60 minutes |
| Roxicodone ® 30 mg | 76.8 | 98.0 | 115.7 |
| OxyContin ® 80 mg | 34.0 | 48.9 | 59.1 |
| Present Disclosure ER 80 mg | 34.0 | 43.8 | 52.5 |

TABLE 32

Aqueous Small Volume Extraction Viscosity

| Product | Viscosity (Centistokes (cSt) @ 25° C.) | | |
|---|---|---|---|
| | 30 minutes | 45 minutes | 60 minutes |
| Roxicodone ® 30 mg | 1.0 | 1.0 | 1.0 |
| OxyContin ® 80 mg | 1.4 | 1.7 | 2.1 |
| Opana ® ER 40 mg | 1.3 | 2.4 | 2.4 |
| Present Disclosure ER 80 mg | 22.3 | 60.8 | 70.3 |

TABLE 33

Aqueous Small Volume Extraction Drug Product Excipients

| Product | Polyethylene Oxide Content | HPMC |
|---|---|---|
| Roxicodone ® 30 mg | N/A | N/A |
| OxyContin ® 80 mg | High MW PEO (≥1,000,000 Daltons) | Yes |
| Opana ® ER 40 mg | High MW PEO (≥1,000,000 Daltons) | Yes |
| Present Disclosure ER 80 mg | Low MW PEO (≤1,000,000 Daltons) | Yes |

Following 30, 45, and 60 minutes, OxyContin® 80 mg provided oxycodone HCl content results which were 0.0% LC, 5.1% LC, and 6.6% LC (absolute) higher, respectively, than the present disclosure ER 80 mg formulations. While the present disclosure ER 80 mg releases less oxycodone HCl when compared to OxyContin® 80 mg ER, the difference at all three time points is small.

Following 30, 45, and 60 minutes, OxyContin® 80 mg provided viscosity results not more than 3× that of Roxicodone® 30 mg IR. Roxicodone® IR dosage form is a traditional directly compressed tablet with no abuse deterrent features. As a result, the Roxicodone® IR solution has no increased viscosity over a water only sample (~1 cSt). Following 30, 45, and 60 minutes, Opana® ER 40 mg provided viscosity results relatively similar to OxyContin® 80 mg with viscosities not more than 3× higher than Roxicodone® 30 mg IR. Following 30, 45, and 60 minutes, present disclosure ER 80 mg formulations provided an increase in viscosity of approximately 16×, 36×, and 33×, respectively, when compared to OxyContin® 80 mg; approximately 17×, 25×, and 29×, respectively, when compared to Opana® ER 40 mg; and 22×, 61× and 70×, respectively, when compared to Roxicodone® 30 mg IR. The present disclosure 80 mg dosage form of the present disclosure exhibits similar and/or reduced concentration of oxycodone HCl when compared to OxyContin® 80 mg ER in small volume aqueous extraction and also provides a marked increase in viscosity over other extended release dosage forms at all three time points. The dosage forms of the present disclosure exhibit a 1.5×, 2×, 3×, 4 s, 5×, 10 Ox, 15×, 20×, 25×, 30×, 40×, 50×, 60×, 70×, 80×, 90×, or 100× increase in the small volume extraction viscosity as described herein over other dosage formulations that do not contain a low molecular weight matrix agents, e.g., about 50K to under 1M Daltons PEO, at least about 5%, 10%, 15%, 20%, 25%, 30%, 35%, 40%, 45%, 50%, 55%, or about 60% HPMC (or equivalent), or both.

While this disclosure has been particularly shown and described with reference to example embodiments thereof, it will be understood by those skilled in the art that various changes in form and details may be made therein without departing from the scope of the invention encompassed by the appended claims.

We claim:

1. An oral, extended release, abuse deterrent pill comprising a drug and
   (i) 30 wt % to 50 wt % of polyethylene oxide having an average molecular weight between 50K Daltons and 150K Daltons;
   (ii) 8 wt % to 60 wt % of a controlled release agent;
   (iii) 0.2 wt % to 20 wt % polyethylene glycol, wherein the polyethylene glycol has an average molecular weight of 3K to 9K Daltons;
       wherein the drug is not oxymorphone, and has an extended release profile,
       wherein the pill has at least 50 wt % of particles with a particle size greater than 0.5 mm following physical or mechanical manipulation of the pill, and
       wherein the pill is a formed, uniform extrudate having a uniform blend of the drug, the polyethylene oxide, the controlled release agent, and the polyethylene glycol, and is directly formed from an extrusion process.

2. The oral, extended release, abuse deterrent pill of claim 1, wherein the controlled release agent is selected from the group consisting of polyvinyl acetate, polyvinylpyrrolidone, ethylcellulose, hydroxypropyl methylcellulose, hydroxypropylcellulose, hydroxymethylcellulose, poly(meth)acrylic acid and derivatives, or combinations thereof.

3. The oral, extended release, abuse deterrent pill of claim 2, wherein the formulation contains 15 wt % to 45 wt % hydroxypropyl methylcellulose as the controlled release agent.

4. The oral, extended release, abuse deterrent pill of claim 2, wherein the formulation contains 29 wt % to 60 wt % of a combination of polyvinyl acetate and polyvinylpyrrolidone as the controlled release agent.

5. The oral, extended release, abuse deterrent pill of claim 1, wherein the polyethylene glycol has an average molecular weight of 8K Daltons.

6. The oral, extended release, abuse deterrent pill of claim 1, wherein the drug is present at 1 to 50 wt % of the pill.

7. The oral, extended release, abuse deterrent pill of claim 1, wherein the pill further comprises at least one preservative or antioxidant selected from the group consisting of silica, sodium laurel sulfate, citric acid, butylated hydroxytoluene (BHT), ascorbic acid, ascorbyl palmitate, butylated hydroxyanisole (BHA), erythorbic acid, hypophosphorous acid, lactobionic acid, monothioglycerol, potassium metabisulfite, propyl gallate, racemethionine, sodium bisulfite, sodium formaldehyde sulfoxylate, sodium metabisulfite, sodium sulfite, sodium thiosulfate, stannous chloride, sulfur dioxide and tocopherols.

8. The oral, extended release, abuse deterrent pill of claim 1,
   wherein between 20% and 40% of the drug is released from the pill after 1 hour of exposure to simulated gastric fluid,
   wherein between 35% and 55% of the drug is released from the pill after 2 hours of exposure to simulated gastric fluid,
   wherein between 55% and 75% of the drug is released from the pill after 4 hours of exposure to simulated gastric fluid,
   wherein between 70% and 90% of the drug is released from the pill after 6 hours of exposure to simulated gastric fluid, and
   wherein not less than 80% of the drug is released from the pill after 8 hours of exposure to simulated gastric fluid.

9. The oral, extended release, abuse deterrent pill of claim 1 directly formed from a hot melt extrusion process having a forming unit selected from the group consisting of a calendar, a rotary, and a chain forming machine.

10. The oral, extended release, abuse deterrent pill of claim 1, wherein the pill exhibits less than a 10% increase in the release of the drug in a simulated alcoholic gastric fluid environment comprising 90% simulated gastric fluid (SGF) and 10% ethanol, compared to a control comprising 100% SGF.

* * * * *